(12) United States Patent
Tipler

(10) Patent No.: US 9,423,383 B2
(45) Date of Patent: Aug. 23, 2016

(54) CHROMATOGRAPHY SYSTEMS AND METHODS USING THEM

(71) Applicant: Andrew Tipler, Trumbull, CT (US)

(72) Inventor: Andrew Tipler, Trumbull, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 14/275,334

(22) Filed: May 12, 2014

(65) Prior Publication Data

US 2015/0013770 A1 Jan. 15, 2015

Related U.S. Application Data

(63) Continuation of application No. 12/472,948, filed on May 27, 2009, now Pat. No. 8,303,694, which is a continuation of application No. 13/657,079, filed on Oct. 22, 2012, now Pat. No. 8,721,768.

(60) Provisional application No. 61/056,225, filed on May 27, 2008, provisional application No. 61/142,702, filed on Jan. 6, 2009, provisional application No. 61/142,705, filed on Jan. 6, 2009, provisional application No. 61/158,001, filed on Mar. 6, 2009, provisional application No. 61/179,028, filed on May 18, 2009.

(51) Int. Cl.
*G01N 30/32* (2006.01)
*G01N 30/20* (2006.01)
*G01N 30/28* (2006.01)
*G01N 30/46* (2006.01)
*G01N 30/60* (2006.01)
*G01N 30/72* (2006.01)

(52) U.S. Cl.
CPC .............. *G01N 30/32* (2013.01); *G01N 30/20* (2013.01); *G01N 30/28* (2013.01); *G01N 30/466* (2013.01); *G01N 30/6095* (2013.01); *G01N 30/72* (2013.01); *G01N 30/7206* (2013.01); *G01N 2030/208* (2013.01); *G01N 2030/324* (2013.01); *G01N 2030/328* (2013.01); *Y10T 29/49* (2015.01); *Y10T 137/0318* (2015.04)

(58) Field of Classification Search
CPC ... G01N 30/28; G01N 30/32; G01N 30/6078; G01N 2030/324; G01N 30/20; G01N 30/6095
See application file for complete search history.

(56) References Cited

U.S. PATENT DOCUMENTS

| | | | |
|---|---|---|---|
| 2006/0278076 A1* | 12/2006 | Tipler | G01N 30/30 95/87 |
| 2007/0074766 A1* | 4/2007 | Klee | G01N 30/32 137/487.5 |
| 2009/0165873 A1* | 7/2009 | Chordia | G01N 30/84 137/597 |
| 2009/0183634 A1* | 7/2009 | Zeeuw | G01N 30/16 96/106 |
| 2009/0249959 A1* | 10/2009 | Jones | B01D 53/0415 96/106 |

* cited by examiner

*Primary Examiner* — Robert Clemente
(74) *Attorney, Agent, or Firm* — Rhodes IP PLC; Christopher R Rhodes

(57) ABSTRACT

Certain embodiments described herein are directed to chromatography systems that include a microfluidic device. The microfluidic device can be fluidically coupled to a switching valve to provide for selective control of fluid flow in the chromatography system. In some examples, the microfluidic device may include a charging chamber, a bypass restrictor or other features that can provide for added control of the fluid flow in the system. Methods of using the devices and methods of calculating lengths and diameters to provide a desired flow rate are also described.

22 Claims, 53 Drawing Sheets

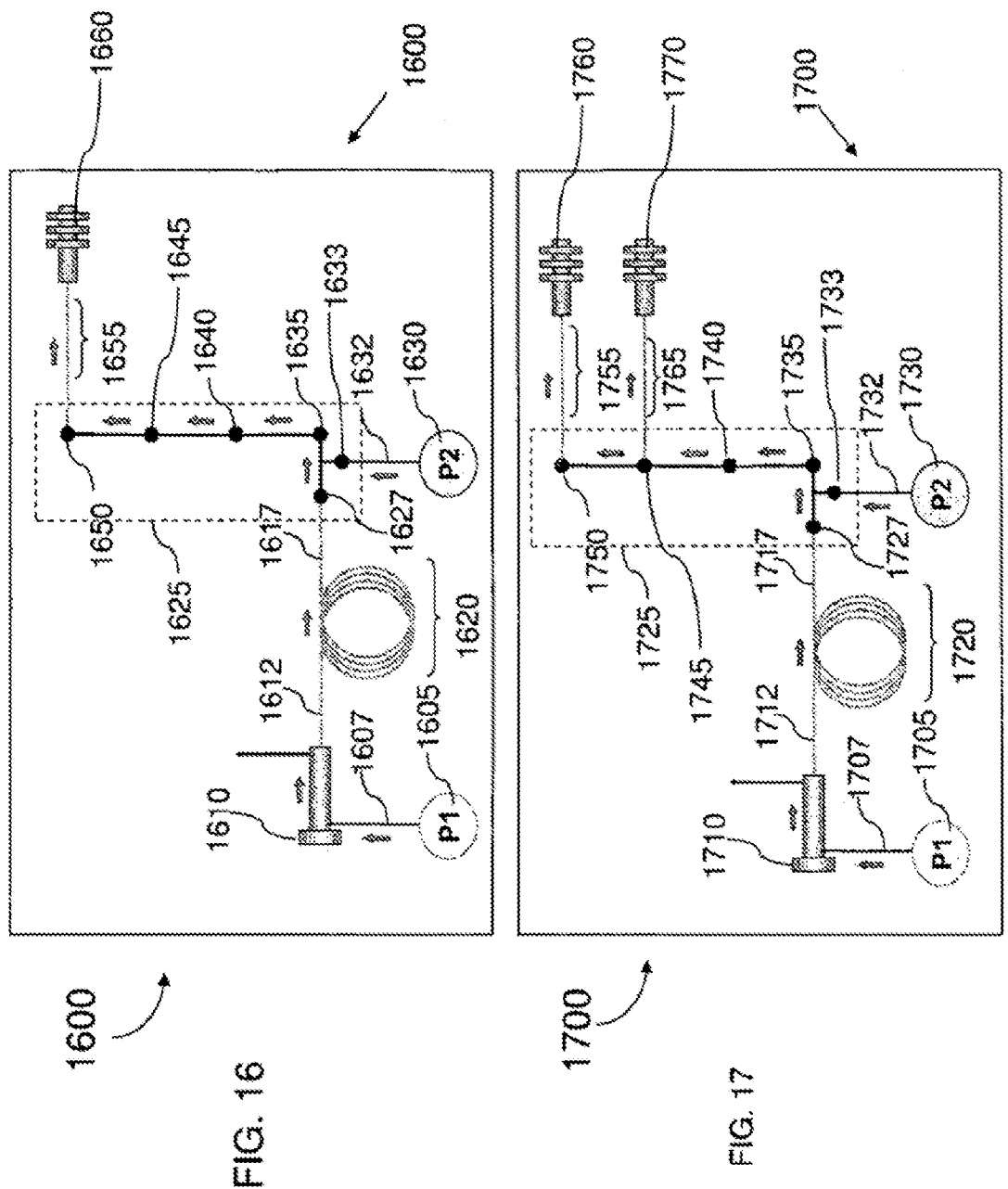

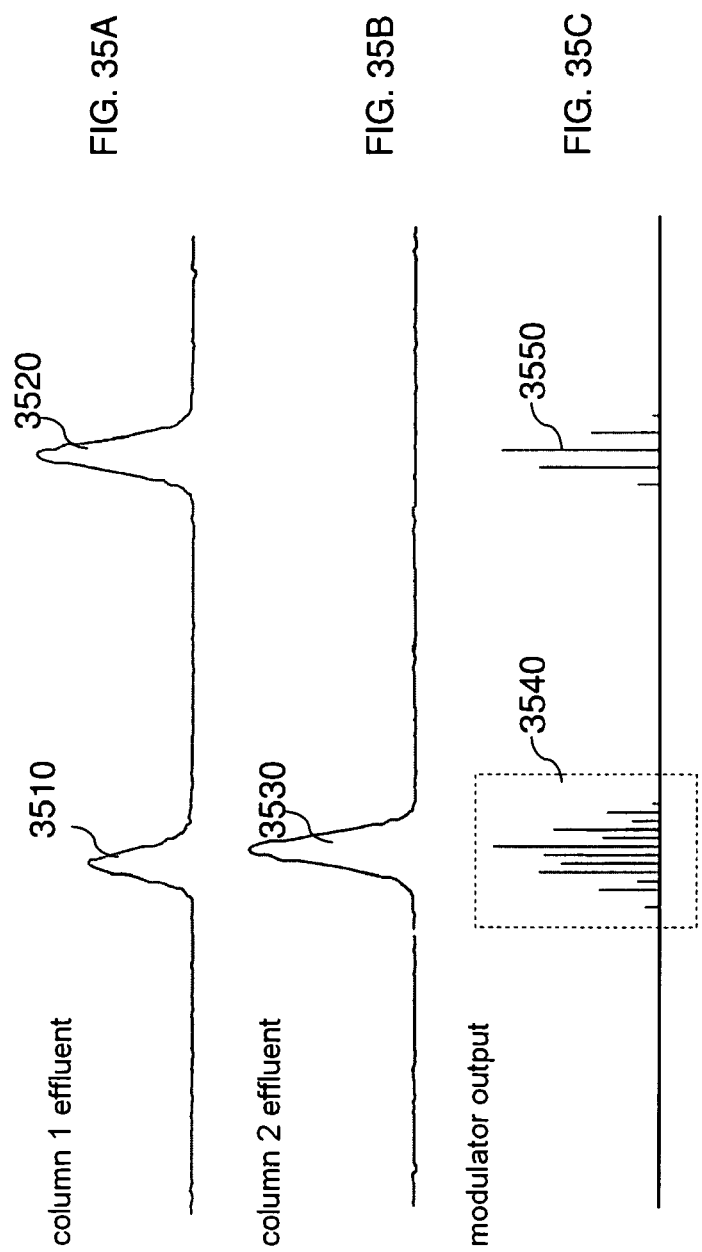

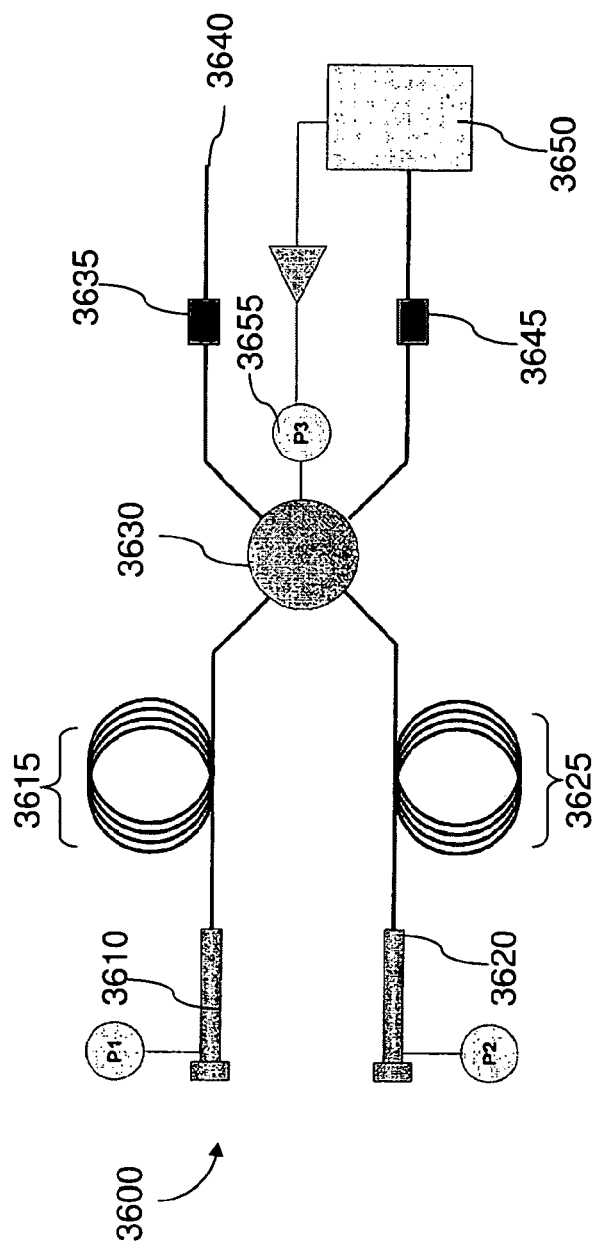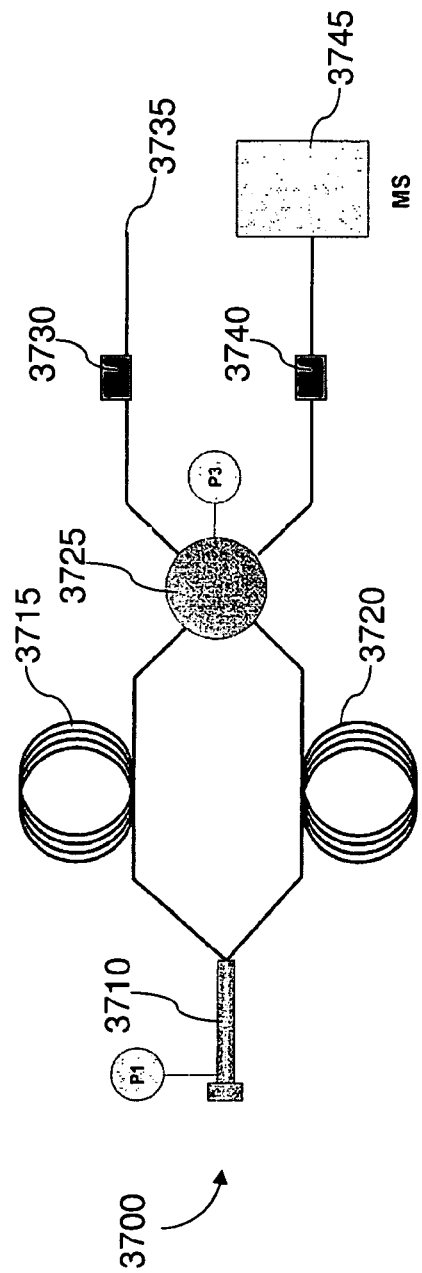

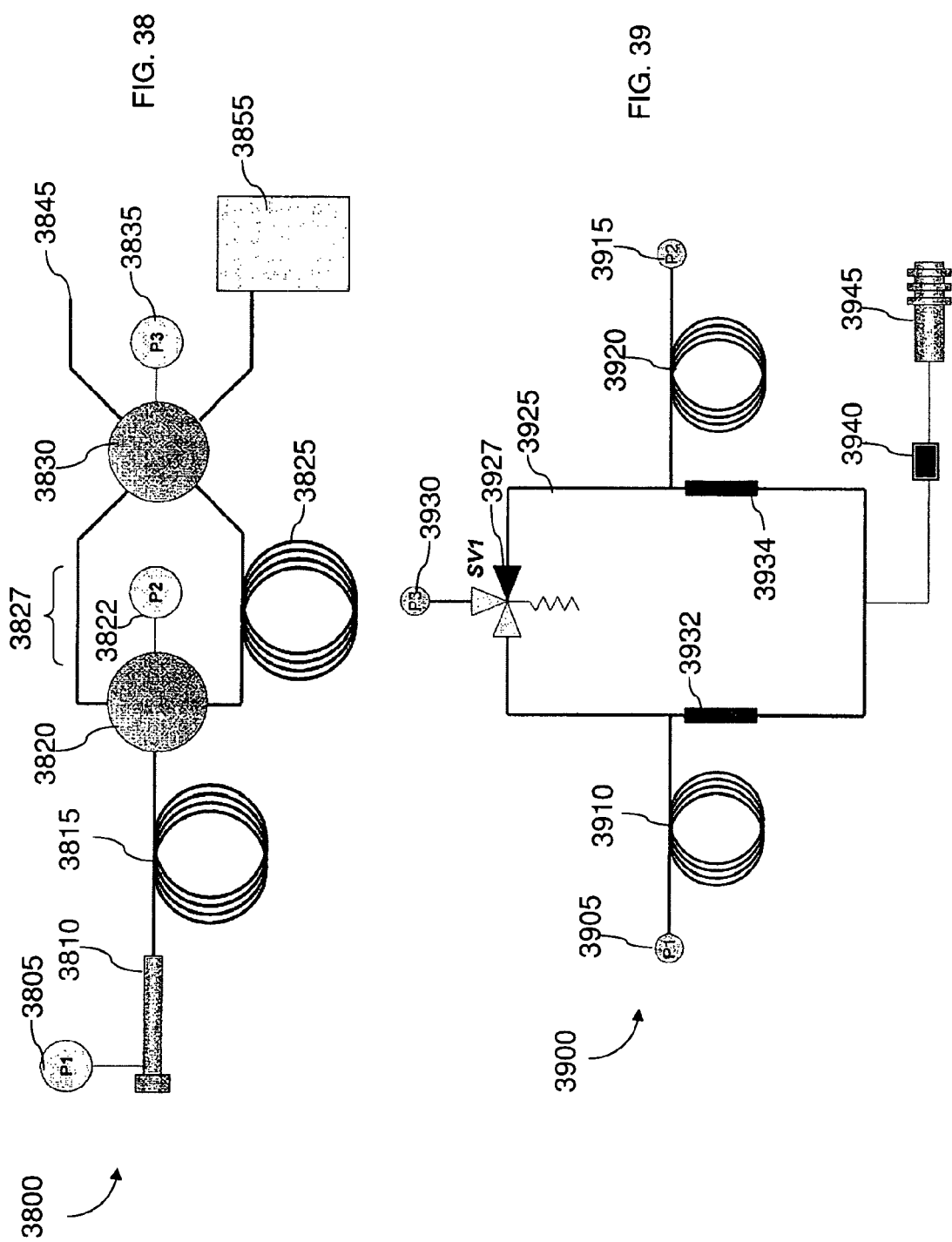

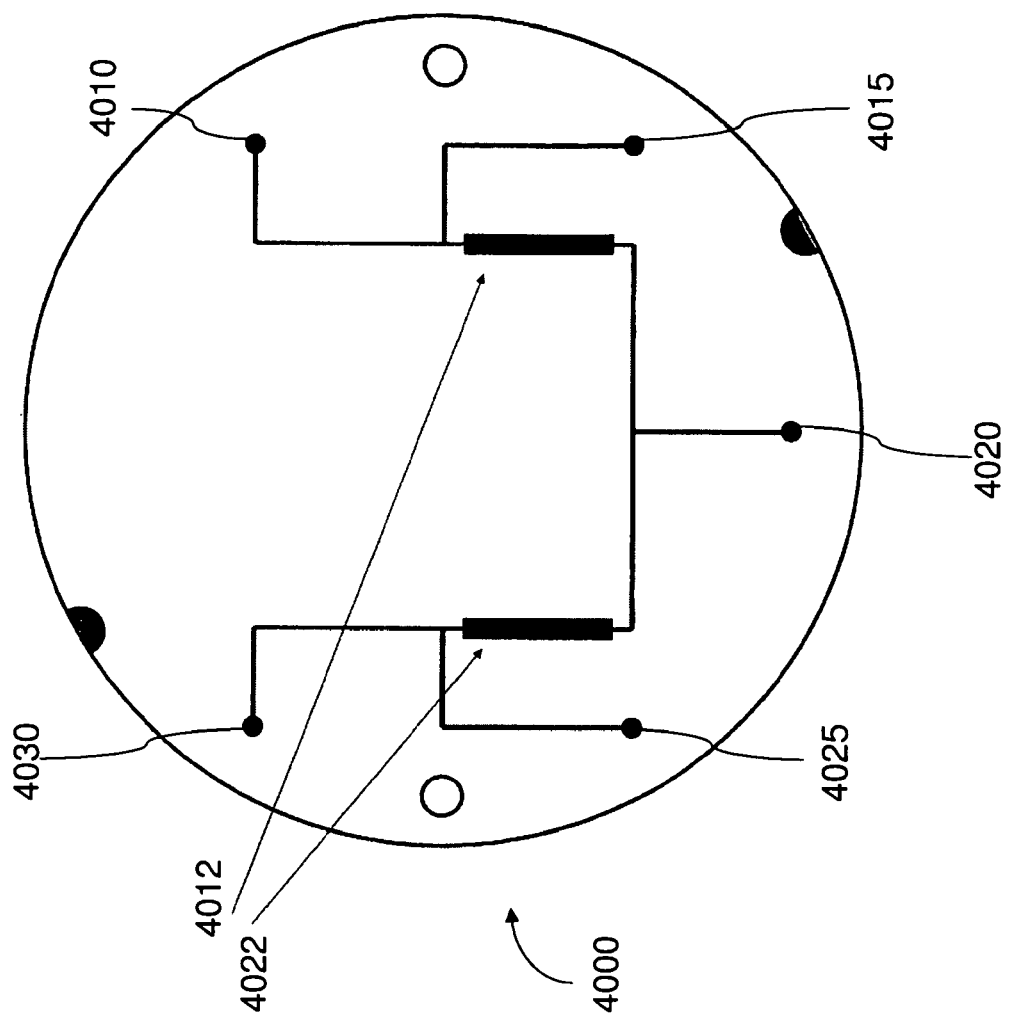

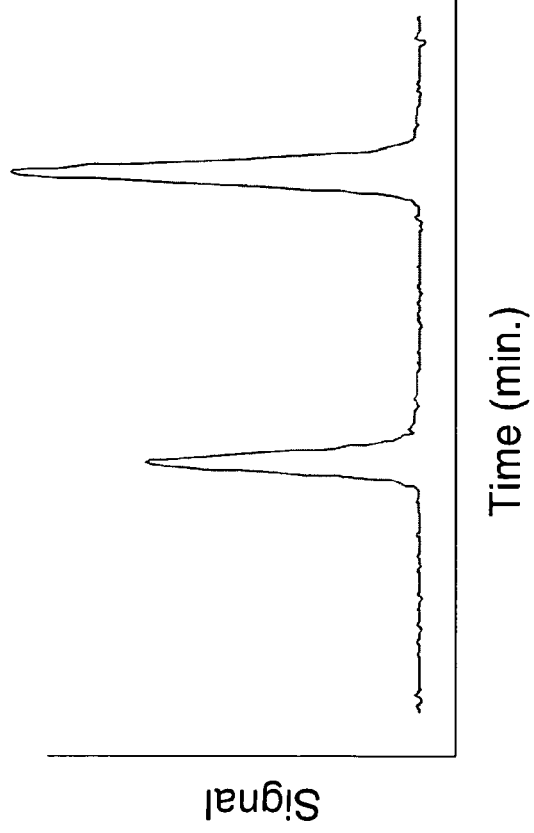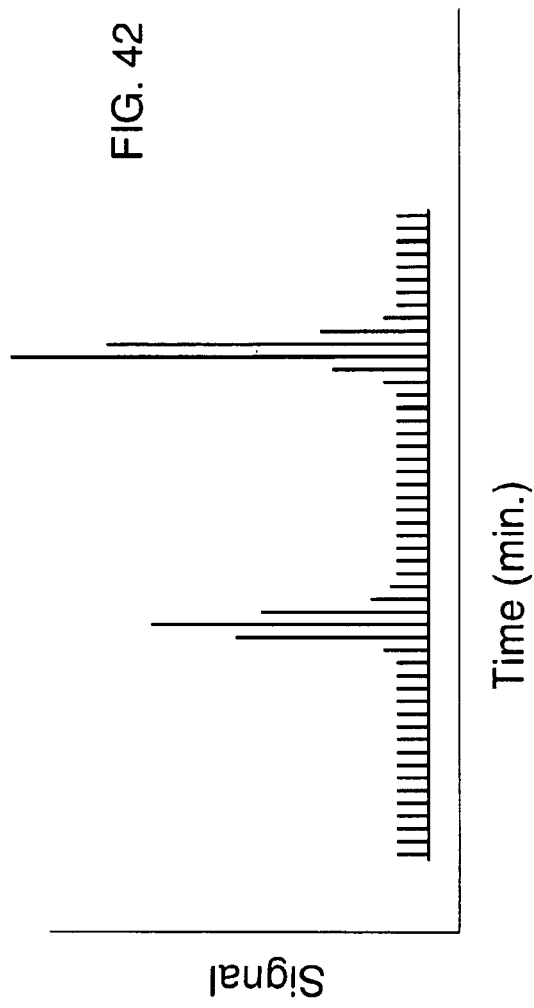

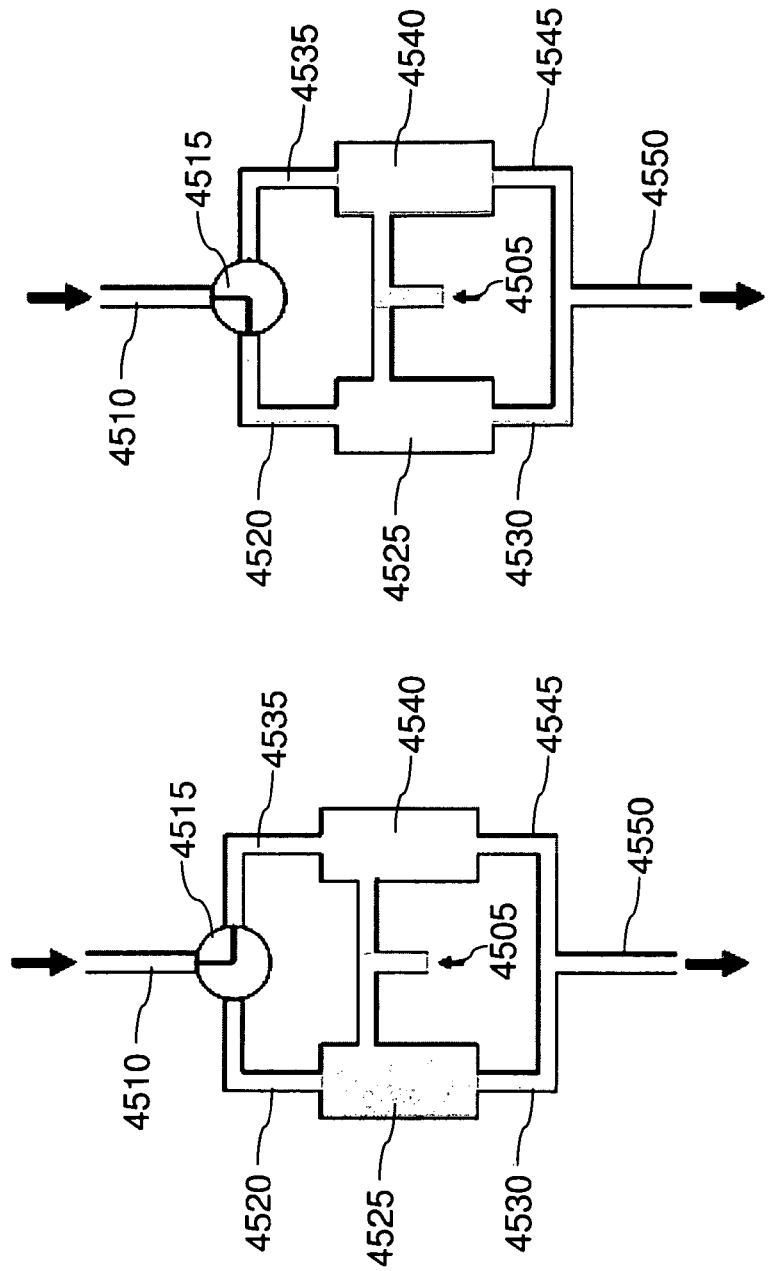

CHROMATOGRAPHY SYSTEMS AND METHODS USING THEM

PRIORITY APPLICATIONS

This application claims priority to U.S. application Ser. No. 13/657,079 (now U.S. Pat. No. 8,721,768) filed on Oct. 22, 2012. U.S. application Ser. No. 13/657,079 claimed priority to U.S. application Ser. No. 12/472,948 (now U.S. Pat. No. 8,303,694) filed on Mar. 27, 2009. U.S. application Ser. No. 12/472,948 claimed priority to each of U.S. Provisional Patent Application No. 61/056,225 filed on May 27, 2008, to U.S. Provisional Patent Application No. 61/142,702 filed on Jan. 6, 2009, to U.S. Provisional Patent Application No. 61/142,705 filed on Jan. 6, 2009, to U.S. Provisional Patent Application No. 61/158,001 filed on Mar. 6, 2009 and to U.S. Provisional Patent Application No. 61/179,028 filed on May 18, 2009, the entire disclosure of each of which is hereby incorporated herein by reference in its entirety.

TECHNOLOGICAL FIELD

Certain features, aspect and embodiments are directed to gas chromatography systems. In particular, certain embodiments are directed to chromatography systems that include a microfluidic device to control fluid flow to one or more other components in the system.

BACKGROUND

Separations of complex samples can be difficult with existing chromatography systems. In particular, samples having peaks that elute closely can be difficult to separate. In addition, there may also be a need for backflushing, heartcutting, column switching and detector switching.

SUMMARY

In one aspect, a chromatography system comprising a first injector fluidically coupled to a first column, a second injector fluidically coupled to a second column, a microfluidic device fluidically coupled to the first column and the second column, the microfluidic device comprising an internal microchannel fluidically coupled to a switching valve, and a detector fluidically coupled to the microfluidic device and configured to receive effluent from the first column when the switching valve is actuated to a first position and to receive effluent from a second column when the switching valve is actuated to a second position is provided.

In certain embodiments, the microfluidic device can include a first port fluidically coupled to the first column and a second port fluidically coupled to the second column. In certain examples, the detector is a mass spectrometer. In some examples, the system can include a second detector fluidically coupled to the microfluidic device. In certain embodiments, the system can also include a modulating gas source fluidically coupled to the microfluidic device. In some examples, the internal microchannel comprises a first charging chamber. In certain embodiments, the switching valve permits fluid flow from the modulating gas source to the first charging chamber in a first position and restricts fluid flow from the modulating gas source to the first charging chamber in a second position. In certain examples, the system can further include a second charging chamber in the microchannel. In some embodiments, the switching valve permits fluid flow from the modulating gas source to the first charging chamber in a first position and restricts fluid flow from the modulating gas source to the first charging chamber in a second position and permits fluid flow from the modulating gas source to the second charging chamber in the second position. In certain embodiments, the system may include a restrictor between the detector and the microfluidic device to balance fluid flow in the system.

In another aspect, a chromatography system comprising an injector fluidically coupled to a first column, a microfluidic device fluidically coupled to the first column, the microfluidic device fluidically coupled to a switching valve through a port on the microfluidic device, a second column fluidically coupled to the microfluidic device, and a first detector fluidically coupled to the second column is disclosed.

In certain embodiments, the system can further include a second detector fluidically coupled to the microfluidic device through a restrictor between the microfluidic device and the second detector. In certain examples, the system can further include a second detector fluidically coupled to the microfluidic device through a third column between the microfluidic device and the second detector. In some examples, the system may further include a restrictor between the second column and the first detector. In other examples, the microfluidic device comprises an internal bypass restrictor in the microchannel. In certain examples, the system can be configured to receive the second column receives effluent from the first column when the switching valve is in a first position and the third column receives effluent from the first column when the switching valve is in a second position. In some examples, the system can include a third detector fluidically coupled to the microfluidic device through a fourth column between the microfluidic device and the third detector. In some embodiments, the system can include a vent fluidically coupled to the microfluidic device through a restrictor between the vent and the microfluidic device. In certain embodiments, the system further comprises a vent fluidically coupled to the microfluidic device through a restrictor between the vent and the microfluidic device. In certain examples, the system includes a charging chamber in a microchannel of the microfluidic device.

In an additional aspect, a chromatography system comprising an injector, a column fluidically coupled to the injector, a microfluidic device fluidically coupled to the column and fluidically coupled to a switching valve, the microfluidic device comprising an inlet port to receive effluent from the column, an modulating gas port to receive a modulating gas, and at least one outlet port, each of the ports in fluid communication through an internal microchannel in the microfluidic device, a restrictor fluidically coupled to a first outlet port of the microfluidic device and a first detector fluidically coupled to the restrictor is provided.

In certain embodiments, the system comprises a bypass restrictor in the internal microchannel, the bypass restrictor configured to reduce fluid flow through the microfluidic device. In certain examples, the system includes a charging chamber in the microchannel. In other examples, the system includes a second restrictor fluidically coupled to a second outlet port of the microfluidic device. In some embodiments, the system can include a second detector fluidically coupled to the second restrictor. In other embodiments, the system can include a third restrictor fluidically coupled to a third outlet port of the microfluidic device. In certain embodiments, the system can include a third detector fluidically coupled to the third restrictor. In some examples, the system can include a fourth restrictor fluidically coupled to a fourth outlet port of the microfluidic device. In some embodiments, the system further comprises a fourth detector fluidically coupled to the fourth restrictor. In certain examples, the system can include a sniffer port fluidically coupled to a second outlet port of the microfluidic device through a restrictor between the second outlet port of the microfluidic device and the sniffer port.

In another aspect, a chromatography system comprising an injector, a first column fluidically coupled to the injector, a microfluidic device fluidically coupled to the column and fluidically coupled to a switching valve, the microfluidic device comprising an inlet port to receive effluent from the column, an modulating gas port to receive a modulating gas, and at least one outlet port, each of the ports in fluid communication through an internal microchannel in the microfluidic device, a second column fluidically coupled to a first outlet port of the microfluidic device and a first detector fluidically coupled to the second column is disclosed.

In certain embodiments, the system can include a bypass restrictor in the internal microchannel, the bypass restrictor configured to reduce fluid flow through the microfluidic device. In other embodiments, the system can include a charging chamber in the microchannel. In some examples, the system can include a restrictor fluidically coupled to a second outlet port of the microfluidic device. In additional examples, the system can include a second detector fluidically coupled to the restrictor. In certain embodiments, the system can include a third column fluidically coupled to a third outlet port of the microfluidic device. In some examples, the system can include a third detector fluidically coupled to the third column. In other examples, the system can include a fourth column fluidically coupled to a fourth outlet port of the microfluidic device. In some examples, the system can include a fourth detector fluidically coupled to the fourth column. In additional embodiments, the system can include a sniffer port fluidically coupled to a second outlet port of the microfluidic device through a restrictor between the second outlet port of the microfluidic device and the sniffer port.

In an additional aspect, a chromatography system comprising an injector, a microfluidic device fluidically coupled to the injector and fluidically coupled to a switching valve, the microfluidic device comprising an inlet port to receive sample from the injector, a modulating gas port to receive a modulating gas, and at least one outlet port, each of the ports in fluid communication through an internal microchannel in the microfluidic device, a first column fluidically coupled to a first outlet port of the microfluidic device, and a first detector fluidically coupled to the first column is disclosed.

In certain embodiments, the system can include a bypass restrictor in the internal microchannel, the bypass restrictor configured to reduce fluid flow through the microfluidic device. In other embodiments, the system can include a charging chamber in the microchannel. In additional embodiments, the system can include a restrictor fluidically coupled to a second outlet port of the microfluidic device. In some examples, the system can include a second detector fluidically coupled to the restrictor. In other examples, the system can include a third column fluidically coupled to a third outlet port of the microfluidic device. In additional examples, the system can include a third detector fluidically coupled to the third column. In other examples, the system can include a fourth column fluidically coupled to a fourth outlet port of the microfluidic device. In some examples, the system can include a fourth detector fluidically coupled to the fourth column. In other examples, the system can include a sniffer port fluidically coupled to a second outlet port of the microfluidic device through a restrictor between the second outlet port of the microfluidic device and the sniffer port.

In another aspect, a chromatography system comprising a first injector fluidically coupled to a first column, a second injector fluidically coupled to a second column, a microfluidic device fluidically coupled to the first column and the second column, the microfluidic device comprising an internal microchannel fluidically coupled to a switching valve, a first detector fluidically coupled to the microfluidic device, and a second detector fluidically coupled to the microfluidic device, in which the microfluidic device is configured, in a first position, to provide effluent from the first column to the first detector and effluent from the second column to the second detector and is configured, in a second position, to provide the effluent from the first column to the second detector and the effluent from the second column to the first detector in a second position is provided.

In certain embodiments, the system can include a first restrictor between the first detector and the microfluidic device and a second restrictor between the second detector and the microfluidic device. In some embodiments, the system can include an internal crossover channel in the microchannel of the microfluidic device, the switching valve configured to permit fluid flow through the crossover channel in the second position. In some embodiments, at least one of the first and second detectors is a mass spectrometer. In other examples, the system can include a third column fluidically coupled to the second detector and between the second detector and the microfluidic device. In certain examples, the system includes a charging chamber in the microchannel.

In an additional aspect, a chromatography system comprising a first injector fluidically coupled to a first column, a second injector fluidically coupled to a second column, a microfluidic device fluidically coupled to the first column and the second column, the microfluidic device comprising an internal microchannel fluidically coupled to a switching valve, a first detector fluidically coupled to the microfluidic device, and a vent fluidically coupled to the microfluidic device, in which the microfluidic device is configured to provide effluent from the first column to the first detector and effluent from the second column to the vent in a first position and to provide the effluent from the first column to the vent and the effluent from the second column to the first detector in a second position is disclosed.

In certain embodiments, the system can include a first restrictor between the first detector and the microfluidic device and a second restrictor between the vent and the microfluidic device. In other embodiments, the system can include an internal crossover channel in the microchannel of the microfluidic device, the switching valve configured to permit fluid flow through the crossover channel in the second position. In additional embodiments, at least one of the first and second detectors is a mass spectrometer. In some embodiments, the system can include a third column fluidically coupled to the first detector and between the first detector and the microfluidic device. In certain examples, the system includes a charging chamber in the microchannel.

In another aspect, a chromatography system comprising a first injector fluidically coupled to a first column, a first microfluidic device fluidically coupled to the first column and comprising an internal microchannel fluidically coupled to a switching valve, a second microfluidic device fluidically coupled to the first microfluidic device, the second microfluidic device comprising an internal microchannel fluidically coupled to a switching valve and a detector fluidically coupled to the second microfluidic device is provided.

In certain embodiments, the system can include a second column between the first and second microfluidic devices and fluidically coupled to each of the first and second microfluidic devices. In other embodiments, the system can include a second detector fluidically coupled to the first microfluidic device. In some examples, the system can include a second detector fluidically coupled to the second microfluidic device. In additional examples, the system can include a second column between the second microfluidic device and the detector and fluidically coupled to each of the second microfluidic device and the detector. In certain examples, the system includes a charging chamber in a microchannel of one or more of the first and second microfluidic devices.

In an additional aspect, a chromatography system comprising a first injector fluidically coupled to a first column, a second injector fluidically coupled to a second column, a microfluidic device fluidically coupled to the first column through a first port and fluidically coupled to the second column through a second port, the microfluidic device comprising a first charging chamber fluidically coupled to the first port and a second charging chamber fluidically coupled to the second port, and a switching valve fluidically coupled to the microfluidic device and to a modulating gas source, the switching valve configured, in a first position, to permit flow of a modulating gas from the modulating gas source to sweep effluent from the first charging chamber to a detector fluidically coupled to the microfluidic device, the switching valve further configured, in a second position, to permit flow of the modulating gas from the modulating gas source to the second charging chamber to sweep effluent from the second charging chamber to the detector fluidically coupled to the microfluidic device.

In certain embodiments, the system can be configured with a first detector fluidically coupled to the first charging chamber and a second detector fluidically coupled to the second charging chamber. In other examples, the switching valve can be configured to be actuated between the first and second positions to provide pulsed flow from the first charging chamber to the detector and from the second charging chamber to the detector. In additional examples, the switching valve is a 3-way solenoid valve. In other examples, the detector is a mass spectrometer.

In another aspect, a microfluidic device comprising a laminated substrate comprising a plurality of ports each connected to the other in series through an internal microfluidic channel is provided. In some examples, the microchannels can be configured in a desired manner, e.g., with an internal bypass restrictor.

In certain embodiments, the microfluidic device comprises a switching valve fluidically coupled to at least one of the plurality of ports. In additional examples, the switching valve is a solenoid valve. In some examples, the device can include at least one chromatography column fluidically coupled to a first port of the microfluidic device. In some examples, a detector can be fluidically coupled to a second port of the microfluidic device. In certain examples, the detector is a mass spectrometer. In other examples, the device may further comprise an additional chromatography column fluidically coupled to a third port of the microfluidic device. In some examples, the device can include a restrictor fluidically coupled to the microfluidic device and positioned between the at least one detector and the microfluidic device. In additional examples, the device can include a second detector fluidically coupled to a fourth port of the microfluidic device. In some embodiments, the device can include an additional restrictor fluidically coupled to the microfluidic device and positioned between the second detector and the microfluidic device. In certain embodiments, the device can include a modulating gas source fluidically coupled to a fifth port upstream of the second, third and fourth ports and configured to provide the modulating gas to sweep effluent from the microchannel. In some examples, the microchannel comprises a charging chamber. In certain examples, the charging chamber comprises a section having an increased diameter as compared to other sections of the microchannel. In some examples, the modulating gas source is fluidically coupled to charging chamber and modulating gas can flow from the modulating gas source to the charging chamber when the switching valve is actuated to a first position. In other examples, the modulating gas flow to the charging chamber is restricted when the switching valve is actuated to a second position.

In an additional aspect, a microfluidic device comprising a laminated substrate comprising at least one inlet port and a plurality of outlet ports each fluidically coupled to the inlet port through a microchannel in the laminated substrate, and an internal bypass restrictor in the laminated substrate, the internal bypass restrictor fluidically coupled to the microchannel and configured to restrict fluid flow in the microchannel is provided.

In certain embodiments, the device can include a switching valve fluidically coupled to at least one of the ports. In other embodiments, the switching valve is a solenoid valve. In some examples, the device can include at least one chromatography column fluidically coupled to a first port of the microfluidic device. In additional embodiments, the device can include a detector fluidically coupled to a second port of the microfluidic device. In some examples, the detector is a mass spectrometer. In other examples, the device can include an additional chromatography column fluidically coupled to a third port of the microfluidic device. In additional examples, the device can include a restrictor fluidically coupled to the microfluidic device and positioned between the at least one detector and the microfluidic device. In some examples, the device can include a second detector fluidically coupled to a fourth port of the microfluidic device. In certain examples, the device can include an additional restrictor fluidically coupled to the microfluidic device and positioned between the second detector and the microfluidic device. In some examples, the device can include a modulating gas source fluidically coupled to a fifth port upstream of the second, third and fourth ports and configured to provide the modulating gas to sweep effluent from the microchannel. In some embodiments, the microchannel comprises a charging chamber. In other embodiments, the charging chamber comprises a section having an increased diameter as compared to other sections of the microchannel. In additional embodiments, the modulating gas source is fluidically coupled to charging chamber and modulating gas can flow from the modulating gas source to the charging chamber when the switching valve is actuated to a first position. In some examples, the modulating gas flow to the charging chamber is restricted when the switching valve is actuated to a second position.

In another aspect, a method of modulating the flow of fluid in a chromatography system, the method comprising actuating a switching valve between a first position and a second position, the first position permitting fluid flow from a modulating gas source to a first charging chamber of a microfluidic device to provide column effluent from the first charging chamber to a detector fluidically coupled to the microfluidic device, and the second position permitting fluid flow from the modulating gas source to the second charging chamber of the microfluidic device to provide column effluent from the second charging chamber to the detector fluidically coupled to the microfluidic device is disclosed.

In certain embodiments, the switching valve is a 3-way solenoid valve that is actuated at a frequency of about 10 Hz to about 100 Hz. In some embodiments, the method can include balancing pressure in the system by configuring the system with a restrictor between the detector and the microfluidic device. In other examples, the method can include providing the column effluent from the first charging chamber to a first detector fluidically coupled to the microfluidic device and providing the column effluent from the second charging chamber to a second detector fluidically coupled to the microfluidic device. In some examples, the method can include balancing the pressure in the system by configuring the system with a first restrictor between the first detector and the microfluidic device and with a second restrictor between the second detector and the microfluidic device. In certain examples, the method can include configuring each of the first and second charging chambers as internal chambers within the microfluidic device. In certain embodiments, the method can include configuring a rate of fluid flow from the modulating gas source to be at least five times greater, e.g., at least ten times greater, than a rate of fluid flow of the column effluent into the first and second charging chambers.

In another aspect, a system comprising a microfluidic device comprising an internal microchannel comprising a first charging chamber and a second charging chamber, the first charging chamber and the second charging chamber each fluidically coupled to an inlet port and an outlet port of the microfluidic device, and a switching valve fluidically coupled to the internal microchannel of the microfluidic device and configured to permit flow of a modulating gas through the inlet port and to the first charging chamber in a first position to provide column effluent from the first charging chamber to the outlet port of the microfluidic device and to permit flow of a modulating gas through the inlet port and to the second charging chamber in the second position to provide column effluent from the second charging chamber to the outlet port of the microfluidic device. In some examples, where flow of the modulating gas is permitted to the first chamber, the flow of the modulating gas is restricted to the second chamber (or substantially no flow of modulating gas occurs at all to the second chamber). In certain examples, where flow of the modulating gas is permitted to the second chamber, the flow of the modulating gas is restricted to the first chamber (or substantially no flow of modulating gas occurs at all to the first chamber).

In certain embodiments, the system can include a detector fluidically coupled to the outlet port of the microfluidic device. In some embodiments, the detector is a mass spectrometer. In additional embodiments, the switching valve is a 3-way solenoid valve. In certain examples, the system can include a controller electrically coupled to the mass spectrometer and the switching valve and configured to synchronize detector readings of the mass spectrometer with modulation of the 3-way solenoid valve. In other embodiments, the system can include an injector fluidically coupled to the microfluidic device. In some examples, the microfluidic device can be configured as a laminated wafer.

In an additional aspect, a method comprising selecting a fluid flow rate to be used in a chromatography system, and determining an internal diameter of a column in a chromatography system to provide the selected fluid is provided. In certain examples, the internal diameter of the column is calculated using the following equation $$d_c = \sqrt[4]{\frac{256 \cdot L \cdot p_a \cdot \eta}{b \cdot \pi}}$$

where $d_c$ is the internal diameter of the column, L is column length, $p_a$ is absolute pressure, $\eta$ is viscosity of a carrier gas and b is a constant.

In another aspect, a method comprising selecting a fluid flow rate to be used in a chromatography system, and determining a dimension of a restrictor in a chromatography system to provide the selected fluid flow rate is disclosed. In certain examples, the dimension is an internal diameter of the restrictor and the internal diameter is calculated using the following equation $$d_r = \sqrt[4]{\frac{256 \cdot L \cdot p_a \cdot \eta}{b \cdot \pi}}$$

where $d_r$ is the internal diameter of the restrictor, L is the restrictor length, $p_a$ is absolute pressure, $\eta$ is viscosity of a carrier gas and b is a constant. In certain examples, the dimension is restrictor length and the restrictor length is calculated using the following equation $$L_r = \frac{\left[ \frac{\pi \times T_a \times d_r^4}{256 \times F_a \times p_a} \times (p_i^2 - p_{or}^2) - T_{r2} \times \eta_{r2} \times L_{r2} \right]}{T_{r1} \times \eta_{r1}} + L_{r2}$$

where $L_{r1}$ is the length of the restrictor inside the oven, $L_{r2}$ is the length of the restrictor inside the detector, $\eta_{r1}$ is the viscosity of carrier gas at the oven temperature, $\eta_{r2}$ is the viscosity of carrier gas at the detector temperature, $T_{r1}$ is the absolute temperature of the oven, $T_{r2}$ is the absolute temperature of the detector, $p_i$ is the inlet pressure, $p_{or}$ is the outlet pressure and $F_a$ is the flow rate.

In another aspect, a method of facilitating use of a chromatography system, the method comprising providing a microfluidic device comprising a laminated substrate comprising a plurality of ports each connected to the other in series through an internal microfluidic channel is disclosed.

In an additional aspect, a method of facilitating use of a chromatography system, the method comprising providing a microfluidic device comprising a laminated substrate comprising at least one inlet port and a plurality of outlet ports each fluidically coupled to the inlet port through a microchannel in the laminated substrate, and an internal bypass restrictor in the laminated substrate, the internal bypass restrictor fluidically coupled to the microchannel and configured to restrict fluid flow in the microchannel is provided. In certain embodiments, the plurality of the outlet ports can be arranged in series.

Additional features, aspects, examples and embodiments are described in more detail below.

BRIEF DESCRIPTION OF THE FIGURES

Certain illustrative embodiments are described in detail below with reference to the accompanying figures in which:

FIGS. 3A-3C show a user interface that can be used in a chromatography system to implement flow control, in accordance with certain examples;

FIG. 16 is a schematic of a chromatography system that includes a single detector fluidically coupled to a microfluidic device, in accordance with certain examples;

FIG. 17 is a schematic of a chromatography system that includes two detectors each fluidically coupled to a microfluidic device, in accordance with certain examples;

FIGS. 35A-35C show traces of samples from two different columns (FIGS. 35A and 35B) and modulation of those sample peaks (FIG. 35C), in accordance with certain examples;

FIGS. 36 and 37 are schematics of systems that can be used to perform simultaneous analysis of two chromatograms, in accordance with certain examples;

FIGS. 38 and 39 are schematics of systems configured for multidimensional separations, multiplexed chromatography or multiplexed detection, in accordance with certain examples;

FIG. 40 is a cross-section of a microfluidic device that includes a first charging chamber and a second charging chamber, in accordance with certain examples;

FIG. 41 shows a conventional chromatograph and FIG. 42 shows the prophetic results using modulation and a charging chamber, in accordance with certain examples;

FIGS. 45A and 45B show flow of fluid through a first and second charging chamber using a 3-way switching valve, in accordance with certain examples;

Figure 1B:
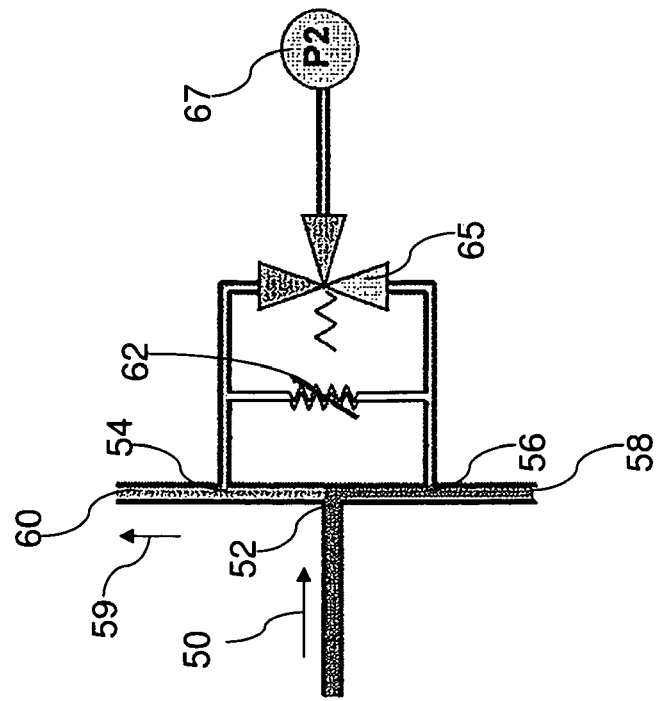
FIGS. 1A and 1B are schematics used to describe the general principles of operation of a microfluidic device, in accordance with certain examples.

It will be understood by the person of ordinary skill in the art, given the benefit of this disclosure, that the exact size and arrangement of the various components shown in the figures can be altered, e.g., enlarged, stretched, reduced, rearranged or otherwise configured differently to provide a desired result or a desired mode of operation. In addition, the particular placement of one component as "upstream" or "downstream" relative to another component may also be altered depending on the desired results or desired methods to be performed using the technology described herein. Unless otherwise noted, fluid flow, e.g., gas flow, is intended to occur generally from left to right in the figures, though other flow directions are possible depending on the exact configuration and pressures used, as described in more detail herein. Where possible arrows may be used in certain instances to show the general direction of fluid flow.

DETAILED DESCRIPTION

The following description is intended to demonstrate some of the useful, novel and non-obvious subject matter provided by the technology described herein. Such description is not intended to be limiting but rather illustrative of the many configurations, embodiments and uses of the chromatography systems described herein and the components and uses thereof. The exact shape, size and other dimensions of the components shown in the figures can vary depending on the intended use of the device, the desired form factor and other factors that will be selected by the person of ordinary skill in the art, given the benefit of this disclosure.

In certain embodiments, the devices, methods and systems described herein can be used in fluid chromatography systems. Fluid chromatography systems are intended to include, but not be limited to, gas chromatography systems, liquid chromatography (LC) systems, supercritical fluid (SCF) chromatography systems and combinations of these illustrative fluid chromatography systems. Certain specific examples are described below with particular reference to gas chromatography (GC) systems, but similar principles and configurations may be used with fluid chromatography systems other than GC systems.

In the systems disclosed herein and illustrated in the figures, the general term "detector" is often used. The detector may be any commonly used GC, LC or SCF detector including, but not limited to, a flame ionization detector (FID), a flame photometric detector (FPD), a thermal conductivity detector (TCD), a thermionic detector (TID), an electron-capture detector (ECD), an atomic emission detector (AED), a photoionization detector (PI), an electrochemical detector, a fluorescence detector, a UV/Visible detector, an infrared detector, a nuclear magnetic resonance detector or other detectors commonly used with GC, LC or SCF. In addition, the detector may be a mass spectrometer, an external detector such as, for example, a discharge ionization detector (DID) or a sulfur chemiluminescence detector (SCD) or other suitable detectors and devices that can be hyphenated to a gas chromatography device or other fluid chromatography devices, e.g., those using capillary columns.

In certain embodiments, the terms "microfluidic device," "switch," or "microfluidic device" are used interchangeably herein. Microfluidic devices are described in many different instances and are typically configured to provide fluid flow from at least one inlet port to one or more outlet ports. The microfluidic devices may also be configured to provide fluid flow to two or more devices that can be fluidically coupled to outlet ports of the microfluidic device. The microfluidic device can take many different forms such as, for example, a laminated wafer including a plurality of layers that when assembled provide one or more internal microfluidic channels. "Fluidically coupled" is used herein to refer to the case where fluid can flow between two or more components. Fluid flow can be permitted between the components by, for example, switching or opening a valve between the components, whereas fluid flow can be restricted between the components, for example, by switching or closing the valve. Where two or more components are fluidically coupled, fluid is not necessarily flowing between them at all times. Instead, depending on the other components of the system and their operational state, fluid can flow between the two fluidically coupled components under certain configurations and arrangements. In the case of a switching valve positioned between two components, for example, the two components can remain fluidically coupled when the valve is in the closed position even though no fluid is flowing between the components.

In certain embodiments, the flow control algorithms and methods described herein are applicable to restrictors, columns, transfer lines or other tubing such as, for example, capillary tubing. For example, the diameters and lengths of the restrictors, columns, transfer lines, etc. can be determined using the algorithms, and the description provided herein that is directed to a particular device, e.g., a restrictor, may be applied to a different device, e.g., a column, of the system.

In certain examples, the components described herein can be connected to each other through tubing, fittings, ferrules or other devices that can provide for substantially fluid tight seals and can provide a fluid flow path between two or more selected components. The lengths, diameters and other parameters for such additional components can be determined based on experimentation or using the length and diameter calculations described herein.

In certain examples, the devices and system described herein can be used in many different types of chromatography systems. It is desirable that the devices be configured for use in either heartcut or solvent dump systems. In heartcut systems, selected species or peaks in the sample may be sent to two or more different columns or detectors. Heartcut systems may be particularly advantageous where poor resolution of two peaks is achieved. Those peaks can be sent to a different column having a different separation media or mechanism. For example, a first conventional column of 30 meters length with an internal diameter of 0.25 or 0.32 mm can be used to provide a first separation stage. A selected portion of the column effluent can then be passed to a second column having a different stationary phase, length, internal diameter or other characteristics that can be used to separate components in that portion of the first column effluent. In a solvent dump system, the amount of solvent sent to a detector may be reduced. For example, it may be desirable to reduce the solvent volume sent to a detector such as a mass spectrometer. A crude separation can first be performed on a first column, e.g., a large internal diameter, low resolution column. Only the components of interest can be sent to a second column, which can be a higher resolution column. To account for difference in pressure, one or more restrictors may be used in the system. For example, there is little pressure differential across a large internal diameter column, and pressures needed to direct the reverse flow across an orifice can cause a large reduction in the flow through the first column. To reduce this effect, a restrictor can be used to increase the overall pressure in the system. Use of restrictors and their effects on pressure are described in more detail herein.

In certain examples, the devices, systems and methods described herein can include a microfluidic device. The microfluidic device can be configured to split flow from a column, to switch the flow between two or more outlet ports or to provide fluid flow to other ports or in other directions. Certain specific configurations of a microfluidic device are described below. These configurations are merely illustrative and other suitable configurations are possible. In certain embodiments, the microfluidic devices described herein are operative to direct gas flow using differential pressures from external gas supplies or pressure regulators. These differential pressures can be used to change the direction of gas flow eluting from a chromatography column between two or more outlet ports. Such operation can have advantages over traditional mechanical-based valve systems including, for example, input and output flow rates are undisturbed resulting in no or little alteration of retention times, the devices can be fabricated from low thermal mass components to avoid or reduce the likelihood of cold spots, there are no moving parts (or few moving parts where one or more valves are present), the internal volumes of the channels in the switch can be minimal to reduce peak dispersion and adsorption effect, the response time is very fast allowing narrow cuts to be switched between outputs which permits it use with modern capillary columns, and internal surfaces can be generally inert and/or deactivated to enable use with labile analytes. Other advantages are also possible depending on the exact configuration of the system.

In accordance with certain examples, the flow rate control described herein may be used by itself or in combination with one or more microfluidic devices. For example, a microfluidic device may be configured as a heartcutting accessory or module that includes one or more microchannels. In other configurations, the microfluidic device can be configured to split effluent from a column between multiple detectors. Other configurations of a microfluidic device will be recognized by the person of ordinary skill in the art, and certain illustrative configurations are described herein.

In certain embodiments, the devices described herein can be used to provide blends of fluids, e.g., gas or liquid blends, that can be used in chromatographic separations or can be used, for example to study gas phase reaction kinetics. For example, two or more different gases can be provided in desired amounts using the flow control algorithms described herein. The gases can be mixed in a microfluidic device (or other device). For example, a first gas can be introduced into a first port of a microfluidic device and a second gas can be introduced into a second port of the microfluidic device. The gases can be mixed, e.g., using an internal buffer, charging chamber or other desired internal channel, and outputted to a reaction chamber, detector or other suitable device. It will be within the ability of the person of ordinary skill in the art, given the benefit of this disclosure, to use the microfluidic devices described herein for these and other uses.

Pressure balanced systems were pioneered by Dr. David Deans of ICI Chemicals in the late 1950s and remain a popular choice in several important GC applications. For example, the PreVent, Protect, MS Vent and Ozone Precursor systems commercially available from PerkinElmer (Waltham, Mass.) all utilize this technique. These techniques are sufficiently powerful that, in many instances, there is no other way of performing a particular analysis or their use makes significant improvements with respect to throughput or quality of the results.

With existing pressure balance systems, there are some drawbacks. It is not possible to directly or explicitly control the flow rate of carrier gas through the column. Many users prefer to specify the flow rate rather than the inlet pressure for carrier gas control through the column. In most instances, this gives more consistent chromatographic performance. It is also not feasible to control the flow rate of carrier gas into the detector. The response of most GC detectors is highly sensitive to gas flow rate and so users would prefer to use flow control to minimize baseline drift and provide consistent analyte response. The applied carrier gas pressures can also be very difficult to set up and requires a substantial amount of understanding on the part of the user. Certain embodiments described herein can permit control of the flow rate through a column by controlling or specifying the carrier gas flow rate through a column.

Figure 1A:
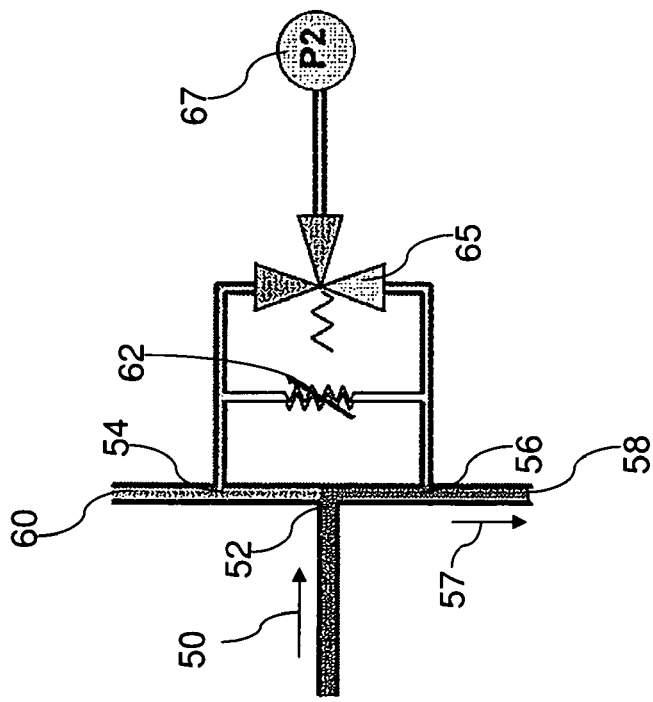

To facilitate a better understanding of the microfluidic devices described herein, a generalized operation principle of a microfluidic device is described in reference to FIGS. 1A and 1B. Referring to FIG. 1A, effluent from a column enters a T-shaped piece at a site or point 52 in the direction of an arrow 50. A switching valve 65, e.g., a solenoid valve, MEMS device or other suitable devices, can be switched to a first position or modulated open to at least some degree to permit carrier gas from the gas source 67 to flow into the T-shaped piece at point 54. The gas pressure provided by the source 67 is at a slightly higher pressure than the gas pressure at point 52. The pressure at point 54 is slightly higher than at points 52 and 56 such that carrier gas will flow from point 54 towards points 52 and 56 and push or direct effluent from the column toward point 56. The effluent will exit the T-shaped piece at port 58 in a direction as shown by an arrow 57 in FIG. 1A. In addition, carrier gas with substantially no effluent from the column will exit the T-shaped piece at port 60. A needle valve 62 at the center of the device is operative to maintain a trickle flow of carrier gas through the unswept gas line so that sample does not diffuse into those areas from point 56.

In certain examples, the switching valve 65 can be switched to a second position such that gas flow in the T-shaped piece is altered or reversed. Referring to FIG. 1B, the switching valve 65 is actuated such that gas flow from the pressure source 67 to the point 56 such that pressure at the point 56 is higher than at points 52 and 54. The effluent from the column will exit the T-shaped piece at port 60 in a direction as shown by an arrow 59 in FIG. 1B. In addition, carrier gas with substantially no effluent from the column will exit the T-shaped piece at port 58. The system shown in FIGS. 1A and 1B is designed to operate when the pressure at points 58 and 60 are substantially the same, e.g., when the pressures are balanced at these points. As described in detail below, the microfluidic devices disclosed herein can be used in such pressure balanced systems to direct the flow of species eluting from a column to a desired port fluidically coupled to a detector, vent, column or other component.

In certain examples where a microfluidic device includes a switching valve, the switching valve may be operative to connect (or disconnect) two or more fluid flow paths such that fluid can flow between the flow paths when connected and fluid flow is restricted when the flow paths are disconnected. Illustrative switching valves include, but are not limited to, a valve such as, for example, a flow control valve, a solenoid valve or a photovac valve, MEMS devices, metal laminated constructs with a laminated membrane operative to open and close a channel underneath it, electromechanical valves, pneumatically operated membrane valves, motor operated needle valves and other suitable devices that can restrict flow in one state and permit flow in another state. In certain examples, the switching valve can be integrated into the microfluidic devices disclosed herein, whereas in other examples, the switching valve may be separate from the microfluidic device. For example, where the microfluidic device is placed in an oven, the switching valve can be placed external to the oven and coupled to the microfluidic device through suitable supply lines and/or tubing. Such external placement can be particularly desirable where the high oven temperatures can adversely affect performance of the switching valve. In some examples, the switching valve can be surface mounted to an external surface of the oven so that the length of any tubing between the switching valve and the microfluidic device can be reduced.

In certain embodiments, the microfluidic devices described herein may include, or be configured as, a wafer, a laminate or other suitably configured device that can provide one or more fluid flow paths from an inlet to two or more potential outlets. The device can be configured to provide flow control of species within a column, detector or other portions fluidically coupled to the device. For example, the microfluidic device may be configured with one or more microchannels to provide for switching or selective flow of gas within a system. Illustrative such systems and devices are described in more detail below. Such microfluidic devices can also permit the control of carrier gas flow through a separation column to simplify the overall setup and use of an instrument by an end-user. These and other features and configurations are described by way of illustration using gas chromatography systems and reference to certain specific embodiments.

In a typical capillary column setup, gas flows from the injector in other ways than just out into the column itself. These pathways include, but are not limited to, splitters, septum purge and an occasional minor leak. Because of these other pathways, regulating the rate of carrier gas flow into the injector does not normally control the actual rate of flow through the column itself. To circumvent this difficulty, most GCs actually control the carrier gas pressure and not explicitly the flow rate. The pressure is applied to deliver the set flow rate according to the Hagen-Poiseuille relationship shown in Equation 1

$$F_o = \frac{\pi \times d_c^4 \times (p_i^2 - p_0^2)}{256 \times L \times \eta \times p_o} \quad (1)$$

where $F_o$ is the flow rate at the outlet, $d_c$ is the internal diameter of the column, L is the column length, $\eta$ is the viscosity of the carrier gas at the set temperature, $p_i$ is the gas pressure at the inlet and $p_o$ is the gas pressure at the outlet. Using the above equation, a user can enter into the user interface the details of the column geometry (d and L), the carrier gas type (to allow the viscosity to be calculated correctly) and the column outlet pressure ($p_o$—normally set to ambient pressure or vacuum, for MS systems). The GC system will have knowledge of the column temperature (to enable the viscosity to be calculated) and so it can calculate the inlet pressure ($p_i$) needed to deliver a required flow rate.

Once the system is set up and running, the only potential variable is the gas viscosity which changes if the column temperature is increased during an oven temperature program. Using Equation 1, the system can adjust the inlet pressure, $p_i$, to maintain the set carrier gas flow rate. While this approach has been widely adopted for carrier gas flow rate control in many successful GC designs, it is not entirely accurate for use in pressure balanced systems and so an alternative approach to carrier gas control is desirable.

Figure 2:
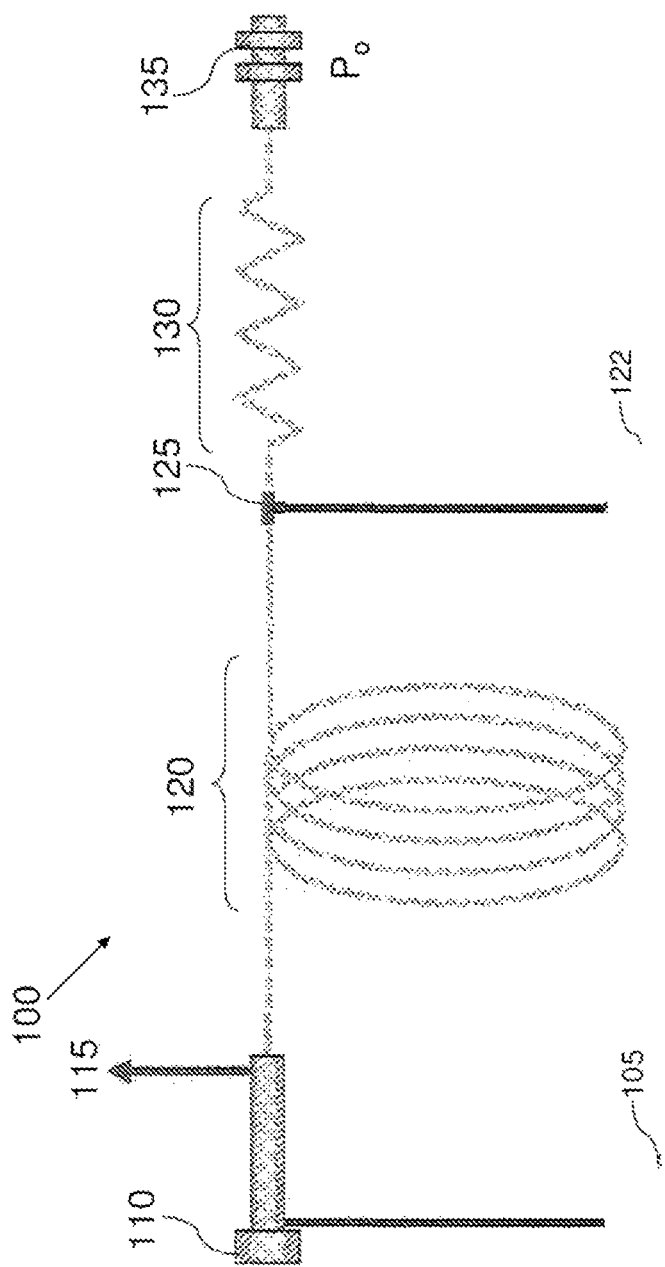
FIG. 2 is an illustration of a chromatography system having a midpoint union, in accordance with certain examples.

In certain examples, a typical pressure balanced system is shown in FIG. 2 such as, for example, a system configured as a single column backflush configuration or a heartcut configuration. The system 100 includes an injector 110 that can provide a split flow in direction 115. A column 120 is fluidically coupled to the injector 110 to receive a carrier gas, from a gas source 105, and any sample that may have been introduced into the system through the injector 110. A pressure balanced system has at least two active components through which a gas is flowing, the column 120 and a restrictor 130.

The flow rate through the column 120 is generally a function of its inlet pressure at the injector ($p_1$) and its outlet pressure at the midpoint pressure ($p_2$) at a midpoint union 125, whereas the flow rate through the restrictor 130 into the detector 135 is controlled by its inlet pressure at the midpoint $p_2$ and its outlet pressure at the detector ($p_o$). These two flow rates are not necessarily the same (in fact in most applications, they are desirably different) and may be independently controlled by varying combinations of the pressures $p_1$ and $p_2$ using independent gas sources 105 and 122.

The flow rates of carrier gas through the column 120 and the restrictor 130 may each still be calculated using Equation 1—they just have differing inlet and outlet pressures. To provide carrier gas flow control within just the column 120, the pressure at the midpoint as the exit pressure can be used.

Figures 3A, 3B, 3C:
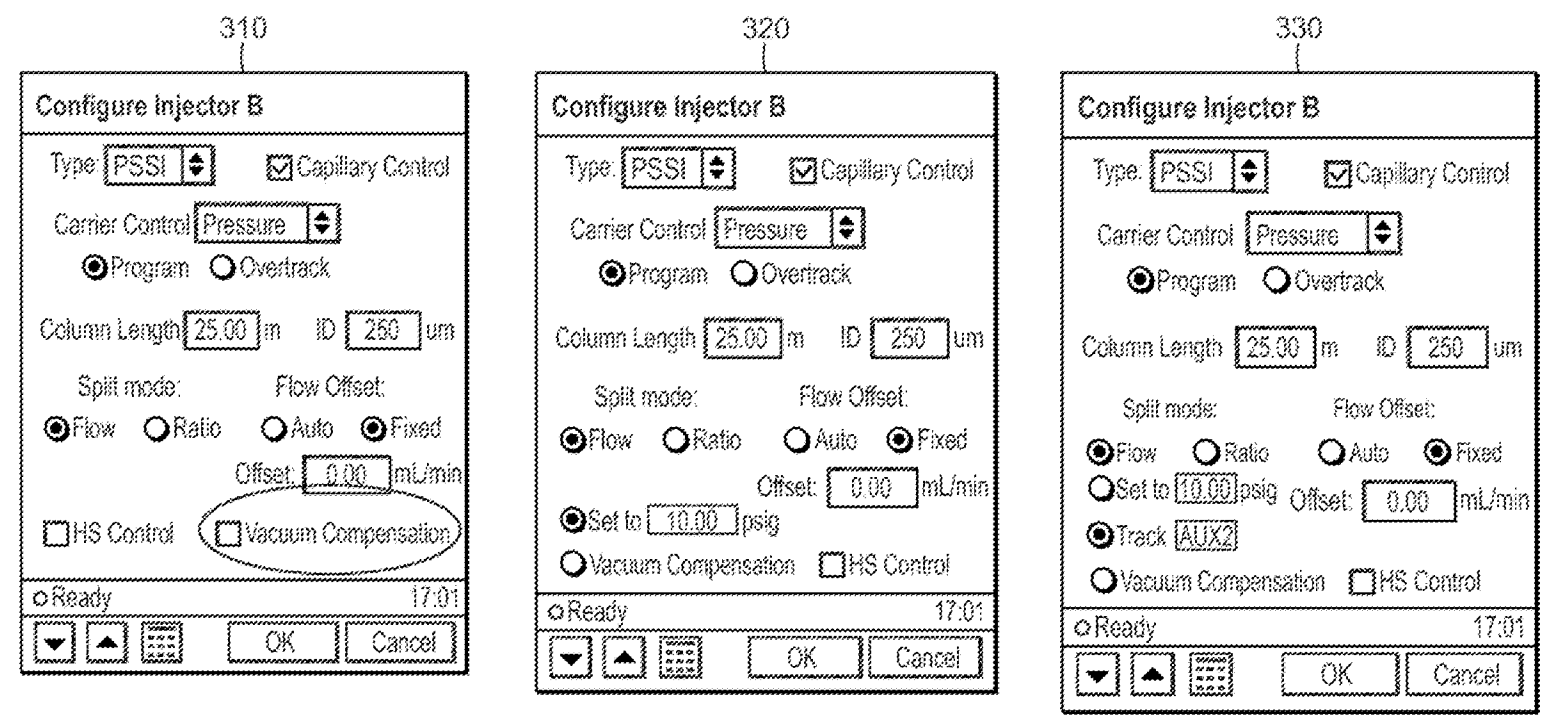

In certain examples and referring to FIG. 3A, a graphical user interface screen 310 of a Clarus GC is shown. Currently, the column exit pressure can only be set to ambient (implied if vacuum not selected) or vacuum (for MS, for example). To enable flow control of the column when fitted to a pressure balance system, it would be desirable for the user to have the ability to enter the outlet pressure, for example, as shown in screen 320 in FIG. 3B or in screen 330 in FIG. 3C. Such modification permits a user to explicitly control the flow rate through a GC column in a pressure balanced system to provide a constant gas flow through a column during temperature programmed chromatography.

In certain examples, flow control through both a column and a restrictor may be performed using the devices and methods described herein. To control the flow through the restrictor, its dimensions and its outlet pressure (ambient or vacuum) should be known or measurable. The remainder of the information will be the same as that for the column. The flow rate can be controlled by setting the restrictor inlet pressure (e.g., the midpoint pressure) according to Equation 1. In some examples, a PPC pressure module such as, for example, those used in a PerkinElmer PreVent system can be used as a carrier supply (with flow rate control algorithms) rather than just a passive pressure regulator. Once the midpoint PPC module is configured, the injector pressure, e.g., the column inlet pressure, would be set to deliver the set flow rate using the PPC midpoint pressure setting for the outlet pressure in Equation 1. The whole process can automatically track an oven temperature program if the column outlet pressure is to be dynamically linked to the midpoint pressure as shown in FIG. 3C. This approach can provide independent control of the gas flows through both the column and the restrictor to provide constant gas flow through the column during temperature programmed chromatography and constant gas flow into the detector. Independent and explicit control of the two gas flows also provides for a more user friendly setup and operation of a pressure balanced system.

Figure 4A:
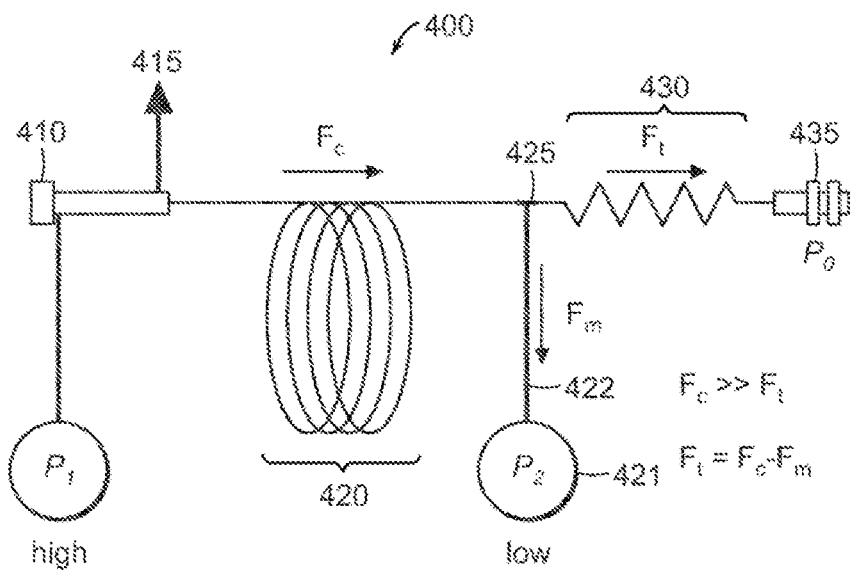
FIGS. 4A-4E are diagrams showing fluid flow in the system under various conditions, in accordance with certain examples.

In accordance with certain examples, to consider some of the improvements flow control can provide, a configuration for pressure balancing is shown in FIG. 4A. Adjustment of the midpoint pressure affects the respective flow rates in the column and restrictor in opposite ways. An increase in the midpoint pressure reduces the flow rate through the column but increases the flow rate through the restrictor. Reducing this pressure has an opposite effect on both flows. Referring to FIG. 4A, a pressure balancing system 400 is shown which includes an injector 410 that has a split flow at point 415, a column 420 fluidically coupled to the injector 410, a midpoint union 425 in a flow path to a restrictor 430, which itself is fluidically coupled to a detector 435. With the midpoint pressure set very low such that $p_2$ is less than $p_1$ the flow rate $F_c$ through the column will be higher than the flow rate $F_t$ through the restrictor and so flow of gas will not occur from the midpoint union 425 as shown in FIG. 4A. Instead, gas flowing from the column 420 will flow up the midpoint supply line 422 at a flow rate of $F_m$ causing loss of sample and potential contamination of the pneumatics system.

Figure 4B:
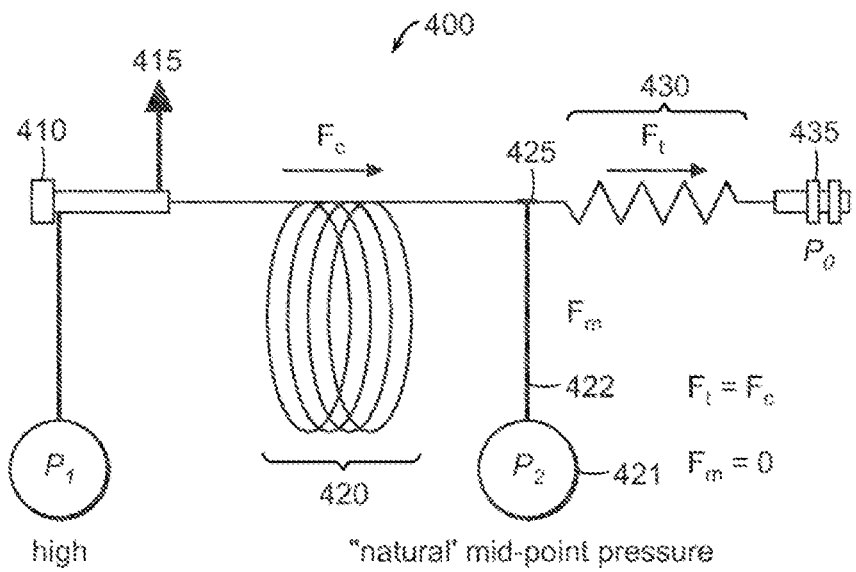

In certain examples and referring to FIG. 4B, where the flow rates through the column $F_c$ and the restrictor $F_t$ are the same, then there is substantially no flow to or from the midpoint union 425, e.g., $F_m$ is about zero. Under the situation shown schematically in FIG. 4B, the mid-point pressure is referred to as the natural mid-point pressure and the system can be considered as pressure balanced. This pressure balancing state can serve as a baseline for the pressure settings.

Figure 4C:
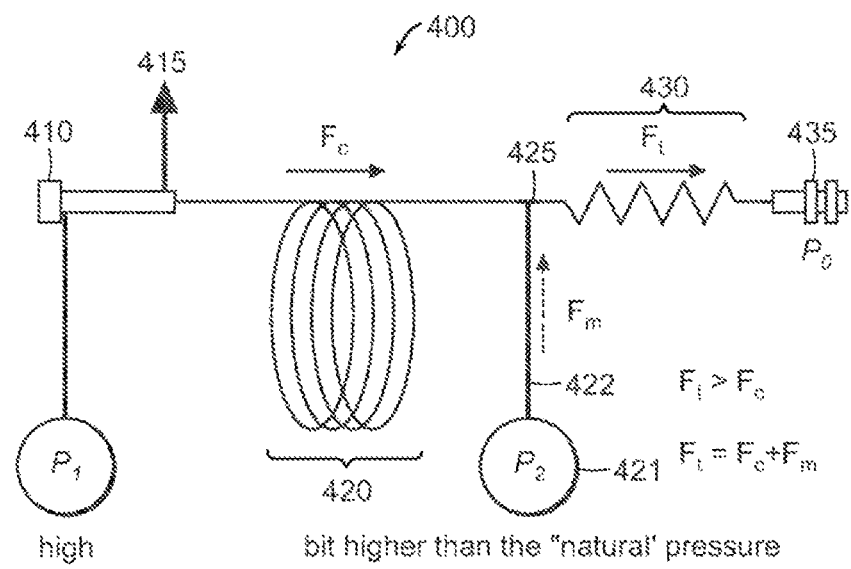
Figure 4D:
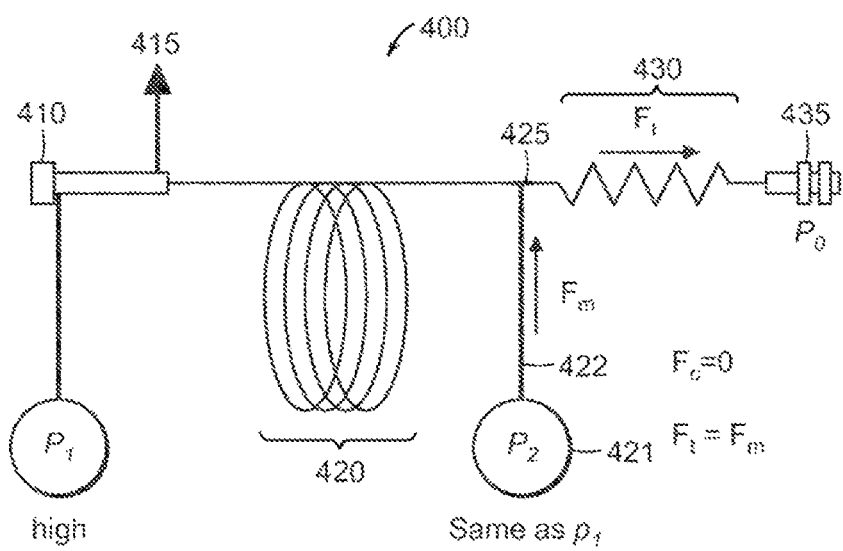

In certain embodiments and referring to FIG. 4C, where the flow rate $F_c$ through the column is less than the flow rate $F_t$ through the restrictor, for example, by increasing the flow rate $F_m$ at the midpoint union 425, gas will flow through the midpoint regulator 421 into the midpoint union 425 and mix with the column effluent going into the restrictor 430 and the detector 435. As the midpoint pressure is progressively increased, the flow rate of gas from the column will steadily decrease until a point is reached where the midpoint pressure is the same as the injector pressure (see FIG. 4D). The flow rate $F_c$ through the column will become zero and any chromatography would stop. Under these conditions, gas flow into the detector 435 is still being maintained solely by the midpoint regulator 421.

Figure 4E:
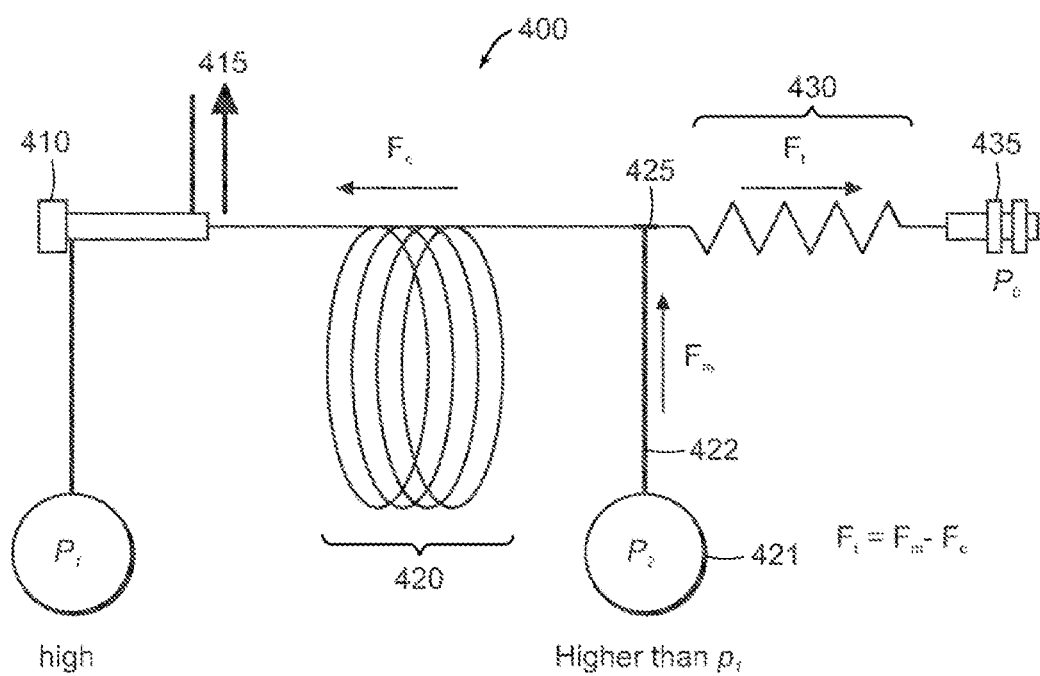

In certain examples and referring to FIG. 4E, if the midpoint pressure is raised above that of the injector such that $p_2$ is greater than $p_1$, then the flow of gas $F_c$ through the column is reversed and may exit the system at the split point 415. This situation is not particularly advantageous for chromatographic separations, but it may be used for backflushing. For example, heavy samples or samples that are difficult to elute from the column can be driven from a column with backflushing after the species of interest have eluted from the column.

Figure 5:
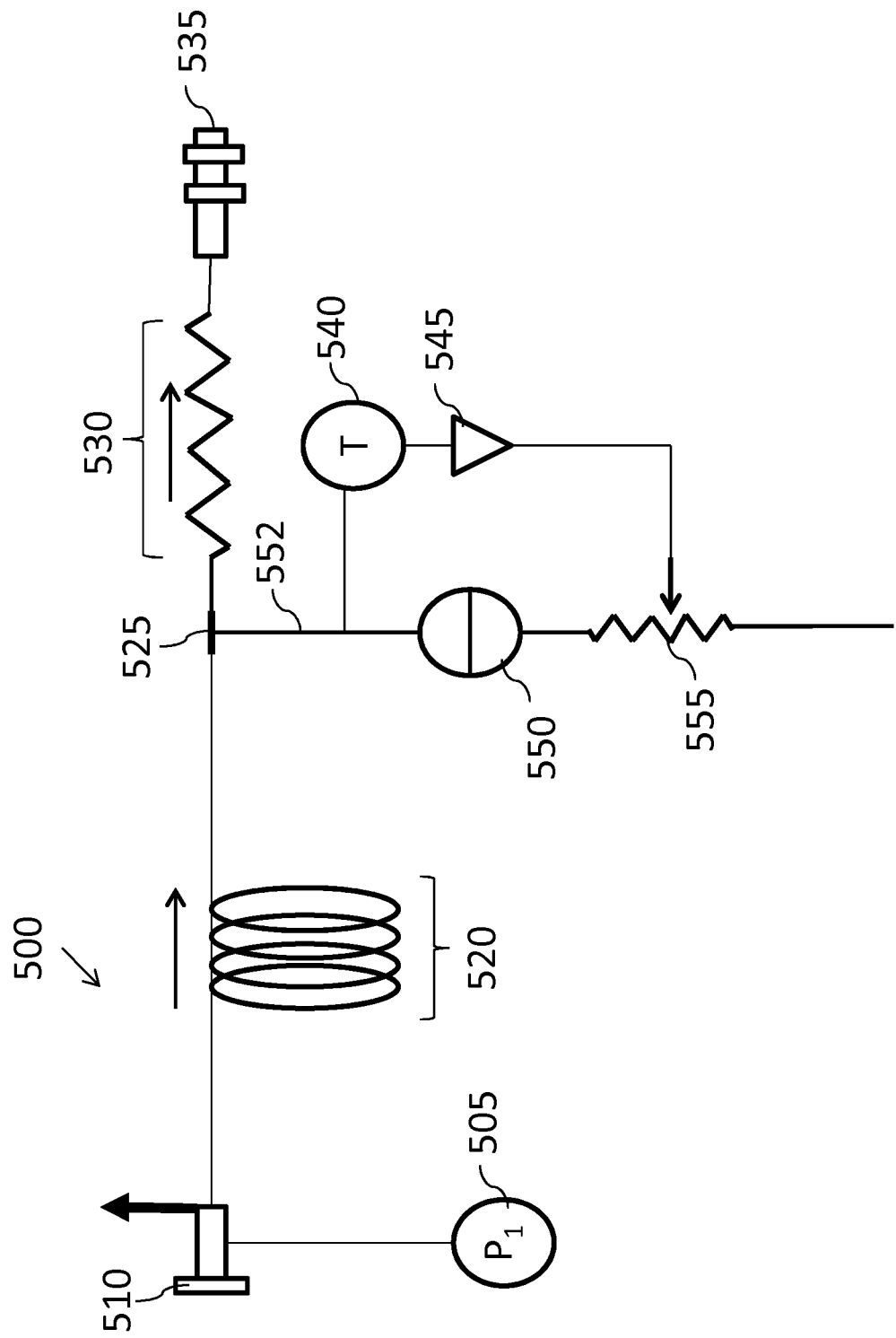
FIG. 5 is a chromatography system that includes a pneumatic controller, in accordance with certain examples.

In accordance with certain examples, the natural midpoint of the system can be advantageously used in the methods and configurations disclosed herein. As discussed herein, the natural midpoint represents the threshold between losing sample and diluting the midpoint and so its determination can increase the overall accuracy of the methods and devices described herein. To determine the natural midpoint, a system such as that shown in FIG. 5 can be used. The system 500 includes an injector 510 fluidically coupled to a column 520 and a carrier gas source 505. A midpoint union 525 is between the column 520 and a restrictor 530. The system 500 also includes a pressure transducer 540, a switching valve 550, and a proportional valve 555 each electrically coupled to a controller 545. During normal operation, the pressure transducer 540 can monitor the gas pressure of the gas as it flows in the system. The internal controller 545 uses this information to adjust the proportional valve 555 positioned upstream of the pressure transducer 540. In this way, closed-loop control can maintain the pressure at a set value.

To establish the natural midpoint pressure, the switching valve 550 is actuated so there is no flow into or out of the midpoint union 525 (assuming that there are no leaks). The flow rates through the column 520 and the restrictor 530 will now be substantially the same. As gas flows through the column 520 and out through the restrictor 530, the pressure at the midpoint will eventually reach a stable value—the natural midpoint pressure. The flow through the column 520 can be calculated using Equation 1 or estimated from tables. If the flow needs to be adjusted, the inlet pressure $p_1$ can be changed, the midpoint pressure is given time to stabilize and the calculation repeated until the desired flow rate is obtained.

Once the correct flow rate has been established and the corresponding natural midpoint pressure is known, then the switching valve 550 can be actuated to permit flow of gas and the midpoint pressure can be set to 1 or 2 psi above the natural midpoint pressure. This slight increase in the set pressure over the natural pressure provides a positive flow of gas from the midpoint regulator to prevent sample from diffusing into the supply line 552. It also serves to maintain the pressure balance as the oven temperature changes. Setting up a pressure balanced system in the traditional way using differential pressure control is a long tedious process which tends to put many potential users off or cause difficulties in the setup and subsequent performance.

Figure 6:
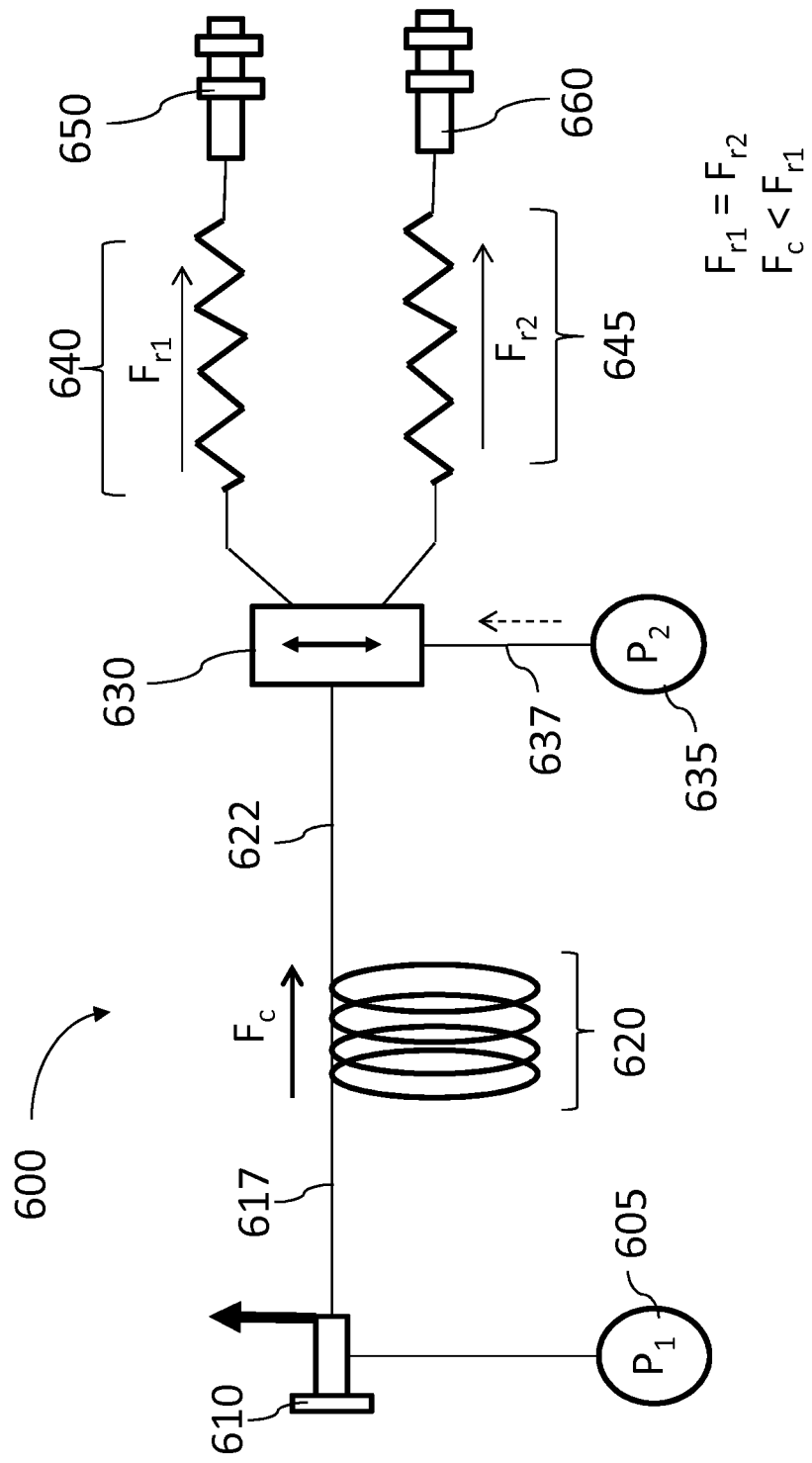
FIG. 6 is a chromatography system that includes a switching valve and two detectors, in accordance with certain examples.
Figure 7:
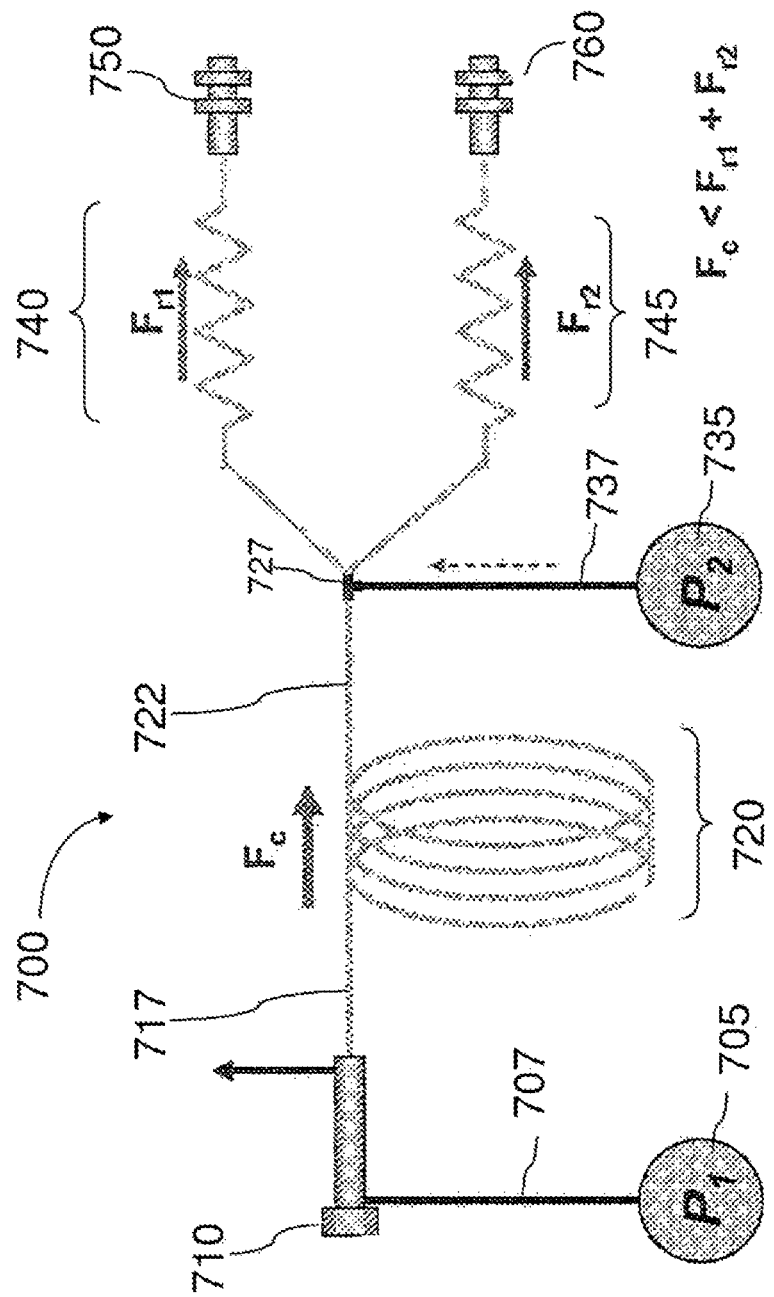
FIG. 7 is a chromatography system that includes two detectors and a splitter, in accordance with certain examples.

In certain embodiments, with explicit control of the flow rate in the column and the restrictor, system setup is greatly simplified and overall accuracy and precision can be increased. The system can be configured such that the flow rate through the restrictor is less than the flow rate through the column to ensure correct operation. The system user needs only to enter the respective flow rates in the analytical method and the differential flow control can preserve the correct balance between the column and the restrictor and provide a constant flow rate of gas through the column and into the detector. This approach can be used in the simple situation of single column backflushing as described earlier but also with heartcutting and splitting as shown in FIGS. 6 and 7. Referring to FIG. 6 where a heartcut configuration is shown, the system 600 includes an injector 610 fluidically coupled to a pressure regulator 605 through a supply line 607. The injector 610 is fluidically coupled to a column 620 through a supply line 617. The column 620 is fluidically coupled to a microfluidic device 630 through a supply line 622. The microfluidic device 630 is fluidically coupled to a midpoint pressure regulator 635 through a supply line 637. Detectors 650 and 660 are fluidically coupled to the microfluidic device 630 through restrictors 640 and 645, respectively. The restrictors 640 and 645 are desirably matched or substantially the same such that the flow rate Fr1 through the restrictor 640 is substantially the same as the flow rate Fr2 through the restrictor 645. Methods of determining restrictor lengths and diameters to provide a desired flow rate are described herein.

Figure 8A:
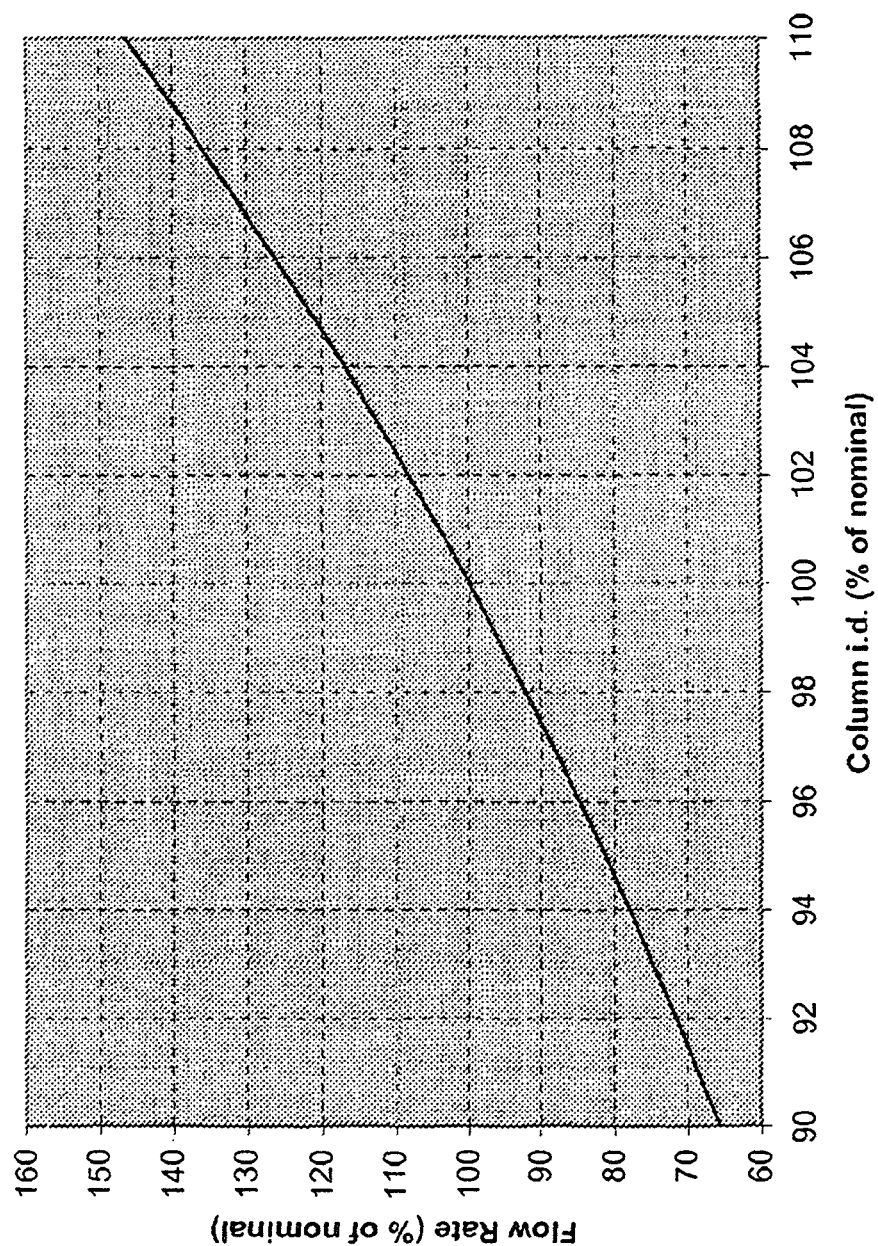
FIG. 8A is graph showing the change in flow rate as a function of the error in column internal diameter, in accordance with certain examples.
Figure 8B:
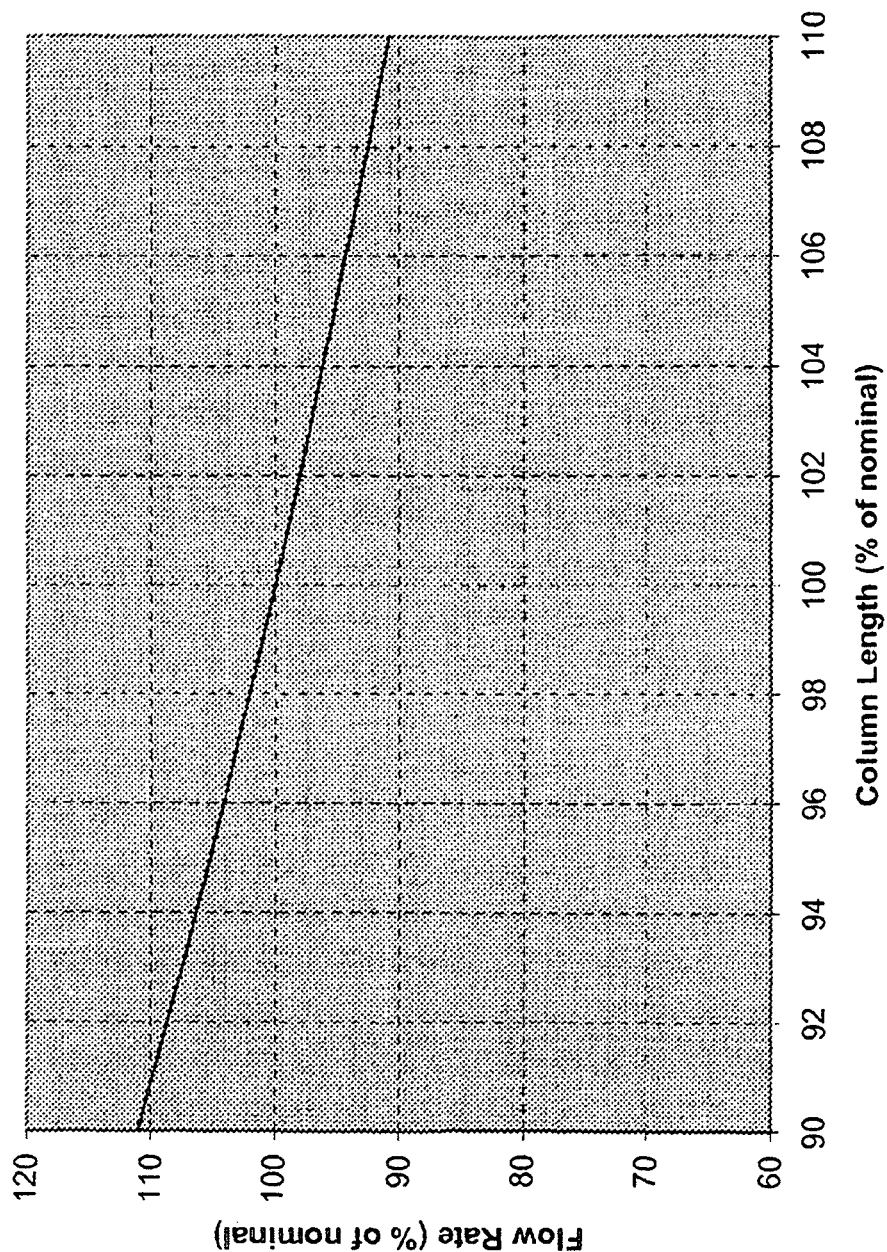
FIG. 8B is a graph showing the change in flow rate as a function of the error in column length, in accordance with certain examples.

In certain examples and referring to FIG. 7, a pressure regulated splitter system is shown. The system 700 includes an injector 710 fluidically coupled to a pressure regulator 705 through a supply line 707. The injector 710 is fluidically coupled to a column 720 through a supply line 717. The column 720 is fluidically coupled to a midpoint pressure regulator 735 through supply lines 722 and 737 at a union or split 727. Detectors 750 and 760 are fluidically coupled to the midpoint pressure regulator 735, through the union or split 727, through resistors 740 and 745, respectively. In operation of the system 700, the flow rate can be set for one of the restrictors 740 and 745, and the other restrictor can be displayed and maintained but not controlled independently of the other restrictor. The actual flow rate in both the column and the restrictor can be determined using Equation 1 for the calculations. The length of the column and its diameter may be inputted by the users, based on the column specifications provided by the column supplier. From Equation 1, the column flow rate has a fourth order dependence on column diameter. Thus, an error in diameter of the column can lead to a large error as shown prophetically in the graph of FIG. 8A. As shown in FIG. 8A, an error of just 2% in the internal column diameter, e.g., 5 microns on a 250 micron inner diameter column, is enough to cause an inaccuracy of almost 8% in the applied flow rate. With respect to column length, there is a reciprocal relationship between column length between flow and column length as shown in FIG. 8B. In this case, an error of 2% in column length, e.g., about a 60 centimeter error on a 30 meter column, will produce about a 2% error in the calculated flow rate. This error can lead, however, to additional errors in the flow rate assumptions.

In certain examples, one solution to any potential inaccuracy is to consider the provision of a geometric factor (GF) that can be applied to a particular column. The GF can be approximated using Equation 2.

$$GF = \frac{d_c^4}{L} \quad (2)$$

The GF is constant for any given column and should be simple to establish by simple experiment (by either the supplier or the end user). Because this measurement is empirical, it will apply directly to a given column without making any assumptions about its geometry. Inserting the geometric factor in Equation 1 provides Equation 3.

$$F_o = \frac{\pi \times GF \times (p_i^2 - p_o^2)}{256 \times \eta \times p_o} \quad (3)$$

To calculate the flow rates, the inlet ($p_i$) and outlet ($p_o$) pressures and the temperature to calculate the viscosity must be entered or known. In a typical configuration, these parameters are known by the controller or entered by the user.

In accordance with certain examples, the situation with restrictor flow rate control is similar to that of the column. The restrictor is generally much shorter than the column and so it is much easier to measure its length. The internal diameter is normally much smaller and so small errors in its measurement will have a much greater impact on this flow rate of gas passing through it. The application of a GF for the restrictor is therefore just as desirable as it is for the column. One other aspect of the restrictor that can be considered is that part of it (or possibly most of it in the case of an MS) will reside inside the body of the detector. Thus, different sections of the restrictor will be at different temperatures and so Equations 1 and 3 may not be entirely accurate. This aspect can be addressed by using an approach taken to calculate flow rates through a serially connected transfer line and column for the TurboMatrix thermal desorption systems as given in Equation 4 and as described, for example, in commonly assigned U.S. Pat. Nos. 7,219,532 and 7,468,095, the entire disclosure of each of which is hereby incorporated herein by reference in its entirety.

$$F_o = \frac{\pi \times Tr}{256 \times p_o} \times \frac{(p_i^2 - p_o^2)}{\left(\frac{T_c \times \eta_c}{GF_c}\right) + \left(\frac{T_r \times \eta_r}{GF_r}\right)} \quad (4)$$

In equation (4), $F_o$ is the flow rate at the restrictor outlet (at the temperature and pressure at that location), $GF_c$ is the column geometric factor, $GF_r$ is the restrictor geometric factor, $d_c$ is the column internal diameter and $L_c$ is the column length (for determining $GF_c$), $d_r$ is the transfer line internal diameter and $L_r$ is the length of the transfer line (for determining $GF_r$), $\eta_c$ is the viscosity of the carrier gas in the column, $\eta_r$ is the viscosity of the carrier gas within the restrictor, $T_c$ is the absolute temperature of the column, $T_r$ is the absolute temperature of the transfer line, $p_i$ is the absolute pressure of the carrier gas at the column inlet and $p_o$ is the absolute pressure of the carrier gas at the restrictor outlet. Equation 4 can be used in place of Equation 3 to provide a more accurate calculation of the flow rate.

Figure 9A:
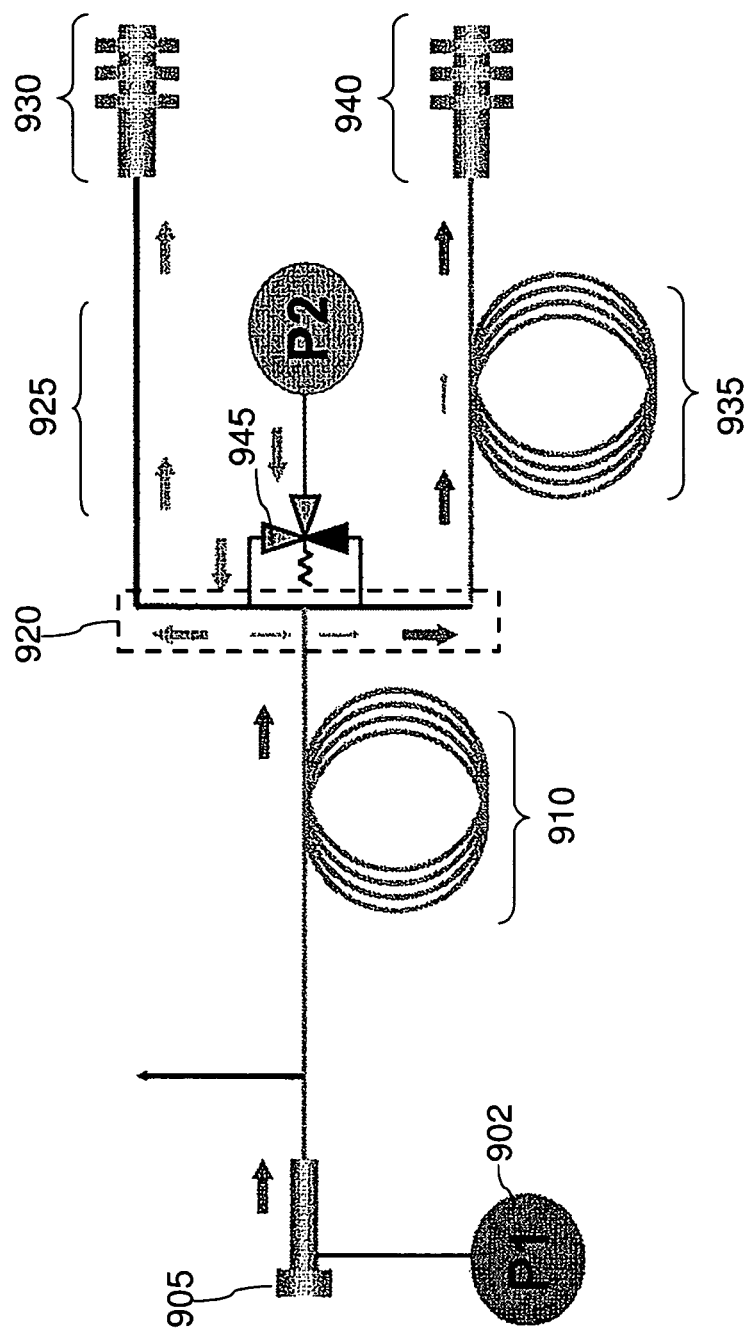
FIGS. 9A and 9B are illustrations of chromatography systems including a microfluidic device and a switching valve, in accordance with certain examples.

In certain examples, the length of a restrictor of a selected internal diameter can be calculated based on the desired flow rate through a column of specified geometry. Such dimensions can depend, at least in part, on the temperatures and gas pressures desired in the system. One configuration of a system with a restrictor is shown in FIG. 9A. The system of FIG. 9A includes a split injector 905 fluidically coupled to a first column 910 and a carrier gas source 902. A microfluidic device 920 is fluidically coupled to the first column 910 and is configured to direct species eluting from the first column 910 to a desired component. For example, column effluent can be directed to a first detector 930 through a restrictor 925, or column effluent can be directed to a second column 935 and onto a second detector 940 using the microfluidic device 920 and a switching valve 945.

In certain examples, the dimensions and geometry of the restrictor 925 can be selected to further balance the pressures in the system. A typical restrictor includes a piece of deactivated fused silica tubing of known internal diameter that can be cut to a length calculated to provide substantially the same flow rate of gas the through the column under a particular applied pressure and temperature. The length of the restrictor can be determined by trial and error, where the length of the restrictor is progressively shortened until the correct flow rate is achieved. However, this process is cumbersome and can take a substantial amount of time to determine the proper restrictor length. Incremental shortening of the restrictor may also not take into account the downstream effects of detector temperature on the flow rates through the column and the restrictor, which can have a significant effect on the actual flow rate to cause a pressure imbalance in the system. Where multiple detectors are present and used at different pressures, e.g., an FID (ambient pressure) and a MS detector (vacuum pressure), the pressure imbalancing may be even greater.

In certain embodiments, the restrictor geometry and length can be calculated to match or substantially match the gas flows in a selected column based on oven and detector temperature and detector operating pressure. Current calculations assume that the restrictor is of uniform length and temperature. The flow rate can be calculated according to equation (5)

$$F_a = \frac{\pi \times d_r^4 \times T_a \times (p_i^2 - p_{or}^2)}{256 \times L_r \times p_a \times \eta \times T_r} \quad (5)$$

where $F_a$ is the restrictor outlet flow rate at ambient temperature and pressure, $d_r$ is the internal diameter of the restrictor, $T_a$ is the ambient absolute temperature, $p_i$ is the carrier gas absolute pressure at the restrictor inlet, $p_{or}$ is the carrier gas absolute pressure at the restrictor outlet, $L_r$ is the length of the restrictor, $p_a$ is the ambient absolute pressure, $\eta$ is the viscosity of the carrier gas at the restrictor temperature, and $T_r$ is the restrictor absolute temperature.

To determine the restrictor length to match a desired gas flow in a column, two simultaneous equations based on equation (5) can be used to solve for $L_r$, which provides equation (6)

$$L_r = L_c \times \frac{d_r^4}{d_c^4} \quad (6)$$

where $d_c$ is the internal diameter of the column, and $L_c$ is the length of the column. Equation 6 can be used, for example, where the temperature and the applied inlet and outlet pressures are the same between the column and the restrictor.

Where two or more detectors or a detector and a vent or any two devices operated at different pressure are present, Equation (5) can be used to obtain Equation (7)

$$L_r = L_c \times \frac{d_r^4 \times (p_i^2 - p_{or}^2)}{d_c^4 \times (p_i^2 - p_{oc}^2)} \quad (7)$$

where $p_{oc}$ is the carrier gas absolute pressure at the column outlet.

In certain embodiments, to take into account the effect of detector temperature on the gas flow rates through both the column and the restrictor, the relationship shown in Equation (8a) can be used.

$$F_a = \frac{\pi \times T_a}{256 \times p_a} \times \frac{(p_i^2 - p_o^2)}{\left(\frac{T_t \times \eta_t \times L_t}{d_t^4}\right) + \left(\frac{T_c \times \eta_c \times L_c}{d_c^4}\right)} \quad (8a)$$

In Equation (8a), $F_a$ is the flow rate at the column outlet, $d_c$ is the column internal diameter, $d_t$ is the transfer line (or restrictor) internal diameter, $L_c$ is the column length, $L_t$ is the transfer line (or restrictor) length, $\eta_c$ is the viscosity of the carrier gas within the column, $\eta_t$ is the viscosity of the carrier gas within the transfer line (or restrictor), $T_c$ is the absolute temperature of the column, $T_t$ is the absolute temperature of the transfer line (or restrictor), $T_a$ is the absolute ambient temperature, $p_i$ is the absolute pressure of the carrier gas at the inlet, $p_o$ is the absolute pressure of the carrier gas at the outlet and $p_a$ is the absolute ambient pressure. Equation (8a) can be generalized for any number of serially connected columns or restrictors of differing internal diameter, length or temperature, as shown in Equation 8(b).

$$F_a = \frac{\pi \times T_a}{256 \times p_a} \times \frac{(p_i^2 - p_o^2)}{\left(\frac{T_1 \times \eta_1 \times L_1}{d_{c1}^4}\right) + \left(\frac{T_2 \times \eta_2 \times L_2}{d_{c2}^4}\right) + \cdots \left(\frac{T_n \times \eta_n \times L_n}{d_{cn}^4}\right)} \quad (8b)$$

The column and the restrictor of uniform diameter are in a GC oven and are at a different temperature than a detector. Equation (8a) can be modified for the restrictor and the column to provide Equations (9) and (10) for the restrictor and the column, respectively.

$$F_a = \frac{\pi \times T_a \times d_r^4}{256 \times p_a} \times \frac{(p_i^2 - p_{or}^2)}{T_{r1} \times \eta_{r1} \times L_{r1} + T_{r2} \times \eta_{r2} \times L_{r2}} \quad (9)$$

In Equation (9), $L_{r1}$ is the length of the restrictor inside the oven, $L_{r2}$ is the length of the restrictor inside the detector, $\eta_{r1}$ is the viscosity of carrier gas at the oven temperature, $\eta_{r2}$ is the viscosity of carrier gas at the detector temperature, $T_{r1}$ is the absolute temperature of the oven and $T_{r2}$ is the absolute temperature of the detector.

$$F_a = \frac{\pi \times T_a \times d_c^4}{256 \times p_a} \times \frac{(p_i^2 - p_{oc}^2)}{T_{c1} \times \eta_{c1} \times L_{c1} + T_{c2} \times \eta_{c2} \times L_{c2}} \quad (10)$$

In Equation (10), $L_{c1}$ is the length of the restrictor inside the oven, $L_{c2}$ is the length of the restrictor inside the detector, $\eta_{c1}$ is the viscosity of carrier gas at the oven temperature, $\eta_{c2}$ is the viscosity of carrier gas at the detector temperature, $T_{c1}$ is the absolute temperature of the oven and $T_{c2}$ is the absolute temperature of the detector.

In certain examples, Equation (10) can be used to calculate the pressure to apply to the column to deliver a required flow rate through the column by rearranging it as Equation (11).

$$p_i = \sqrt{\frac{F_a \times 256 \times p_a}{\pi \times T_a \times d_c^4} \times (T_{c1} \times \eta_{c1} \times L_{c1} + T_{c2} \times \eta_{c2} \times L_{c2}) - p_{oc}^2} \quad (11)$$

Once the inlet pressure is calculated for the column at a specific geometry, temperatures and outlet pressure, the length of the restrictor may be calculated using the rearranged form of Equation (9) as shown in Equation (12).

$$L_r = \frac{\left[\frac{\pi \times T_a \times d_r^4}{256 \times F_a \times p_a} \times (p_i^2 - p_{or}^2) - T_{r2} \times \eta_{r2} \times L_{r2}\right]}{T_{r1} \times \eta_{r1}} + L_{r2} \quad (12)$$

Using Equation (12), the length of a restrictor of known internal diameter that can provide a desired flow rate to balance the system can be calculated. In particular, the length of a restrictor of known internal diameter to balance the flow rate in another channel taking into account detector length, temperature and pressure of the other detector can be determined. In use, the algorithms can be implemented in software such that a user can enter a desired flow rate and the restrictor lengths and diameters to provide such desired flow rate, under specified column parameters and temperatures, can be displayed in a user interface to facilitate use of the system.

Certain embodiments described herein include the use of an additional column in the chromatography system. The additional column is used in place of a restrictor and is typically present when heartcutting is desired. Unlike fused silica restrictors, a user is unlikely to cut off pieces of a column to achieve a pressure balance across the microfluidic device. Even if the columns are selected to have the same length and diameter, temperature and pressures differences between two different detectors can disrupt the pressure balancing. When the columns are of a different geometry or length, the pressure imbalance can be even greater.

Figure 9B:
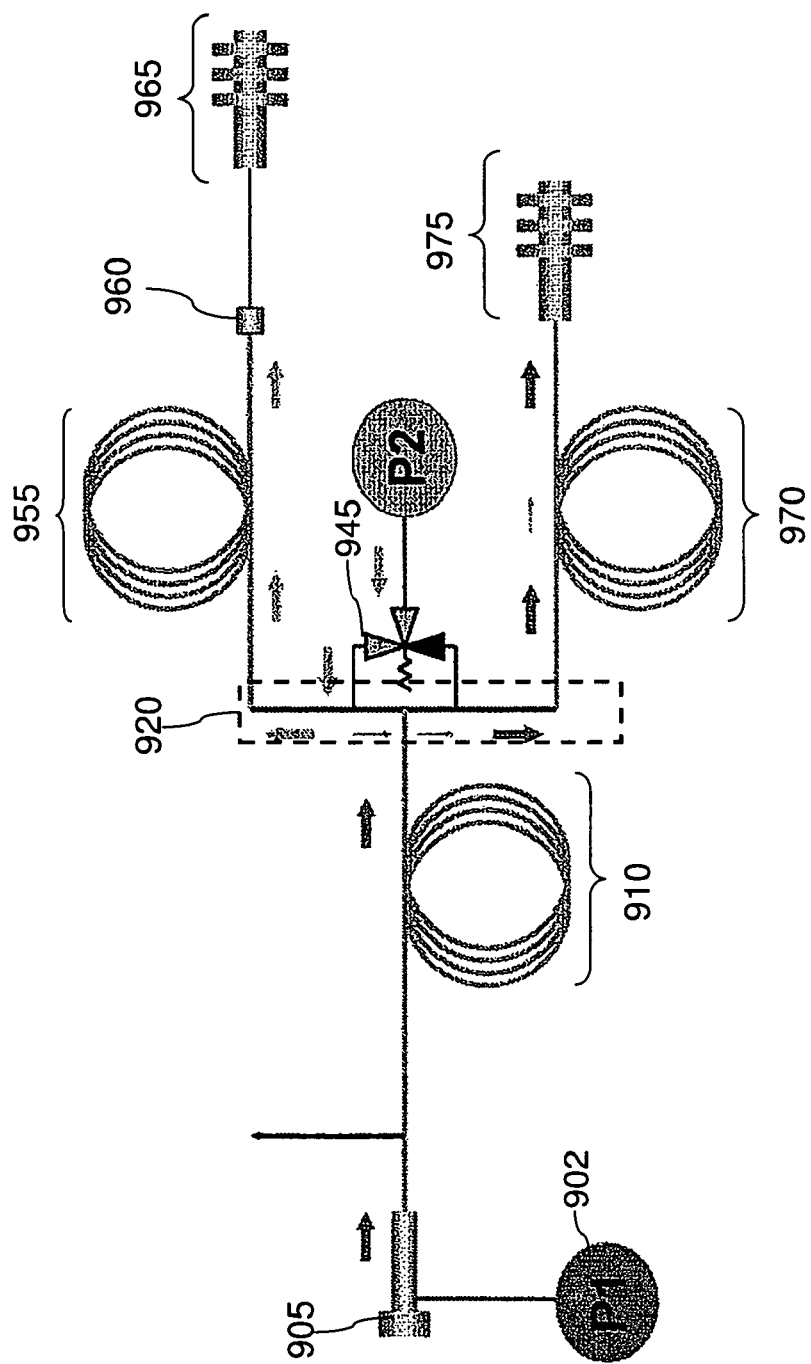

One possible solution when multiple columns are present is to use an inline restrictor with the column having the highest flow rate, as shown schematically in FIG. 9B. The system of FIG. 9B includes a second column 955 fluidically coupled to the first column 910 through the microfluidic device 920. Between a first detector 965 and the second column 955 is a restrictor 960. The system shown in FIG. 9B also includes a third column 970 fluidically coupled to a detector 975. In this configuration, the column 955 has a higher flow rate than the columns 910 and 970. In the configuration shown in FIG. 9B, there are three restrictive zones to consider: the second column 955 at the oven temperature, the restrictor 960 at the oven temperature and the restrictor 960 at the temperature of the first detector 965. Equation (9) can be modified to include these three zones as shown in Equation (13), $$F_a = \frac{\pi \times T_a}{256 \times p_a} \times \frac{(p_i^2 - p_{or}^2)}{\left(\frac{T_{r1} \times \eta_{r1} \times L_{r1} + T_{r2} \times \eta_{r2} \times L_{r2}}{d_r^4}\right) + \left(\frac{T_{c3} \times \eta_{c3} \times L_{c3}}{d_{c3}^4}\right)} \quad (13)$$

where $L_{c3}$ is the length of the column 955, $\eta_{c3}$ is the viscosity of the carrier gas in the column 955 and $T_{c3}$ is the absolute temperature of the column 955. To calculate the length of the restrictor to deliver a desired flow rate, Equation (13) can be rearranged to provide Equation (14)

$$L_r = \frac{\left[d_r^4 \times \left[\frac{\pi \times T_a}{256 \times F_a \times p_a} \times (p_i^2 - p_{or}^2) - \frac{T_{c3} \times \eta_{c3} \times L_{c3}}{d_{c3}^4}\right] - T_{r2} \times \eta_{r2} \times L_{r2}\right]}{T_{r1} \times \eta_{r1}} + L_{r2} \quad (14)$$

In use, Equation (11) can be used to calculate the flow rate through the column without the restrictor. Equation (14) can then be used to calculate the restrictor length to match that flow rate. Also, while not shown, the column 955 can be placed between the restrictor 960 and the first detector 965 and Equations (13) and (14) can be modified based on this rearrangement.

In certain examples, the restrictor internal diameter (or the internal diameter of other tubing or columns) can be selected to provide a desired flow rate. For a number of GC techniques that use a microfluidic device as described herein, it is important to accurately know the internal diameter of columns and tubes. In practice, the manufacturer's description is assumed to be accurate and is adopted. This can lead to significant errors as most relationships involve a calculation based on the 4th-power of the internal diameter. In these instances, knowledge of the true internal diameter would be desirable. Equation (15) can be used to approximate the flow rate $$F_a = \frac{\pi \cdot d_c^4 \cdot T_a \cdot (p_i^2 - p_o^2)}{256 \cdot L \cdot p_a \cdot \eta \cdot T_c} \quad (15)$$

where $F_a$ is the flow rate at the column outlet at ambient temperature and pressure, $d_c$ is the internal diameter of the column, L is the length of the column, $p_i$ is the carrier gas pressure at the column inlet, $p_o$ is the outlet pressure, $p_a$ is the ambient pressure, $T_c$ is the column temperature, $T_a$ is the ambient temperature, and $\eta$ is the viscosity of the carrier gas at the column temperature. For a column or tube at ambient temperature, Equation (15) may be re-arranged to provide Equation (16).

$$F_a = \left[\frac{\pi \cdot d_c^4}{256 \cdot L \cdot p_a \cdot \eta}\right] \cdot [p_i^2] - \left[\frac{\pi \cdot d_c^4 \cdot p_o^2}{256 \cdot L \cdot p_a \cdot \eta}\right] \quad (16)$$

For a given column or tube, the terms inside the large brackets are constant and so Equation (16) may be represented as Equation (17).

$$F_a = b \cdot [p_i^2] - a \quad (17)$$

where a and b are constants. Thus by applying a range of pressures to one end of the column or tube and measuring the flow rate at the other, the value of the constant b can be determined by a least squares statistical fit. Once the value of b is established, the internal diameter may be calculated from Equation (18).

$$d_c = \sqrt[4]{\frac{256 \cdot L \cdot p_a \cdot \eta}{b \cdot \pi}} \quad (18)$$

As shown specifically in Example 1 below, the diameter of the tubing, e.g., columns, restrictors and the like can accurately be determined using these equations. The methods can be implemented in software to provide a calibration protocol where various diameters of tubing, e.g., columns, internal tubing, restrictors, etc. can be determined to provide for increased accuracy of the system. The calibration can be performed by the chromatography system or the user can determine the diameter of the tubing and enter the calculated diameters into the system for use in controlling or modulating the flow rates as described herein.

In certain embodiments, to provide for a more user friendly system, the equations noted above may be implemented in software such that a user can enter the column parameters, e.g., length and internal diameter, the oven temperature and the detector temperature and the system can accurately predict the particular pressures needed to accomplish a desired separation run. The software can calculate the flow rate, restrictor lengths and/or diameters based on the inputted parameters, and the user can then insert a restrictor having the calculated length and diameter at a desired site in the system.

Figure 10:
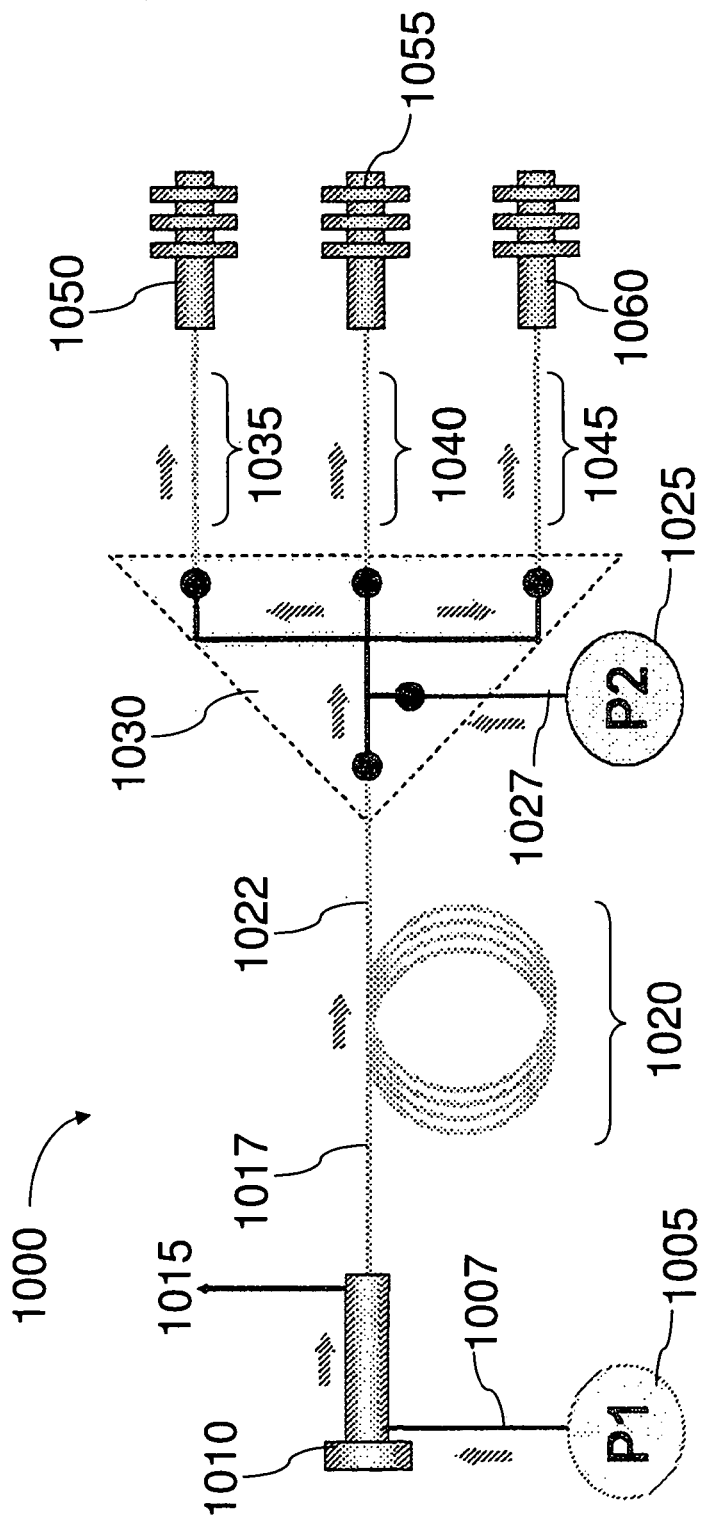
FIG. 10 is an illustration of a chromatography system including three detectors, in accordance with certain examples.

Referring to FIG. 10, an illustrative system including a splitting device, which can be a microfluidic device as described herein, configured to split column effluent to two or more detectors is shown. The system 1000 includes an injector 1010 fluidically coupled to a pressure regulator 1005 through a supply line 1007. The injector 1010 may have a split flow such that a portion of the sample introduced into the injector 1010 is passed to a column 1020 fluidically coupled to the injector 1010 through a supply line 1017 and the rest of the sample is passed along a direction 1015, which may be sent to waste or to another column, for example. The column 1020 is fluidically coupled to a splitting device 1030 through a supply line 1022, which fluidically couples the column 1020 to the splitting device 1030 through an input port on the splitting device 1030. The splitting device 1030 is also fluidically coupled to a midpoint pressure regulator 1025 through a supply line 1027. As shown schematically in FIG. 10, the splitting device 1030 is configured to split effluent flow from the column 1020 into three different flow paths. The splitting device 1030 is fluidically coupled to each of a detector 1050, 1055 and 1060 through a resistor 1035, 1040 and 1045, respectively. During operation of the system 1000, column effluent will enter the input port of the splitting device 1030 and mix with carrier gas supplied from a midpoint pressure regulator 1025. The effluent can then exit through a plurality of output ports of the splitting device to the detectors 1050, 1055 and 1060. While three detectors are shown in FIG. 10, either fewer, e.g., two detectors, or more, e.g., four or more detectors, could be used. It is not necessary to balance the restrictors 1035, 1040 and 1045. The restrictors may take several forms such as any of those described herein. By selecting restrictors of appropriate length and internal diameter, the column effluent may be split between the attached detectors over a large range of ratios. The use of a midpoint pressure regulator 1025 in the system 1000, provides some advantageous features. By having a midpoint gas supply, the flow rate into each detector can be increased according to the needs of each detector thus providing for flexibility in detector flow rates. The low carrier gas flow rates through narrow bore columns can cause even lower flow rates to flow out of the microfluidic device and limit the range of split ratios that could be used. The mid-point regulator can provide additional gas flow to overcome these issues and allow very narrow-bore columns to be used if desired. Column backflushing may also be performed. The midpoint regulator also provides for the ability to protect an active MS detector while changing columns.

In certain examples, the system described herein that includes a microfluidic device can be used in many different configurations. For example, it is possible to simultaneously use selective detectors on the same chromatogram. This feature saves time (only one run needed) and eliminates variations (particularly retention times) between different chromatograms. One example is the TO-14 US-EPA air monitoring method where both an FID and ECD are used to monitor different compounds in the same chromatogram. In other configurations, improved dynamic range can be achieved by splitting different amounts to the same type of detector. Some detectors (e.g. FPD) have a very limited dynamic range and so the ability to see large peaks on one detector and small on the other could be useful. In some examples as described herein, single column backflushing can be performed by controlling the flow rate at various points in the system. This process can save time and eliminate extended temperature programs by efficiently removing heavy sample residue from the column after the analytes have eluted. Dual column backflushing can also be performed. For example, one (or more) of the restrictors shown in the system 1000 could be replaced by a GC column. This configuration would enable the first column to be backflushed while chromatography continues on the second column. A mid-point detector can be configured to monitor the passage of peaks between the two columns to aid setup. Dual column backflushing has a big advantage over single column backflushing in that the backflushing occurs simultaneously with the chromatography run thus achieving a substantial time savings. In the case of air-sensitive detectors, such as an MS or ECD, this system can permit those detectors to remain at a detection temperature, e.g., hot and active, while a column is being exchanged or an injector is serviced. This feature would save significant time and reduce stress on the system and so the down time would be minimized. In addition, three or more column backflushing could also be performed so that chromatography can proceed on one or more other columns while the first (or more than one column) is being backflushed.

In certain examples, the systems described herein can be used for polarity tuning. In this technique, the respective residence time of compounds within the two columns can be modified by changing the midpoint pressure. This configuration serves to change the effective polarity of the combined columns and enables tweaking or fine control of the columns selectively to achieve difficult separations.

Figure 11:
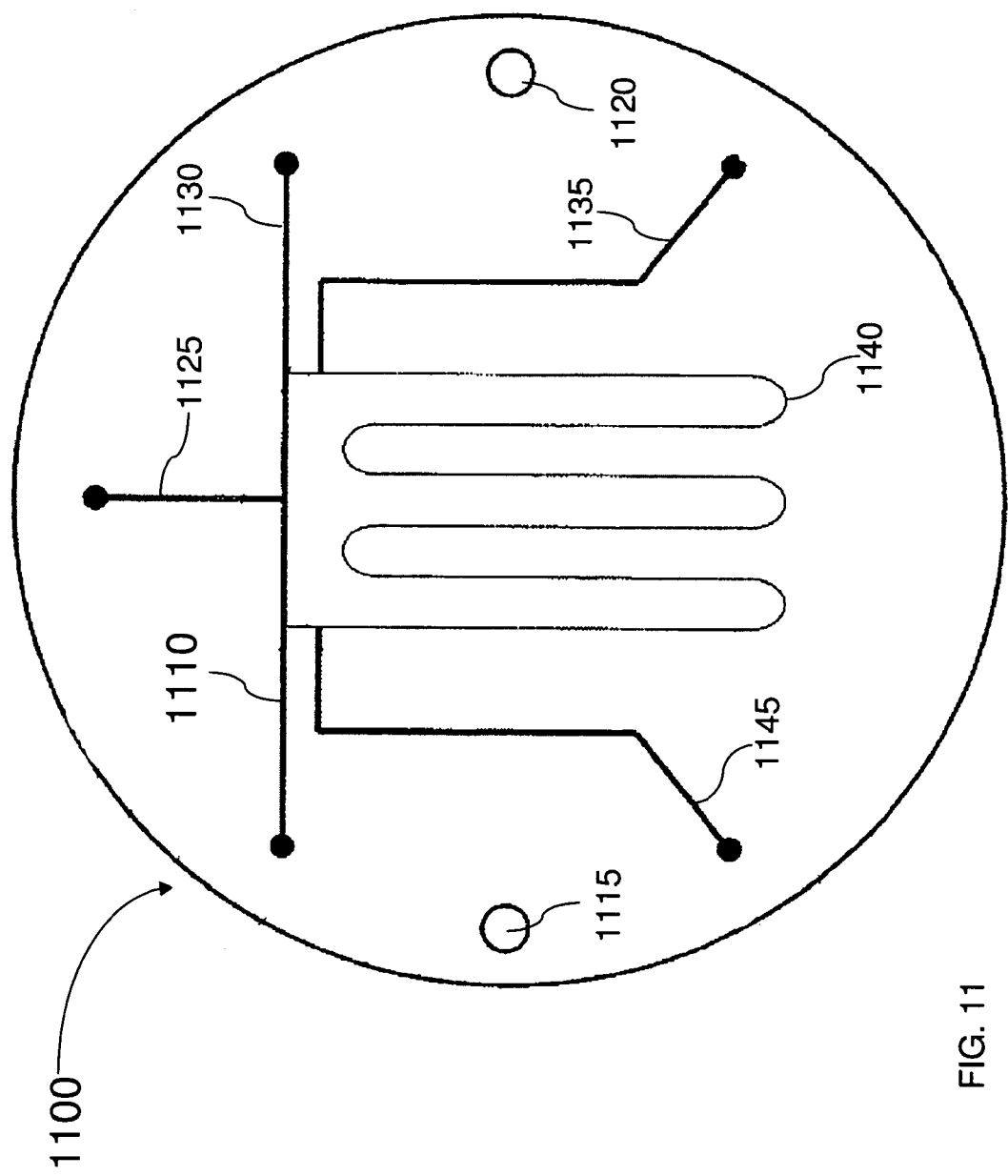
FIG. 11 is a cross-section of a microfluidic device showing the internal microchannel, in accordance with certain examples.

In accordance with certain examples, one configuration of a microfluidic device is shown in FIG. 11. In this cross-sectional view, the microfluidic device is configured as a wafer 1100 and includes an internal microchannel 1110 that has a variable diameter at different portions of the microchannel 1110. For example, the diameter of the microchannel at area 1125 can be about 300 to about 700 microns, e.g., about 400 to about 600 microns in diameter, the diameter of the microchannel at area 1130 can be about 75 microns to about 300 microns, e.g., about 100 microns to about 200 microns in diameter, the diameter of the microchannel at area 1135 can be about 300 to about 700 microns, e.g., about 400 to about 600 microns in diameter, the diameter of the microchannel at area 1140 can be about 75 microns to about 300 microns, e.g., about 100 microns to about 200 microns in diameter, and the diameter of the microchannel at area 1145 can be about 300 to about 700 microns, e.g., about 400 to about 600 microns in diameter. In certain examples, the diameter of the restricted portion in the microchannel, e.g., area 1140, can be at least two times smaller than the diameter of the adjacent channel portions, e.g., at least three times smaller, at least four times smaller or at least five times smaller, to provide for restricted fluid flow. The wafer 1100 also includes openings or apertures 1115 and 1120 that can couple the wafer to a wafer holder or other device to hold the wafer 1100 in place during operation of the system.

Figure 12:
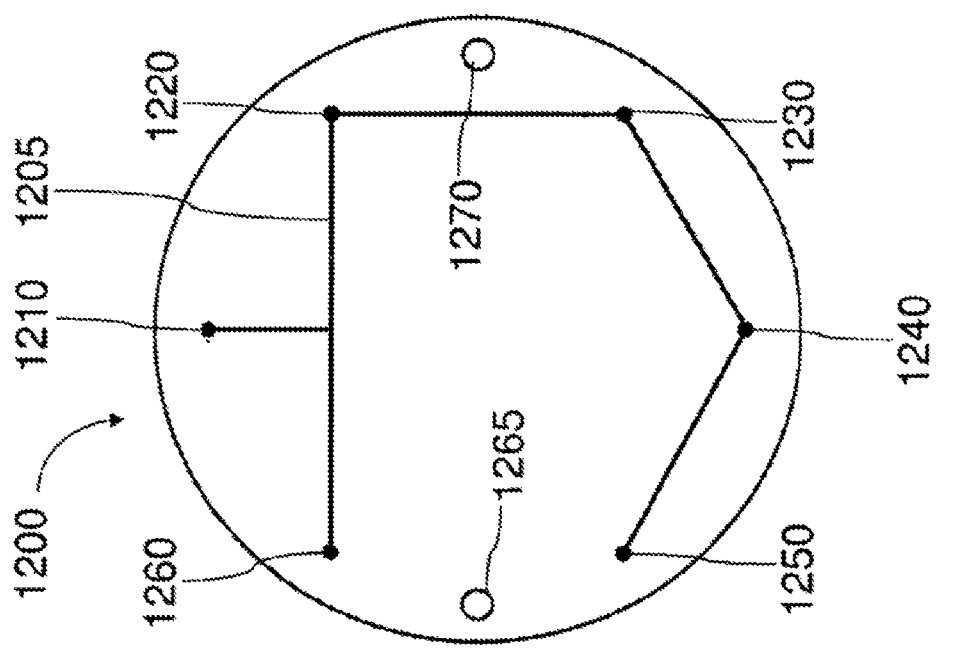
FIG. 12 is a cross-section of a microfluidic device including four outlet ports, in accordance with certain examples.

In certain examples, the microfluidic device can include various ports, e.g., inlet and outlet ports, that can provide a fluidic coupling between the column and the various other components downstream of the microfluidic device. One configuration of such a wafer 1200 is shown in FIG. 12. In this configuration, the ports are arranged in series in a microchannel 1205. A port 1210 is fluidically coupled to a column. The flow of gas through the wafer 1200 is in the general direction from the port 1210 to ports 1220, 1230, 1240 and 1250. A midpoint pressure regulator can be fluidically coupled to the wafer 1200 at a port 1260. During operation, effluent from the column that enters through the port 1210 will be mixed with a carrier gas from the midpoint regulator entering through the port 1260 and then flow in succession through ports 1220, 1230, 1240 and finally 1250. The wafer 1200 can be coupled to a holder through apertures 1265 and 1270. Depending on the exact configuration, the various restrictors present in the system may take different operational states. One example of restrictor setup using the wafer 1200 is shown in Table 1.

TABLE 1

| Number of Detectors | Port 1220 | 1230 | 1240 | 1250 |
|---|---|---|---|---|
| 1 | Closed | Closed | Closed | Restrictor |
| 2 | Closed | Closed | Slowest flow restrictor | Fastest flow restrictor |
| 3 | Closed | Slowest flow restrictor | Medium flow restrictor | Fastest flow restrictor |
| 4 | Slowest flow restrictor | Slowest Medium flow restrictor | Fastest Medium flow restrictor | Fastest flow restrictor |

The restrictors are arranged in order of increasing flow rate with the fastest flow rate being at port 1250. The microchannel can be arranged so that the outlet ports are within a single microchannel flow path. To plug or close any particular port, the port may be capped or otherwise blocked using blanking nuts, fittings, ferrules or other suitable devices that can provide a fluid tight seal. When closed, desirably no or little dead volume in the port is created that could prevent peak losses or cause tailing. By using a single wafer as shown in FIG. 12, anywhere from 1-4 detectors can be used without having to change the wafer for each different detector combination.

Figure 13:
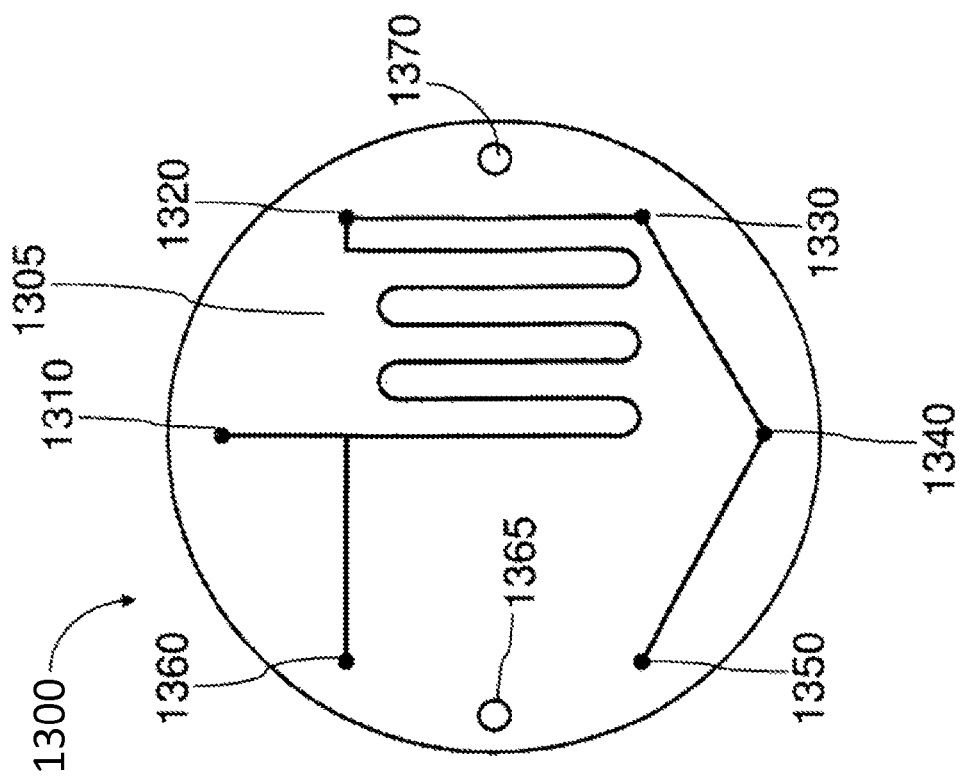
FIG. 13 is a cross-section of a microfluidic device including an elongated portion in the microchannel, in accordance with certain examples.

In accordance with certain examples, the particular length of the flow path between various ports can vary depending on the desired effect. One configuration of a wafer having a different flow path configuration is shown in FIG. 13. The wafer 1300 includes a microchannel 1305, a port 1310 that is fluidically coupled to a column (not shown), a port 1360 that is fluidically coupled to a midpoint pressure regulator (not shown) and ports 1320, 1330, 1340 and 1350, each of which may or may not be fluidically coupled to a restrictor and/or detector. A portion of the microchannel 1305 is elongated to provide an increased flow path length to permit additional mixing of carrier gas from the midpoint regulator port 1360 and the column effluent port 1310. Such increased length can, for example, provide additional time to provide increased sample residence time and a more homogenous mixture of column effluent and carrier gas, which can be used to avoid or reduce diffusional broadening of the analyte peaks as described in more detail herein. In addition, the particular length of the flow path between any two or more of ports 1320, 1330, 1340 and 1350 can be different than the other lengths. When such a different length is present, it may be desirable to alter the restrictor flow rate to balance the flow rates of gas provided to the different detectors. Openings 1365 and 1370 can be used, for example, to attach the microfluidic device to a holder or other device designed to retain the microfluidic device at a desired site or in a desired orientation.

Figure 14A:
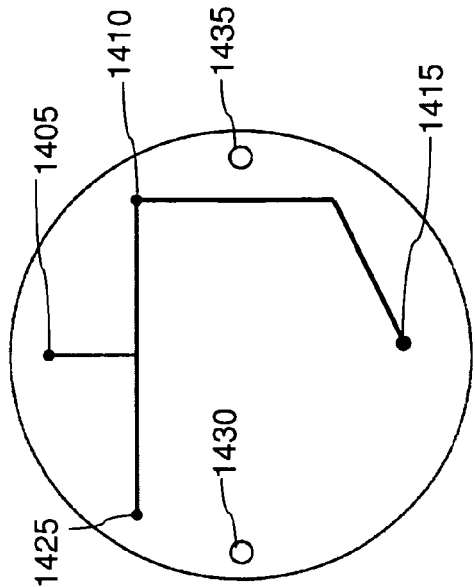
FIGS. 14A and 14B are cross-section of a microfluidic device including two outlet ports and three outlet ports, respectively, each arranged in series with the other outlet ports, in accordance with certain examples.
Figure 14B:
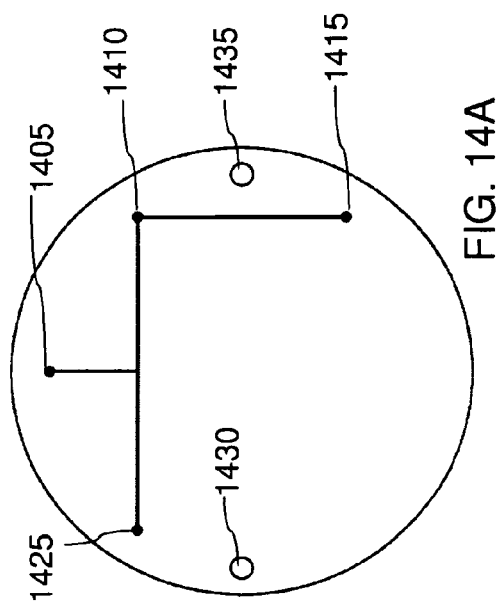

It will be recognized by the person of ordinary skill in the art, given the benefit of this disclosure that the exact number of ports in the wafer can vary and may be, for example, fewer ports or more ports that the illustrative configurations shown in FIGS. 12 and 13. Illustrative configurations are shown in FIGS. 14A-15B. Referring to FIG. 14A, a wafer includes a column effluent port 1405 fluidically coupled to a midpoint pressure regulator port 1425 and ports 1410 and 1415 each of which can be fluidically coupled to a restrictor and/or detector, for example. Apertures 1430 and 1435 can be used to attach the wafer to a holder or other structures of the microfluidic device. The length of the flow path between the two ports 1410 and 1415 can vary, and the particular restrictor flow rate can be altered to provide substantially the same flow rate through the different ports, if desired. FIG. 14B shows a configuration where the length of the flow path between ports 1410 and 1415 has been lengthened. Such lengthening may be desirable, for example, to provide more spacing for coupling of fittings to the various ports and facilitate overall setup of the device, to provide for increased residence time or other desired performance.

Figure 15A:
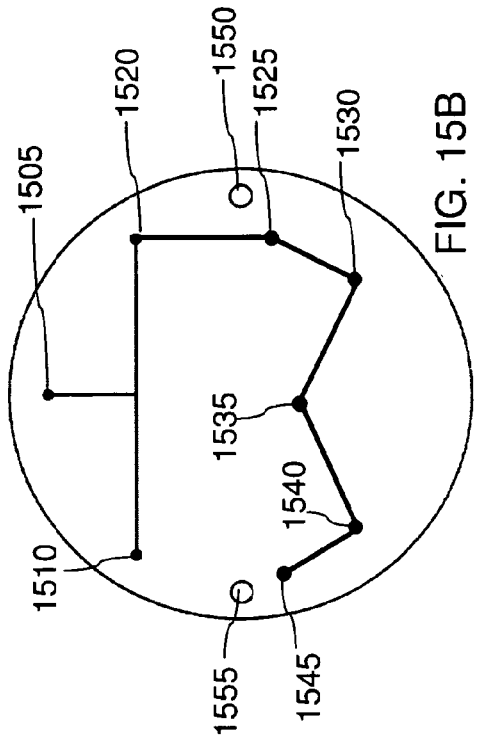
FIGS. 15A and 15B show other illustration of microfluidic devices, in accordance with certain examples.
Figure 15B:
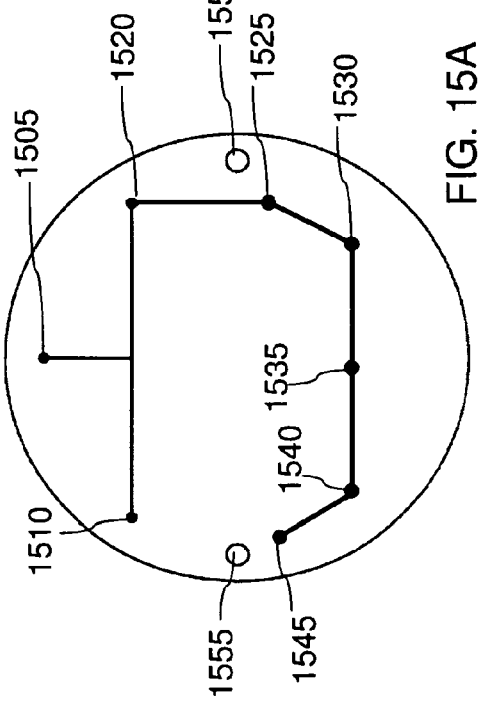

While two ports 1410 and 1415 are shown in FIGS. 14A and 14B, port 1415 can be omitted and a single port may be present. In the alternative, one or more additional ports can be present to provide fluidic coupling between such additional port(s) and a restrictor(s) and/or detector(s). Two configurations using additional ports are shown in FIGS. 15A and 15B. Referring to FIG. 15A, the wafer includes a column effluent port 1505 fluidically coupled to a midpoint pressure regulator port 1510 and to ports 1520, 1525, 1530, 1535, 1540 and 1545. Apertures 1550 and 1555 can be used to attach the wafer to a holder or other portions of the microfluidic device. FIG. 15B shows a similar arrangement to that of FIG. 15A, but the position of port 1535 has been moved.

In certain examples, the exact cross-sectional shape and angles of the microchannels can vary. In certain examples, the cross-sectional shape of the microchannel is circular or substantially circular, whereas in other examples, elliptical shapes or other non-circular shapes can be present. Similarly, the angle of the microchannel between two or more ports can vary and where a non-continuous flow path is present, the angle made by the change in direction of the flow path may be a sharp angle or may be a gradual angle such as, for example, an elbow or a curved surface. For example, in fluid chromatography systems where sharp angles may create turbulent flow, the angles can be configured as elbow or gradual turns to avoid or reduce such turbulence.

In certain examples, the microfluidic devices described herein can be used in many different configurations. FIGS. 16-25 show several illustrative configurations. Referring to FIG. 16, a single detector configuration that can be used, for example, to backflush and in a MS Vent mode is shown. The system 1600 includes an injector 1610 fluidically coupled to a pressure regulator 1605 through a supply line 1607. The injector 1610 is also fluidically coupled to a column 1620 through a supply line 1612. The column 1620 is fluidically coupled to a microfluidic device 1625 through a supply line 1617. The microfluidic device 1625 includes a column effluent port 1627 fluidically coupled to a midpoint pressure regulator 1630 through a port 1633. Gas is provided from the midpoint pressure regulator 1630 to the port 1633 through a supply line 1632. The microfluidic device 1625 includes ports 1635, 1640, 1645 and 1650. In the embodiment of FIG. 16, ports 1635, 1640 and 1645 are closed or plugged such that no gas flows into them. The port 1650 is fluidically coupled to a detector 1660 through a restrictor 1655. In operation, a sample is introduced into the injector 1610 and species in the sample can be separated using the column 1620. Species elute from the column 1620 and are provided to the detector 1660 through the microfluidic device 1625. Flow control of the overall system may be performed as described herein or using other suitable algorithms. The arrows show the general gas flow in the system 1600. If desired, any of ports 1635, 1640 or 1645 can be coupled to a sniffer or other device to provide for in-line sampling of gas and/or species in the gas within the microchannel of the microfluidic device 1625. In addition, by increasing the flow of gas provided by the midpoint pressure regulator to be greater than the flow rate to the column, the system 1600 can be backflushed or can be vented, e.g., can be operated in a MS vent mode.

In accordance with certain examples and referring to FIG. 17, a dual detector configuration is shown. The system 1700 includes an injector 1710 fluidically coupled to a pressure regulator 1705 through a supply line 1707. The injector 1710 is also fluidically coupled to a column 1720 through a supply line 1712. The column 1720 is fluidically coupled to a microfluidic device 1725 through a supply line 1717. The microfluidic device 1725 includes a column effluent port 1727 fluidically coupled to a midpoint pressure regulator 1730 through a port 1733. Gas is provided from the midpoint pressure regulator 1730 to the port 1733 through a supply line 1732. The microfluidic device 1725 includes ports 1735, 1740, 1745 and 1750. In the embodiment of FIG. 17, ports 1735 and 1740 are closed or plugged such that no gas flows into them. The ports 1745 and 1750 are each fluidically coupled to a detector 1770 and 1760, respectively, through a restrictor 1765 and 1755, respectively. In operation, a sample is introduced into the injector 1710 and species in the sample can be separated using the column 1720. Species elute from the column 1720 and are provided to one or both of the detectors 1760 and 1770 through the microfluidic device 1725. Flow control of the overall system may be performed as described herein or using other suitable algorithms. The arrows show the general gas flow in the system 1700. The detectors 1760 and 1770 may be the same or may be different. In addition different peaks can be provided to different detectors by including suitable valving in the supply lines and/or by actuating one of more of the ports of the microfluidic device 1725 to be in a closed position, e.g., using a switching valve.

Figure 18:
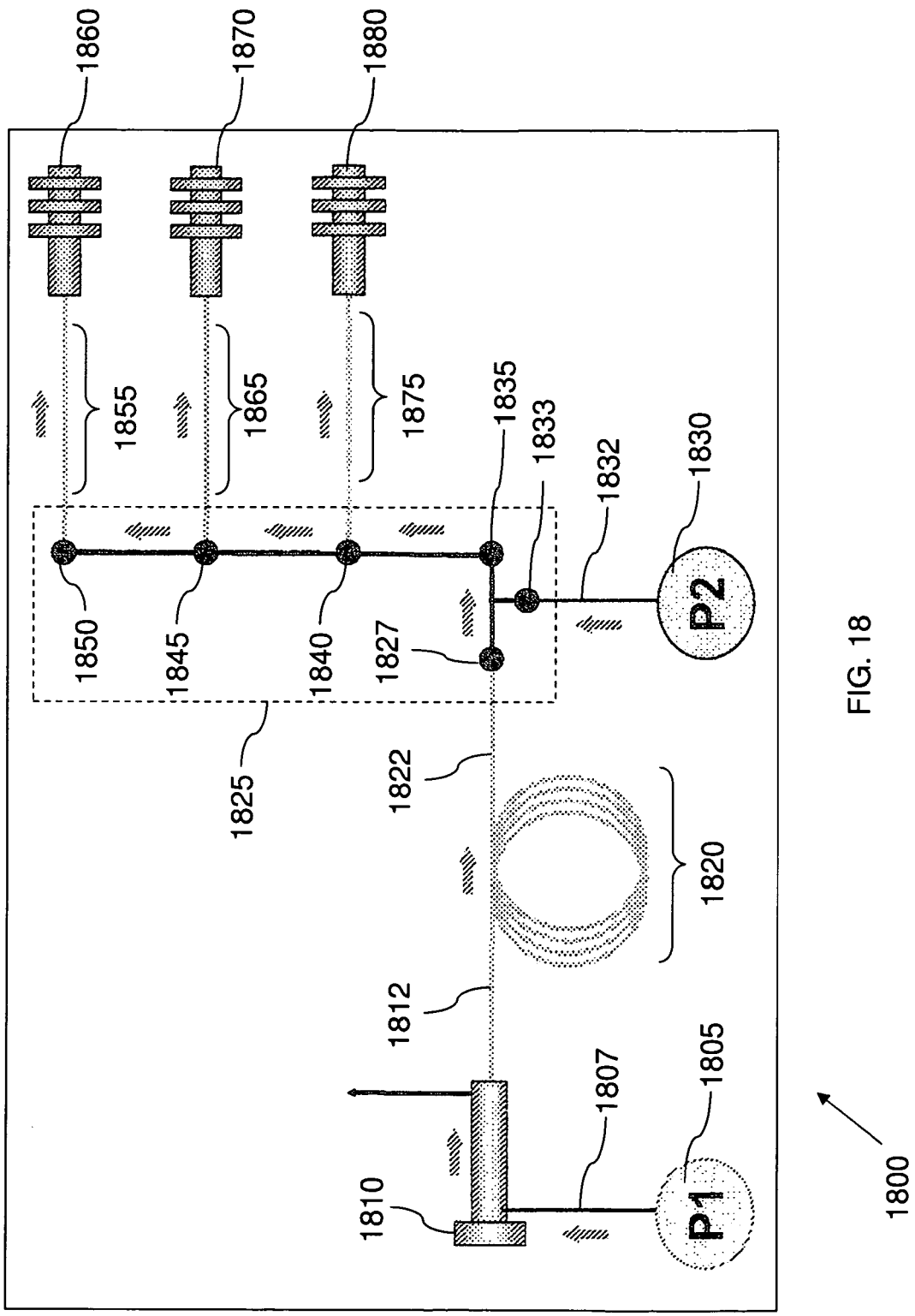
FIG. 18 is a schematic of a chromatography system that includes three detectors each fluidically coupled to a microfluidic device, in accordance with certain examples.

In accordance with certain examples and referring to FIG. 18, a three detector configuration is shown. The system 1800 includes an injector 1810 fluidically coupled to a pressure regulator 1805 through a supply line 1807. The injector 1810 is also fluidically coupled to a column 1820 through a supply line 1812. The column 1820 is fluidically coupled to a microfluidic device 1825 through a supply line 1822. The microfluidic device 1825 includes a column effluent port 1827 fluidically coupled to a midpoint pressure regulator 1830 through a port 1833. Gas is provided from the midpoint pressure regulator 1830 to the port 1833 through a supply line 1832. The microfluidic device 1825 includes ports 1835, 1840, 1845 and 1850. In the embodiment of FIG. 18, port 1835 is closed or plugged such that no gas flows into it. The ports 1840, 1845 and 1850 are each fluidically coupled to a detector 1880, 1870 and 1860, respectively, through a restrictor 1875, 1865 and 1855, respectively. In operation, a sample is introduced into the injector 1810 and species in the sample can be separated using the column 1820. Species elute from the column 1820 and are provided to one or more of the detectors 1860, 1870 and 1880 through the microfluidic device 1825. Flow control of the overall system may be performed as described herein or using other suitable algorithms. The arrows show the general gas flow in the system 1800. The detectors 1860, 1870 and 1880 may be the same or may be different or two of the detector 1860, 1870 and 1880 may be the same. In addition different peaks can be provided to different detectors by including suitable valving in the supply lines and/or by actuating one of more of the ports of the microfluidic device 1825 to be in a closed position, e.g., using a switching valve.

Figure 19:
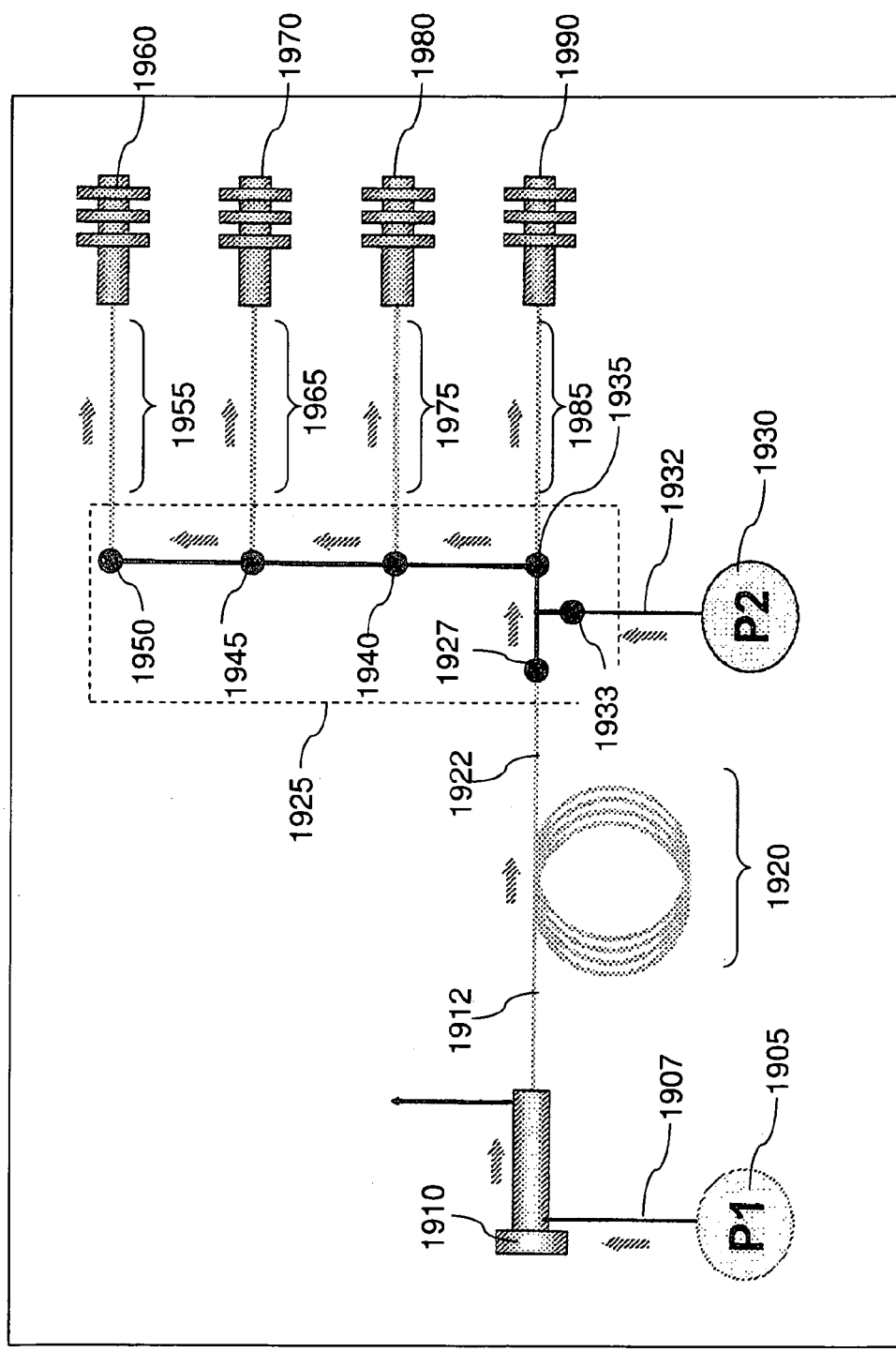
FIG. 19 is a schematic of a chromatography system that includes four detectors each fluidically coupled to a microfluidic device, in accordance with certain examples.

In accordance with certain examples and referring to FIG. 19, a system 1900 including four detectors is shown. The system 1900 includes an injector 1910 fluidically coupled to a pressure regulator 1905 through a supply line 1907. The injector 1910 is also fluidically coupled to a column 1920 through a supply line 1912. The column 1920 is fluidically coupled to a microfluidic device 1925 through a supply line 1922. The microfluidic device 1925 includes a column effluent port 1927 fluidically coupled to a midpoint pressure regulator 1930 through a port 1933. Gas is provided from the midpoint pressure regulator 1930 to the port 1933 through a supply line 1932. The microfluidic device 1925 includes ports 1935, 1940, 1945 and 1950. In the embodiment of FIG. 19, the ports 1935, 1940, 1945 and 1950 are each fluidically coupled to a detector 1990, 1980 and 1970 and 1960, respectively, through a restrictor 1985, 1975, 1965 and 1955, respectively. In operation, a sample is introduced into the injector 1910 and species in the sample can be separated using the column 1920. Species elute from the column 1920 and are provided to one or more of the detectors 1960, 1970, 1980 and 1990 through the microfluidic device 1925. Flow control of the overall system may be performed as described herein or using other suitable algorithms. The arrows show the general gas flow in the system 1900. The detectors 1960, 1970, 1980 and 1990 may be the same or may be different or any two or three of the detectors 1960, 1970, 1980 and 1990 may be the same. In addition different peaks can be provided to different detectors by including suitable valving in the supply lines and/or by actuating one of more of the ports of the microfluidic device 1925 to be in a closed position, e.g., using a switching valve.

Figure 20:
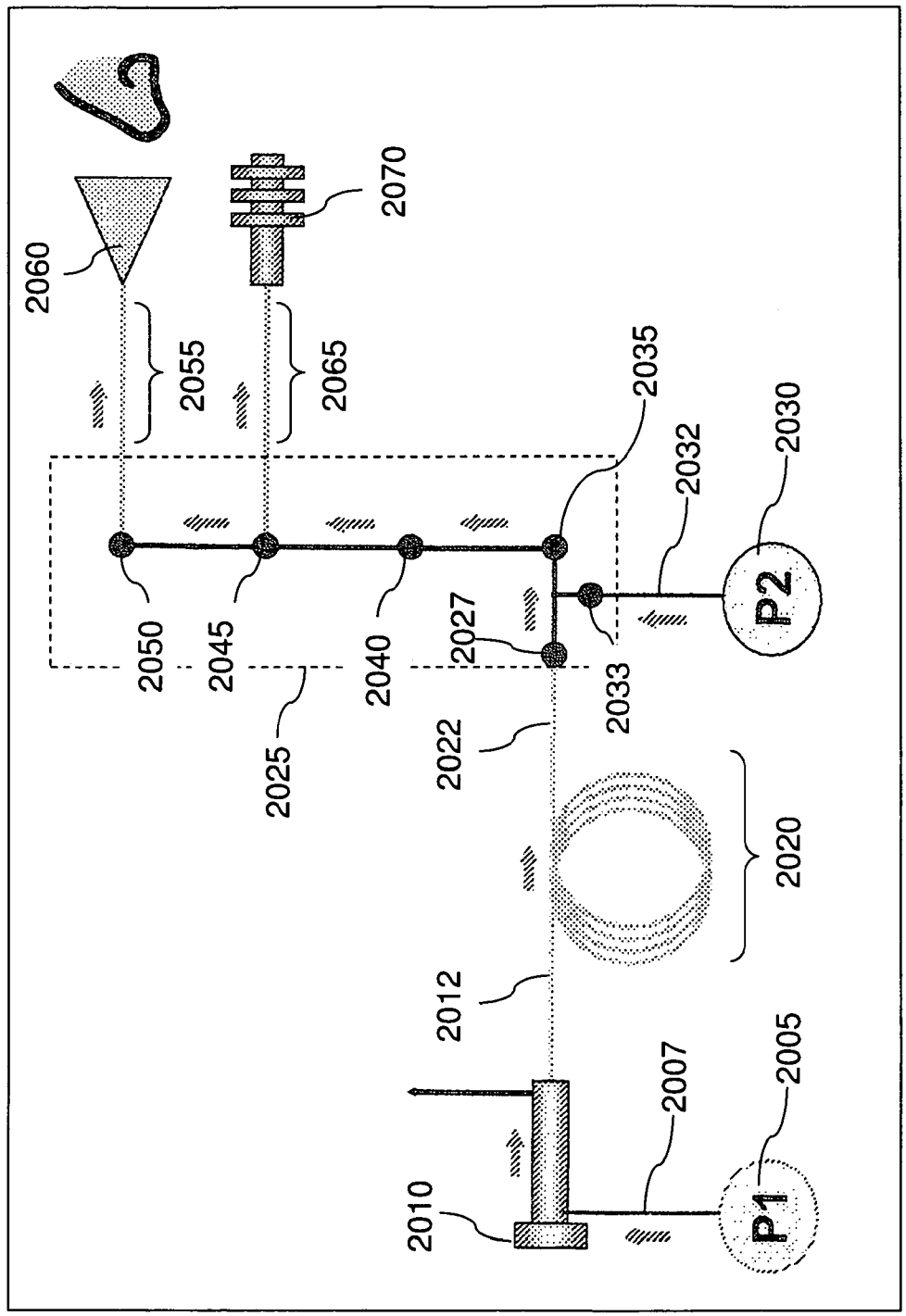
FIG. 20 is a schematic of a chromatography system that includes a single detector and a sniffer port each fluidically coupled to a microfluidic device, in accordance with certain examples.

In accordance with certain examples and referring to FIG. 20, a system 2000 including a single detector 2070 and a sniffer port 2060 is shown. The system 2000 includes an injector 2010 fluidically coupled to a pressure regulator 2005 through a supply line 2007. The injector 2010 is also fluidically coupled to a column 2020 through a supply line 2012. The column 2020 is fluidically coupled to a microfluidic device 2025 through a supply line 2022. The microfluidic device 2025 includes a column effluent port 2027 fluidically coupled to a midpoint pressure regulator 2030 through a port 2033. Gas is provided from the midpoint pressure regulator 2030 to the port 2033 through a supply line 2032. The microfluidic device 2025 includes ports 2035, 2040, 2045 and 2050. In the embodiment of FIG. 20, the ports 2035 and 2040 are closed or plugged such that no gas flows into them. The port 2045 is fluidically coupled to the detector 2070 through a restrictor 2065. The port 2050 is fluidically coupled to the sniffer port 2060, which can be used for in-line sampling or monitoring of species in the effluent or generally provides a port from which species in the fluid path can be withdrawn, if desired, through a restrictor 2055. In operation, a sample is introduced into the injector 2010 and species in the sample can be separated using the column 2020. Species elute from the column 2020 and are provided to one or more of the detector 2070 or the sniffer port 2060 through the microfluidic device 2025. Flow control of the overall system may be performed as described herein or using other suitable algorithms. The arrows show the general gas flow in the system 2000. The sniffer port 2060 may typically remain in a closed position until the user desires to sample from that port. Suitable valving in the supply lines and/or by actuating the sniffer port 2060 can open the sniffer port, as desired.

Figure 21:
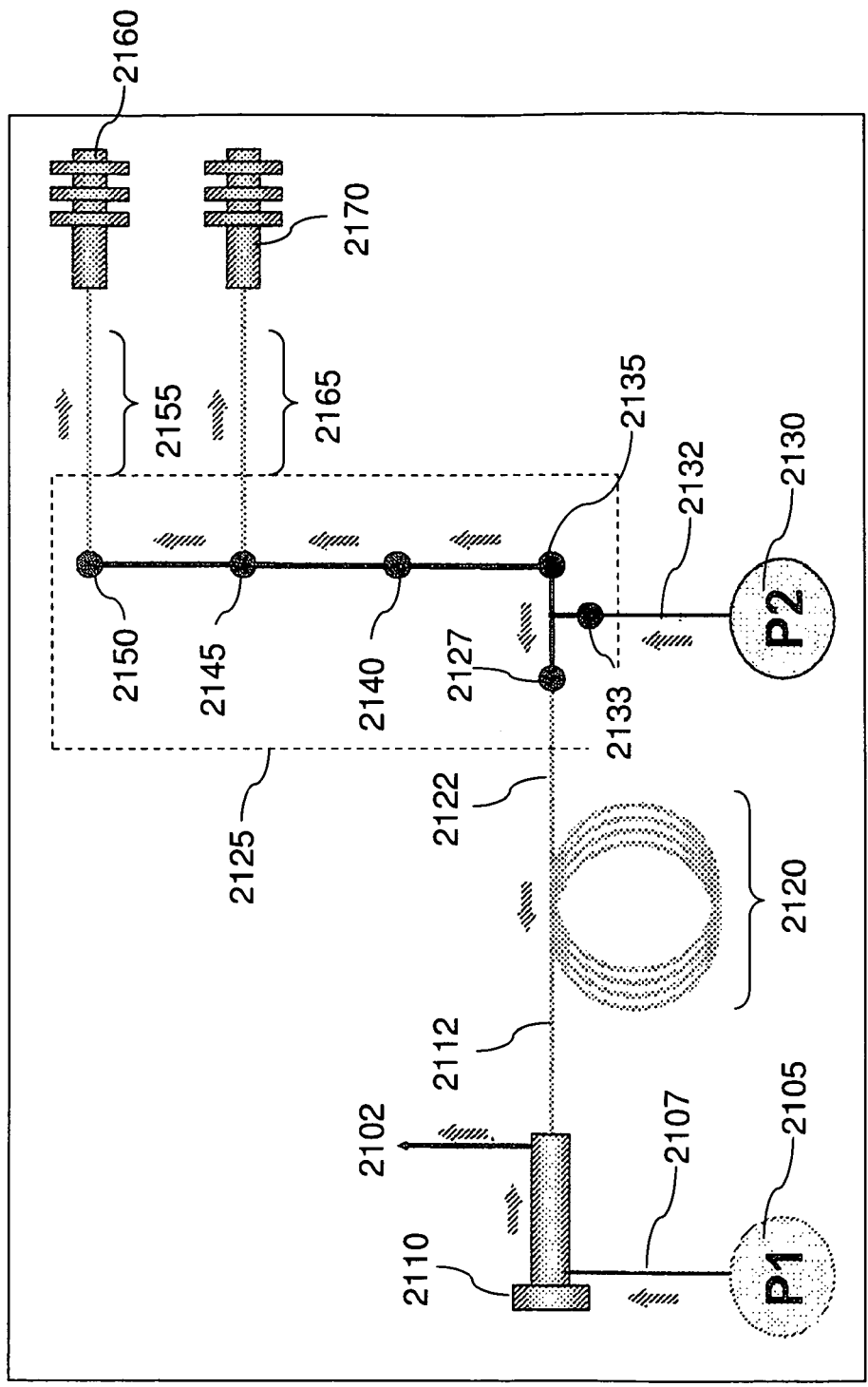
FIG. 21 is a schematic of a chromatography system that includes two detectors each fluidically coupled to a microfluidic device and where backflushing of a first column can be performed, in accordance with certain examples.

In accordance with certain examples and referring to FIG. 21, a system 2100 that is configured for backflushing or venting in an MS system is provided. The system 2100 is similar to that shown in FIG. 17, but the flow rates of the various gases are altered to perform the backflushing or venting. Referring to FIG. 21, system 2100 includes an injector 2110 fluidically coupled to a pressure regulator 2105 through a supply line 2107. The injector 2110 is also fluidically coupled to a column 2120 through a supply line 2112. The column 2120 is fluidically coupled to a microfluidic device 2125 through a supply line 2122. The microfluidic device 2125 includes a column effluent port 2127 fluidically coupled to a midpoint pressure regulator 2130 through a port 2133. Gas is provided from the midpoint pressure regulator 2130 to the port 2133 through a supply line 2132. The microfluidic device 2125 includes ports 2135, 2140, 2145 and 2150. In the embodiment of FIG. 21, ports 2135 and 2140 are closed or plugged such that no gas flows into them. The ports 2145 and 2150 are each fluidically coupled to a detector 2170 and a detector 2160, respectively, through a restrictor 2165 and 2155, respectively. In operation, a sample is introduced into the injector 2110 and species in the sample can be separated using the column 2120. Species elute from the column 2120 and are provided to one or both of the detectors 2160 and 2170 through the microfluidic device 2125. Flow control of the overall system may be performed as described herein or using other suitable algorithms. The arrows show the general gas flow in the system 2100 in this backflushing configuration. The detectors 2160 and 2170 may be the same or may be different. In the backflushing or venting mode, the flow rate of gas from the midpoint pressure regulator 2130 is greater than the flow of gas from the pressure regulator 2105, e.g., $p_2$ is greater than $p_1$. The result of this differential flow is that gas is flushed back through the column 2120 and can be vented from the system, for example, through outlet 2102. Where an MS detector is present, the differential fluid flow can be used to maintain the MS detector at its operating temperature while the system can be flushed. Such an advantage can provide a substantial time savings.

Figure 22:
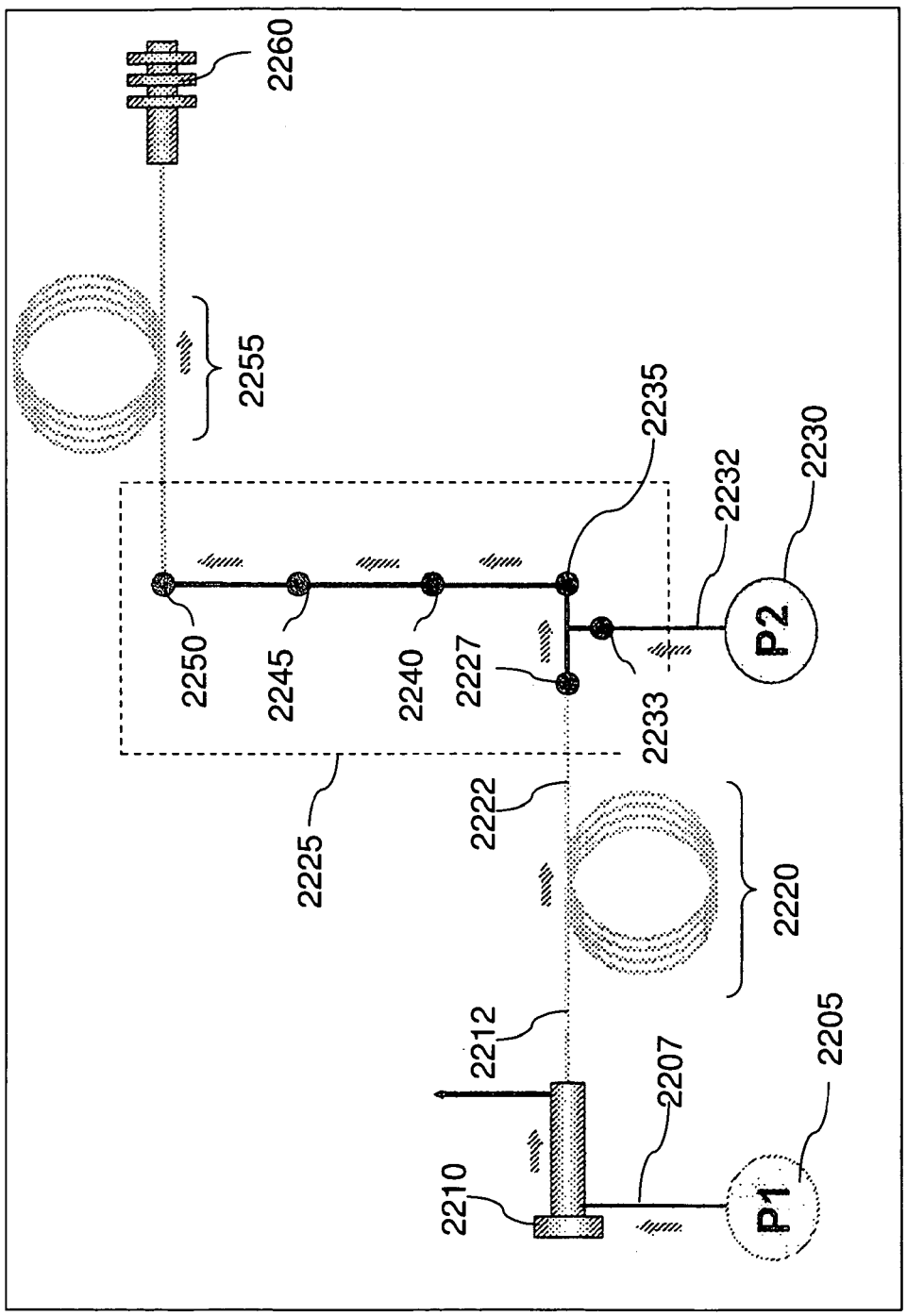
FIG. 22 is a schematic of a chromatography system that includes two columns and a single detector fluidically coupled to a microfluidic device, in accordance with certain examples.

In accordance with certain examples and referring to FIG. 22, a dual column backflush configuration is shown. The system 2200 includes an injector 2210 fluidically coupled to a pressure regulator 2205 through a supply line 2207. The injector 2210 is also fluidically coupled to a first column 2220 through a supply line 2212. The first column 2220 is fluidically coupled to a microfluidic device 2225 through a supply line 2222. The microfluidic device 2225 includes a column effluent port 2227 fluidically coupled to a midpoint pressure regulator 2230 through a port 2233. Gas is provided from the midpoint pressure regulator 2230 to the port 2233 through a supply line 2232. The microfluidic device 2225 includes ports 2235, 2240, 2245 and 2250. In the embodiment of FIG. 22, ports 2235, 2240 and 2245 are closed or plugged such that no gas flows into them. The port 2250 is fluidically coupled to a second column 2255. The second column 2255 is fluidically coupled to a detector 2260. In operation, a sample is introduced into the injector 2210 and species in the sample can be separated using the first column 2220. Species elute from the first column 2220 and are provided to the second column 2255 through the microfluidic device 2225. Flow control of the overall system may be performed as described herein or using other suitable algorithms. The arrows show the general gas flow in the system 2200. The configuration of system 2200 permits backflushing of the first column 2220 once the effluent enters into the microfluidic device 2225. By increasing the pressure $p_2$ to be larger than the pressure $p_1$, e.g., so the flow rate from the midpoint pressure regulator 2230 is greater than the flow rate from the pressure regulator 2205, gas will flow into the first column 2220 to backflush it, and will also pass the effluent from the microfluidic device 2225 to the second column 2255 for continued or additional separation using the second column 2255. Polarity tuning methods may also be performed using a system as shown in FIG. 22.

Figure 23:
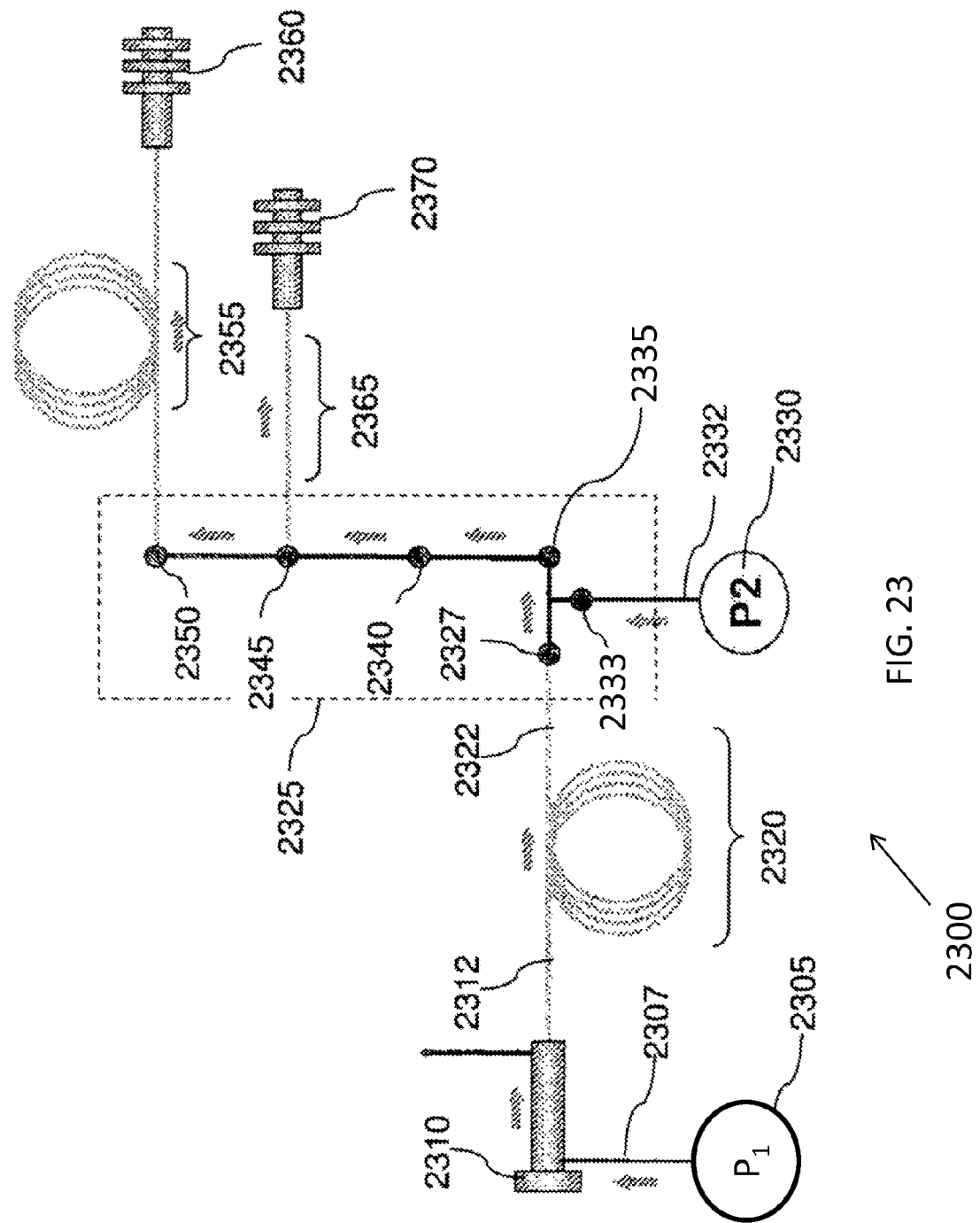
FIG. 23 is a schematic of a chromatography system that includes two columns and two detectors each fluidically coupled to a microfluidic device, in accordance with certain examples.

In accordance with certain examples, a dual column backflush configuration with a midpoint monitoring detector is shown in FIG. 23. The system 2300 includes an injector 2310 fluidically coupled to a pressure regulator 2305 through a supply line 2307. The injector 2310 is also fluidically coupled to a first column 2320 through a supply line 2312. The first column 2320 is fluidically coupled to a microfluidic device 2325 through a supply line 2322. The microfluidic device 2325 includes a column effluent port 2327 fluidically coupled to a midpoint pressure regulator 2330 through a port 2333. Gas is provided from the midpoint pressure regulator 2330 to the port 2333 through a supply line 2332. The microfluidic device 2325 includes ports 2335, 2340, 2345 and 2350. In the embodiment of FIG. 23, ports 2335 and 2340 are closed or plugged such that no gas flows into them. The port 2350 is fluidically coupled to a second column 2355. The second column 2355 is fluidically coupled to a detector 2360. The port 2345 is fluidically coupled to a detector 2370 through a restrictor 2365. In operation, a sample is introduced into the injector 2310 and species in the sample can be separated using the first column 2320. Species elute from the first column 2320 and are provided to the second column 2355 through the microfluidic device 2325. In addition, species can be detected by using the detector 2370. Flow control of the overall system may be performed as described herein or using other suitable algorithms. The arrows show the general gas flow in the system 2300. The configuration of system 2300 permits backflushing of the first column 2320 once the effluent enters into the microfluidic device 2325. By increasing the pressure $p_2$ to be larger than the pressure $p_1$, gas will flow into the first column 2320 to backflush it, and will also pass the effluent from the microfluidic device 2325 to the second column 2355 for continued or additional separation using the second column 2355. Effluent can also be provided to the detector 2370 without any further separation. Polarity tuning methods may also be performed using a system as shown in FIG. 23.

Figure 24:
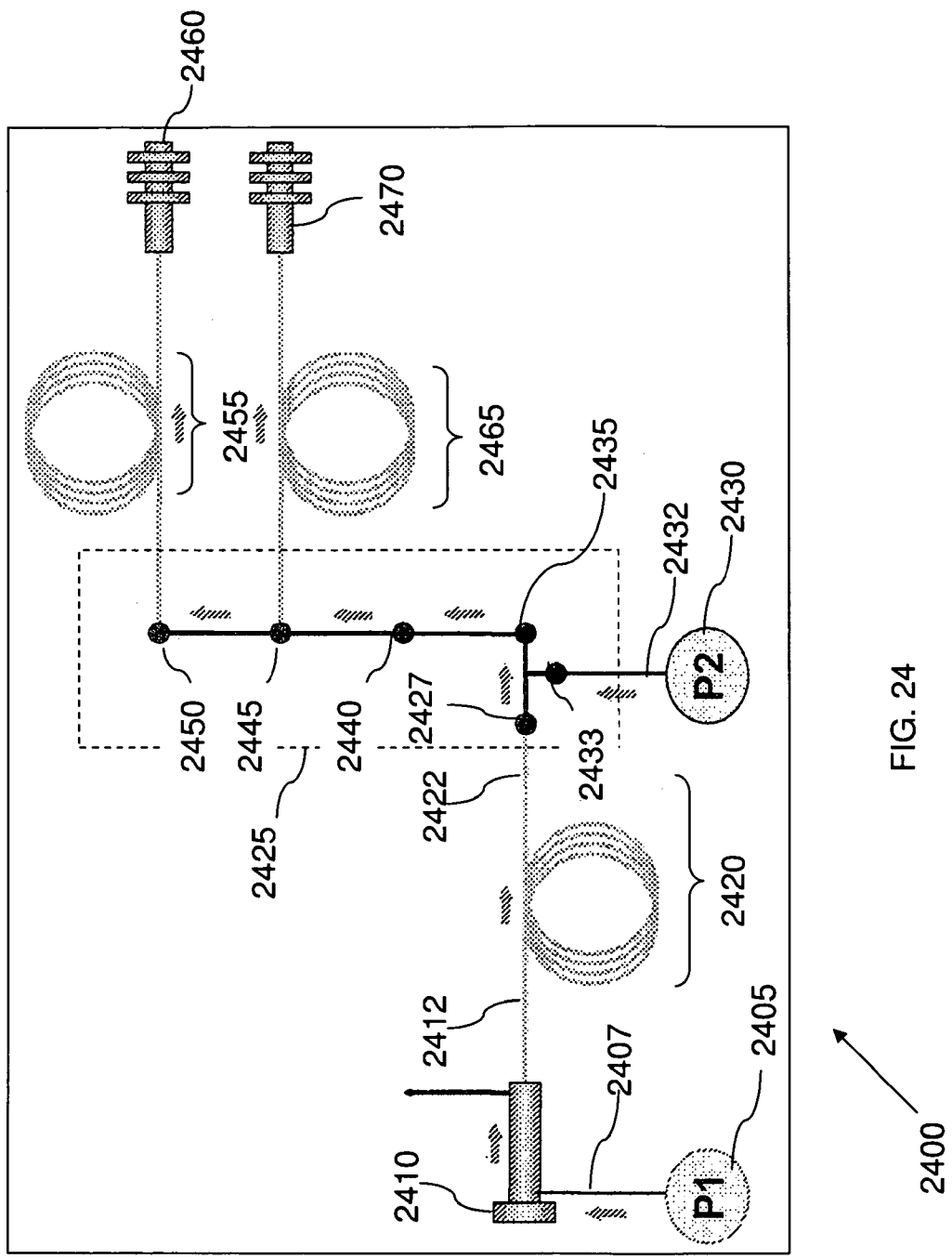
FIG. 24 is a schematic of a chromatography system that includes three columns and two detectors each fluidically coupled to a microfluidic device, in accordance with certain examples.

In accordance with certain examples, a three column backflush configuration is shown in FIG. 24. The system 2400 includes an injector 2410 fluidically coupled to a pressure regulator 2405 through a supply line 2407. The injector 2410 is also fluidically coupled to a first column 2420 through a supply line 2412. The first column 2420 is fluidically coupled to a microfluidic device 2425 through a supply line 2422. The microfluidic device 2425 includes a column effluent port 2427 fluidically coupled to a midpoint pressure regulator 2430 through a port 2433. Gas is provided from the midpoint pressure regulator 2430 to the port 2433 through a supply line 2432. The microfluidic device 2425 includes ports 2435, 2440, 2445 and 2450. In the embodiment of FIG. 24, ports 2435 and 2440 are closed or plugged such that no gas flows into them. The port 2450 is fluidically coupled to a second column 2455. The second column 2455 is fluidically coupled to a detector 2460. The port 2445 is fluidically coupled to a third column 2465 that is fluidically coupled to a detector 2470. In operation, a sample is introduced into the injector 2410 and species in the sample can be separated using the first column 2420. Species elute from the first column 2420 and are provided to the second column 2455 and third column 2465 through the microfluidic device 2425. In addition, species can be detected by using the detectors 2460 and 2470. Flow control of the overall system may be performed as described herein or using other suitable algorithms. The arrows show the general gas flow in the system 2400. The configuration of system 2400 permits backflushing of the first column 2420 once the effluent enters into the microfluidic device 2425. By increasing the pressure $p_2$ to be larger than the pressure $p_1$, gas will flow into the first column 2420 to backflush it, and will also pass the effluent from the microfluidic device 2425 to the second column 2455 and third column 2465 for continued or additional separation using these additional columns. Polarity tuning methods may also be performed using a system as shown in FIG. 24. While not shown, the system of FIG. 24 may include a detector fluidically coupled to one of the ports 2435 or 2440.

Figure 25:
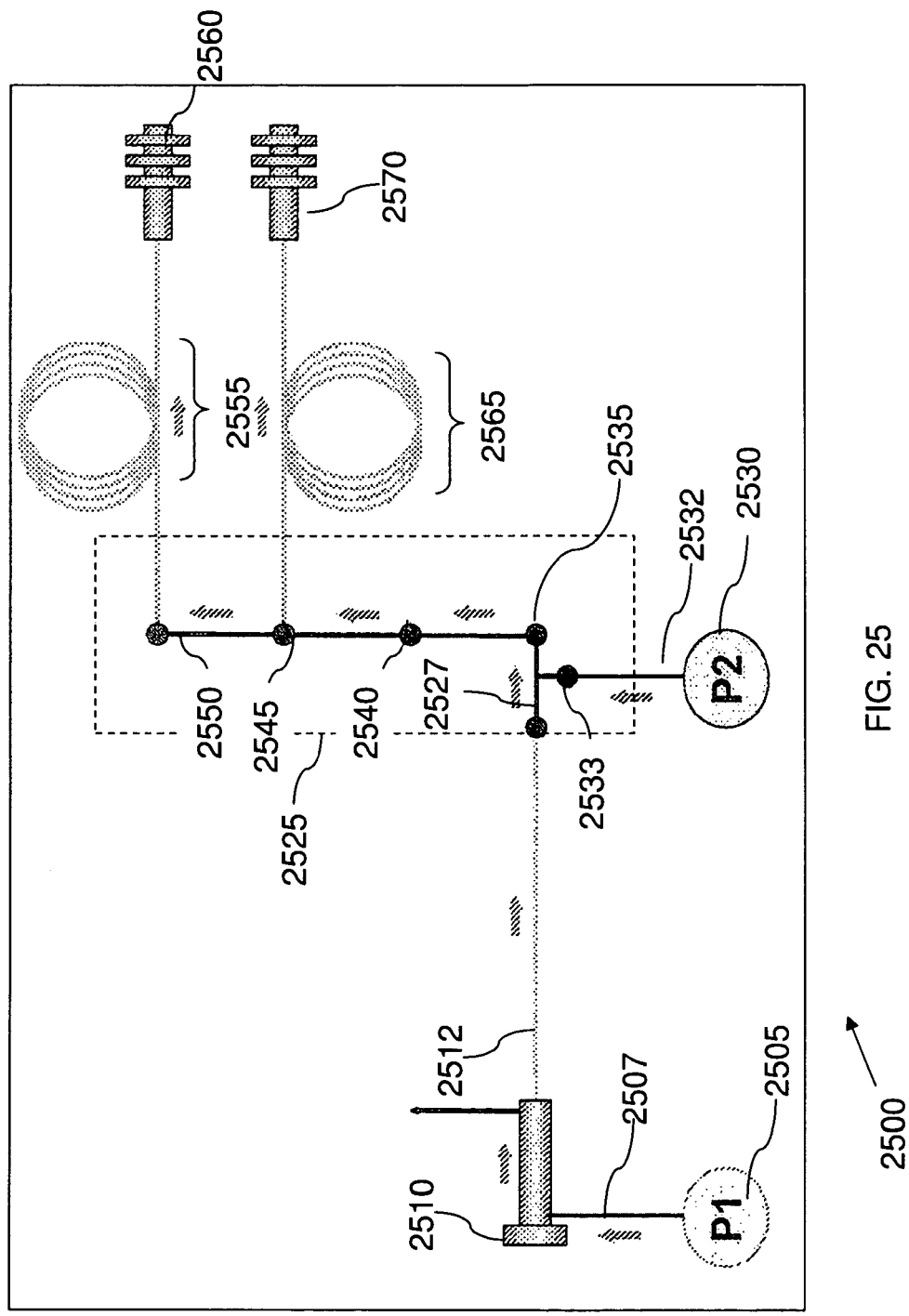
FIG. 25 is a schematic of a chromatography system that includes two detectors each fluidically coupled to a microfluidic device through a column, in accordance with certain examples.

In certain examples and referring to FIG. 25, a system may be configured with a microfluidic device to split the injector flow into two or more columns. The system 2500 includes an injector 2510 fluidically coupled to a pressure regulator 2505 through a supply line 2507. The injector 2510 is also fluidically coupled to a microfluidic device 2525 through a supply line 2512. The microfluidic device 2525 includes a port 2527 fluidically coupled to a midpoint pressure regulator 2530 through a port 2533. Gas is provided from the midpoint pressure regulator 2530 to the port 2533 through a supply line 2532. The microfluidic device 2525 includes ports 2535, 2540, 2545 and 2550. In the embodiment of FIG. 25, ports 2535 and 2540 are closed or plugged such that no gas flows into them. The port 2550 is fluidically coupled to a first column 2555. The port 2545 is fluidically coupled to a second column 2565. Each of the columns 2555 and 2565 is coupled to a detector 2560 and 2570, respectively. In operation, a sample is introduced into the injector 2510 and species in the sample can be separated using the first column 2555 and the second column 2565. The column media in columns 2555 and 2565 can be the same or can be different. Species elute from the columns and are passed to their respective detectors for detection. Flow control of the overall system may be performed as described herein or using other suitable algorithms. The arrows show the general gas flow in the system 2500. While not shown, the system of FIG. 25 may include a detector fluidically coupled to one of the ports 2535 or 2540. A restrictor or another column may be positioned between port 2535 or port 2540 and a detector.

Figure 26B:
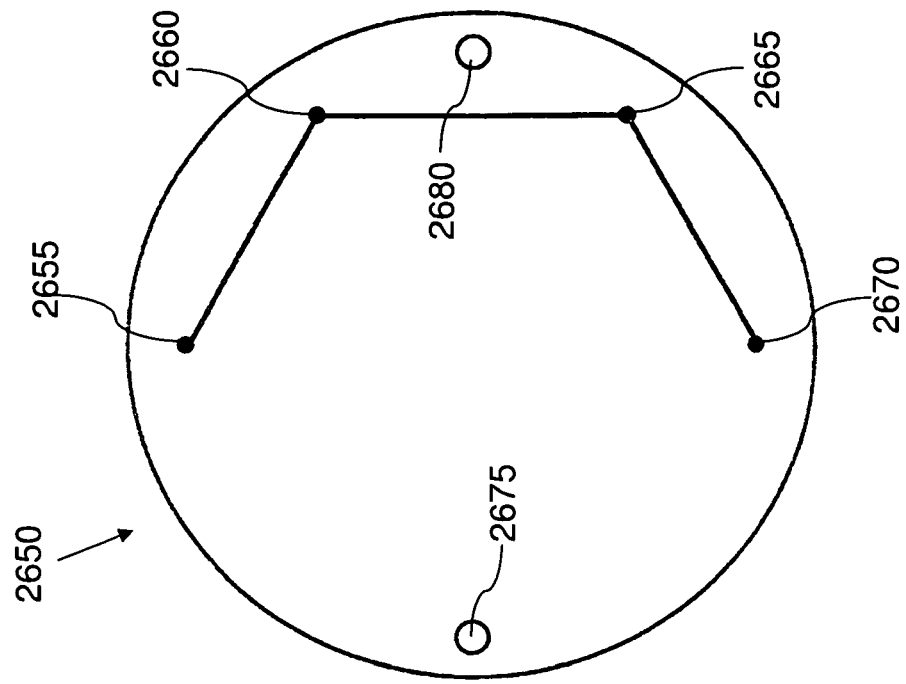
FIGS. 26A and 26B are illustrations of a microfluidic device that includes a microchannel where all the ports are arranged in series, in accordance with certain examples.
Figure 26A:
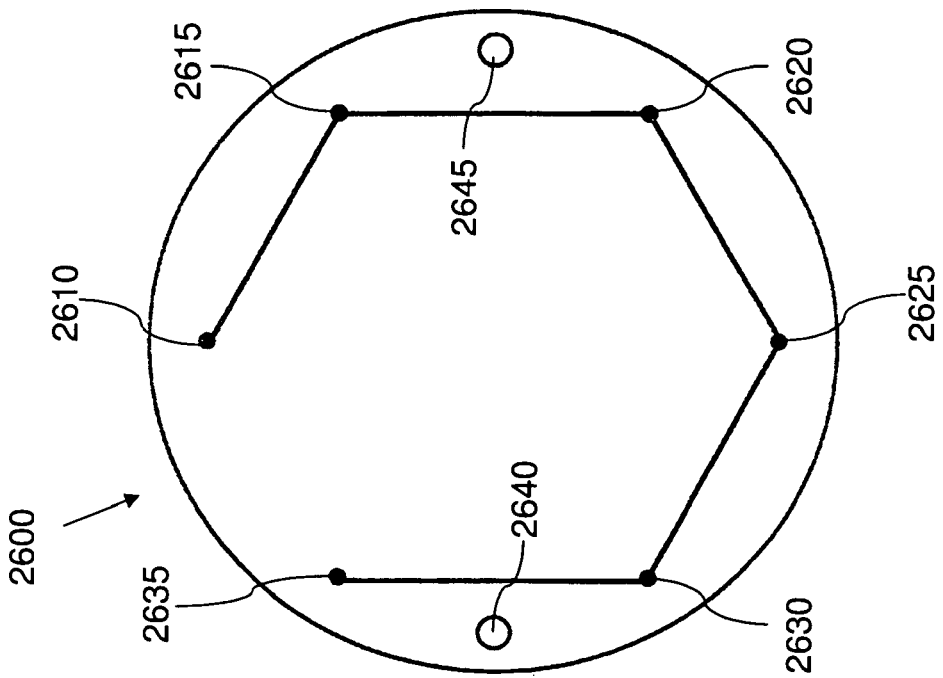

In certain examples, while the systems described above include a microfluidic device that is designed to be coupled to a midpoint pressure regulator, there are applications that are cost sensitive or do not need any gas added to the column effluent. When such applications are performed, a different microfluidic device can be used. Or in the alternative, the midpoint pressure port of the wafers shown in FIGS. 11-15B can be blocked or capped such that no gas flow can enter. One such configuration where the midpoint pressure port is omitted is shown in FIG. 26A. The microfluidic device 2600 includes serial ports 2610, 2615, 2620, 2625, 2630 and 2635. The microfluidic device is scalable in that all or fewer than all of the ports can be used. Apertures 2640 and 2645 may be used to attach the microfluidic device 2600 to a holder or other device. The port 2615 is downstream of where the column effluent enters the microfluidic device at the port 2610. The port 2615 may be connected to a gas inlet or this port can be capped or blocked. Each of the ports 2620, 2625, 2630 and 2635 may be fluidically coupled to a column, restrictor, detector and various combinations thereof. Where fewer than four couplings are desired, any one or more of the ports can be capped or plugged to shut that port off. In addition, a microfluidic device having fewer than six ports can be designed. One such example is shown in FIG. 26B. The microfluidic device 2650 includes ports 2655, 2660, 2665 and 2670. Apertures 2675 and 2680 may be used to attach the wafer 2650 to a holder or other device. The ports 2660, 2665 and 2670 can be fluidically coupled to a column, restrictor, detector and various combinations thereof. In one alternative, the port 2660 can be fluidically coupled to a gas source to provide additional gas through the wafer 2650. Other port numbers, configuration and geometries consistent with the microfluidic devices 2600 and 2650 may also be used depending on the desired number of detectors to be used in the system or the particular desired configuration of the system.

In accordance with certain examples, the microfluidic devices described herein include one or more microchannels in the wafer. The exact configuration of the microchannel and how such microchannels are produced can vary depending on the particular material selected for use as a wafer. For example, the microchannel can be chemically etched, laser etched, drilled, grinded or molded into the wafer during production. The widths and overall geometry of the microchannels may vary. In one embodiment, the width of the microchannels can vary from about 10 microns to about 750 microns, for example, 50 microns to about 500 microns, for example, about 10 microns to about 100 microns, about 100 microns to about 300 microns, or about 300 microns to about 500 microns. The cross-sectional geometry of the microchannel may be circular, elliptical, triangular or other geometries. As discussed herein, it is desirable, but not required, that the microchannels have smooth transitions, e.g., elbows and the like, to facilitate gas flow through the microchannels.

Figure 27:
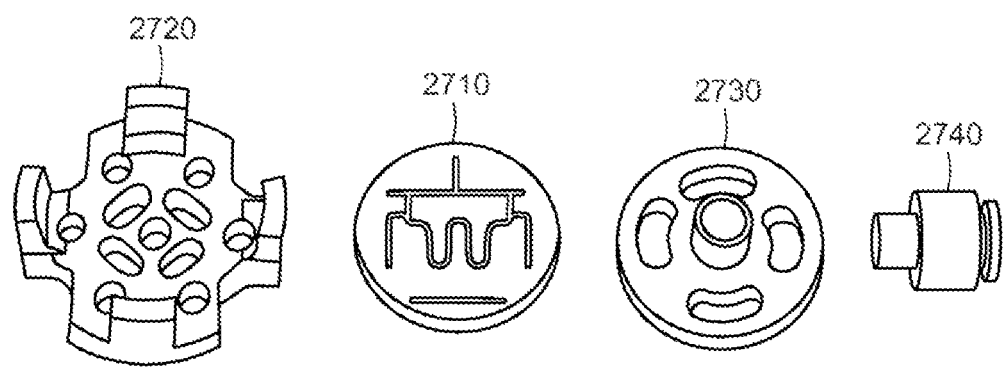
FIG. 27 is a photograph showing a microfluidic device and two plates to hold the microfluidic device, in accordance with certain examples.

In certain examples, the microfluidic device can be used in a multilayer device or a multicomponent device. For example, the microfluidic device can be sandwiched between two or more other devices to provide for a substantially fluid tight seal to prevent leaks. One or more gaskets or gasket materials can be used to further enhance the seal. Additionally, gaskets, tapes or other materials can be used at the ports of the device to provide additional sealing, if desired. In some examples, the microfluidic device can be a multi-layer structure itself, e.g., a laminated wafer, with sequential additions of layers being added to form the microchannels. One example of a microfluidic device and two plates used to hold the wafer is shown in FIG. 27. The wafer 2710 can be sandwiched between a first plate 2720 and a second plate 2730. A ferrule or fitting 2740 can be attached to the assembly to hold the microfluidic device 2710 and plates 2720, 2730 together during use of the microfluidic device.

In certain examples where the microfluidic device is configured as a wafer, the wafer can be produced from various materials including metals, plastics, composites, polymers, steels, stainless steels, alloys, and other materials that can be assembled to provide microchannels. For example, various layers of the wafer can be produced using stainless steel plates that can be laminated or welded together to form an overall microchannel structure within the wafer. In certain embodiments, layers of polyethertherketone or other polymers having a desired channel portion etched, drilled or otherwise carved into it can be laser or solvent welded to each other to provide the wafer. Regardless of the particular material selected for use in the wafer, the material desirably is inert such that no unwanted chemical reactions will occur between the sample and the wafer. In examples where the wafer material may be reactive, the microchannels (or the entire wafer surface) can be coated with an inert material such as, for example, polytetrafluoroethylene or other generally inert materials. Where the sample to be analyzed is corrosive, the microchannels (or the entire wafer surface) can be coated with yttria, alumina, or other materials that are resistant to corrosion and can protect the underlying wafer structure from damage. If a coating is used, the coating should be thick enough and robust enough to avoid leaching off, flaking or desorbing, which could lead to interference with the sample measurements. In addition, the materials used in the microfluidic device are desirably heat tolerant such that they do not melt or experience any substantial thermal deformation when used in a hot oven, such as those ovens and temperatures commonly encountered and used in chromatography system separations.

Figure 28:
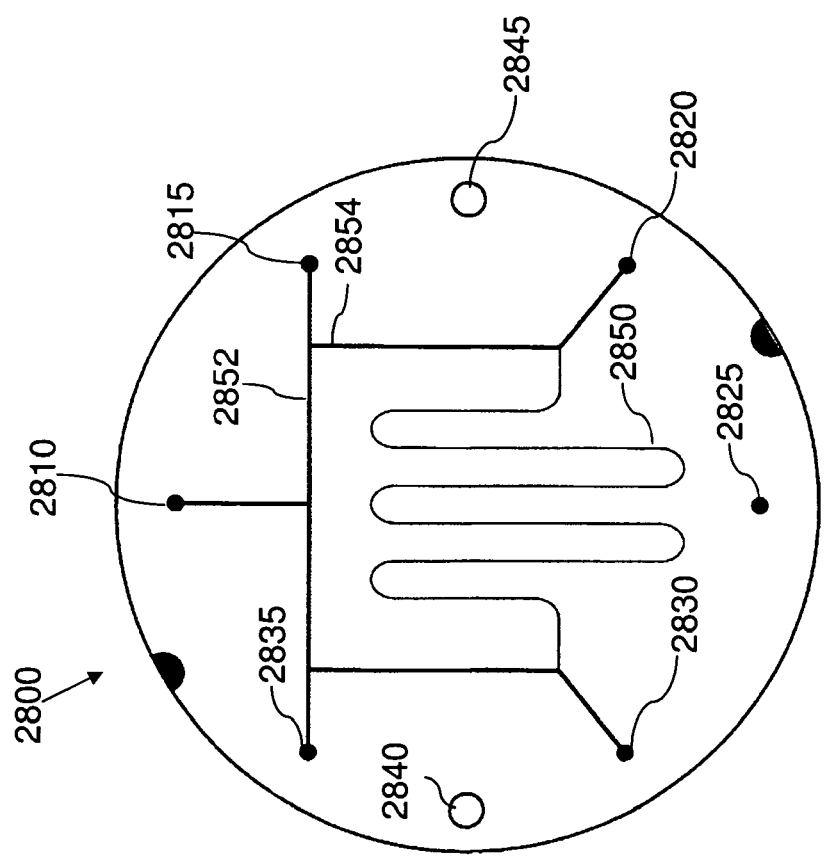
FIG. 28 is a cross-section of a microfluidic device showing an internal bypass restrictor, in accordance with certain examples.

In accordance with certain examples, the restrictors that can be used with the devices and systems disclosed herein may vary in configuration and design. In certain examples, the microfluidic devices described herein can include a bypass restrictor or other comparable device to reduce or restrict flow of gas and/or sample into unused areas of the microfluidic device. One such example is shown in FIG. 28. The microfluidic device 2800 includes a plurality of ports 2810, 2815, 2820, 2825, 2830, and 2835. The port 2810 provides effluent from the column. The port 2815 can be fluidically coupled to a first detector (optionally with an in-line restrictor). The port 2820 is fluidically coupled to a switching gas source. The port 2825 is not used in this configuration. The port 2830 is fluidically coupled to another switching gas source. The port 2835 is fluidically coupled to a second detector (optionally with an in-line restrictor). A fluid connection 2850, e.g., internal or external, may be provided between the ports 2820 and 2830 to by-pass the port 2825. The fluid connection 2850 may include an external needle valve or may include a valve such as, for example, a switching valve such as a solenoid valve. The bypass dimensions can be adjusted to ensure that substantially no diffusion of gas occurs into an unused portion of the wafer. In operation, sufficient gas flow is provided to the by-pass restrictor to prevent sample diffusion along the switching gas inlet channel not in use at a particular point in time. The flow rate is desirably low to avoid or reduce the volume of gas entering into the GC column, which can dilute the sample.

In certain examples, to reduce the flow rate through the microchannels, the switching gas channels can be narrowed, tapered or constricted near the ends to increase the gas velocity as it enters into the sample flow path. For example and referring to FIG. 28, at or near the union of microchannel sections 2852 and 2854, the diameter of the microchannel section 2854 may be less than that of the microchannel section 2852. For example, if the microchannel section 2852 is about 600 microns in diameter, the microchannel section 2854 can be reduced to 300 microns in diameter. It will be recognized by the person of ordinary skill in the art, given the benefit of this disclosure, that a 50% reduction is not required. Other percentages and ratios may be used. For example, the ratio of the unconstricted microchannel section diameter: constricted microchannel section diameter can be about 5:1 to about 1.1:1, e.g., 4:1, 3.5:1, 3:1, 2.5:1, 2:1, 1.5:1, 1.4:1, 1.3:1, 1.2:1, 1.1:1, more particularly about 3:1 to about 1.1:1, for example about 2.5:1 to about 1.2:1 or about 2:1 to about 1.5:1. In some examples, the overall diameter of the microchannel can be about 400-500 microns and constricted portions of the microchannel can have diameters of about 100-200 microns. The exact length of the bypass restrictor channel can also vary with illustrative lengths of about 5 mm to about 30 mm, more particularly about 10 mm to about 20 mm, e.g., about 11, 12, 13, 14, 15, 16, 17, 18, 19 mm or any value in between these specific lengths.

In accordance with certain examples, in assembly and use of the microfluidic devices described herein, the microfluidic device is typically sandwiched or encased in a multicomponent device to provide a microfluidic device that can be coupled to pneumatic tubing in a GC system. As described herein, these systems can be used in many different configurations and in multi-dimensional chromatographic analyses. In addition, while certain embodiments of the microfluidic devices are described herein, it will be recognized by the person of ordinary skill in the art, given the benefit of this disclosure, that the microfluidic devices can be used in combination with each other, e.g., by mounting them back to back in the same system. Suitable fluid connections to desired ports may be provided using pneumatic tubing and other connectors. In addition, crossover channels, e.g., either within one microfluidic device or between two or more different microfluidic devices can be provided. In-line valves or actuators can be used to control the gas flow to a desired port and/or to a desired microfluidic device. For example, a solenoid valve can be modulated, e.g., at about 10-100 Hz, e.g., about 50 Hz, to permit flow of one species to a desired port or detector. The solenoid valve may be closed or switched to stop such flow to a particular port. Some of these configurations are described in detail below.

Figure 29:
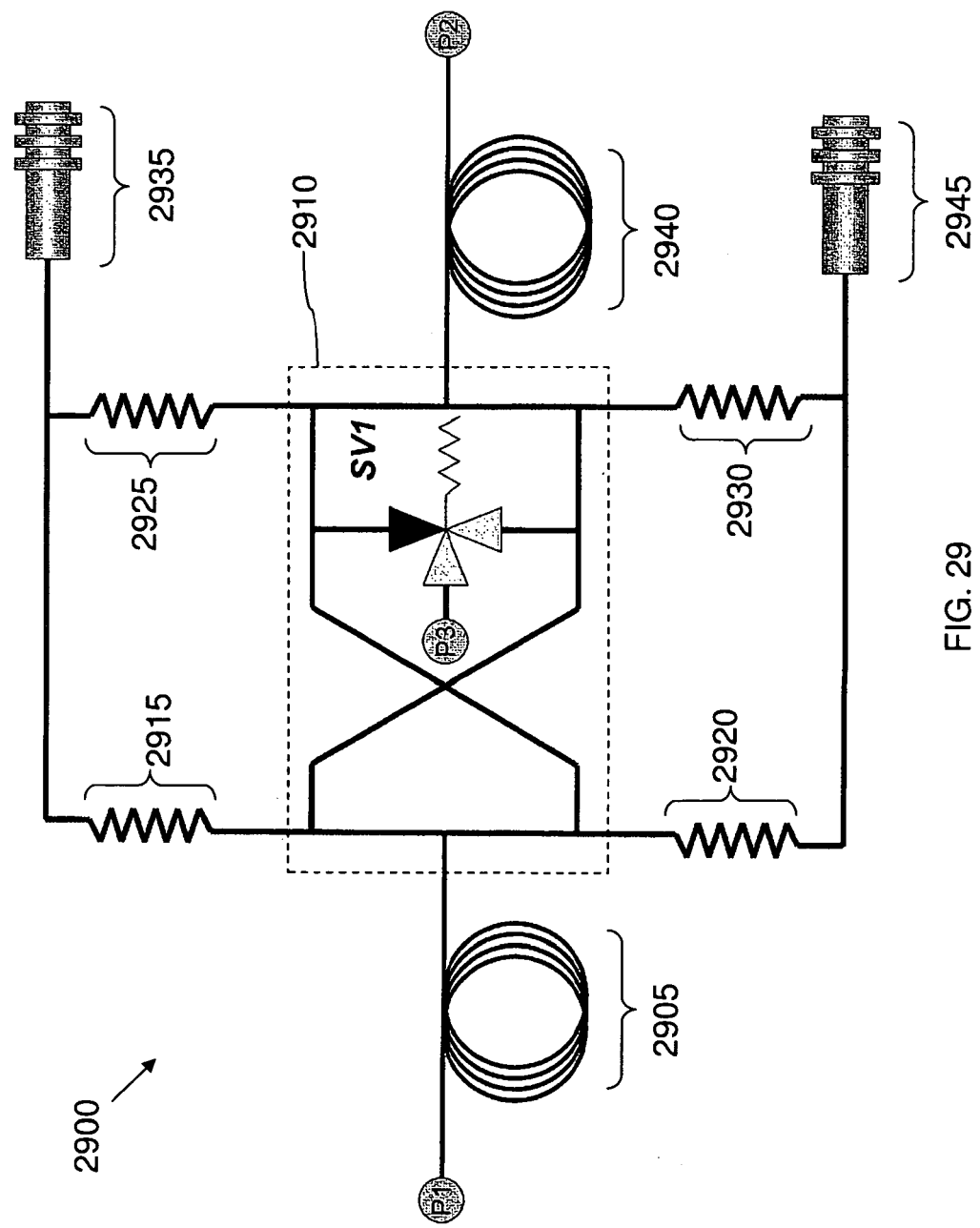
FIG. 29 is a schematic of a chromatography system that includes two columns and two detectors each fluidically coupled to a first and a second microfluidic device, in accordance with certain examples.

In certain examples and referring to FIG. 29, one example of a system including a microfluidic device with a crossover switch is shown. Use of a crossover switch may be particularly desirable where, for example, column switching, automated screening, backflushing, large volume injections, multi-dimensional chromatography or multiplexing operations are desired. For example, one MS detector can simultaneously receive sample from two different columns. The system 2900 includes an injector (not shown) fluidically coupled to a first column 2905. The first column 2905 is fluidically coupled to a microfluidic device 2910 through a fluid flow path, e.g., pneumatic tubing. The system also includes a plurality of restrictors 2915, 2920, 2925 and 2930 each fluidically coupled to the microfluidic device 2910. As discussed herein, the restrictors can be used to balance the pressure in the system. The microfluidic device 2910 includes a switching valve that is operative to provide a crossover path such that species from the first column 2905 and a second column 2940, which can be fluidically coupled to its own injector (not shown), can selectively be provided to a detector 2935 or a detector 2945. For example, by modulating the switching valve, a fluid flow path can be provided between two or more desired components of the system and can provide different species eluting from either column to one or both of the detectors. In addition, the sample flow can be split such that effluent from one column is provided to both of the detectors 2935 and 2945, as described herein. The various pressures in the system can be balanced as described herein or using other suitable configurations. It is desirable that the columns have the same internal diameter but the lengths can be different. The injectors can be liquid injectors or other suitable injectors, e.g., high speed injectors, automatic thermal desorption injectors and other injectors commonly used with GC devices and systems. The detectors 2935 and 2945 may be the same or may be different. Desirably, one of the detectors can be a MS detector and the other may be a different detector such as, for example, those described herein.

In certain embodiments, two or more microfluidic devices can be used in the illustrative embodiment of FIG. 29. For example, a crossover connection can be provided between two or more microfluidic devices each fluidically coupled to at least one column. For example, a first microfluidic device can be fluidically coupled to the first column 2905, and a second microfluidic device can be fluidically coupled to the second column 2940. The switching valve can be actuated to provide desired flow to a particular port of the microfluidic device or to provide flow between the microfluidic devices.

Figure 30A:
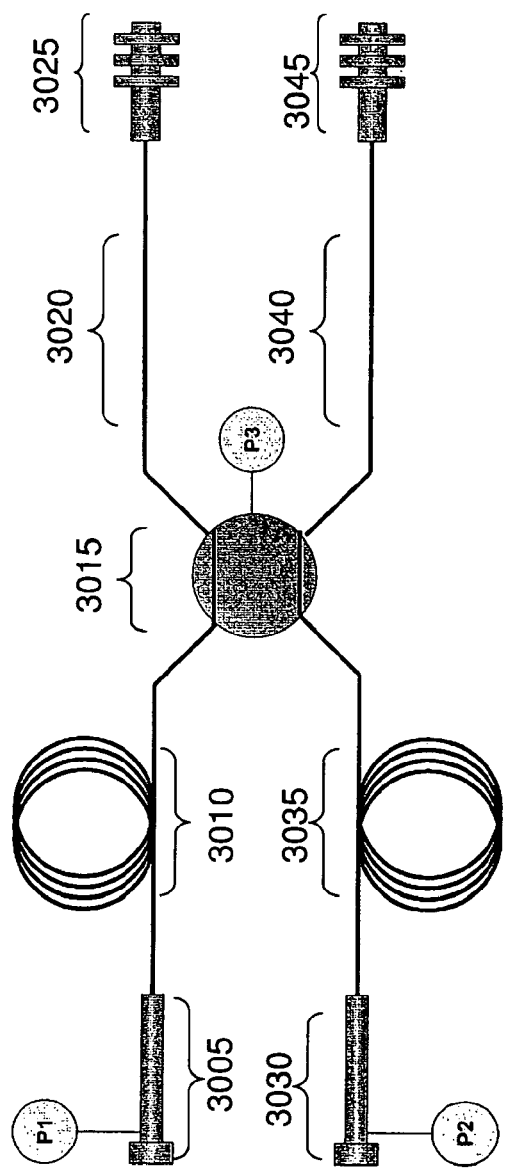
FIGS. 30A and 30B are schematics of a chromatography system with a microfluidic device that can provide for crossover flow, in accordance with certain examples.
Figure 30B:
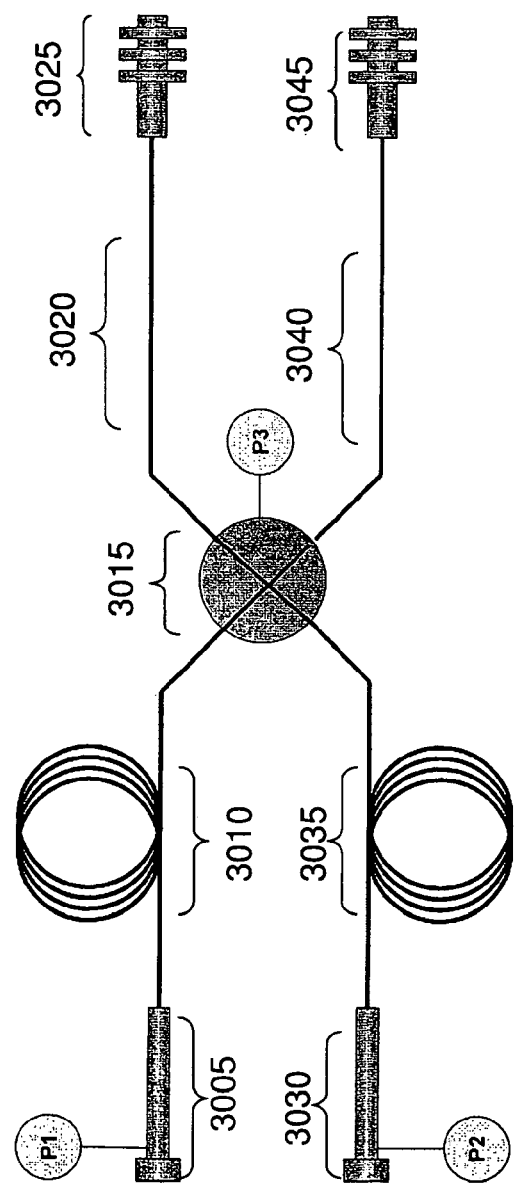

Various possible connections between the components of FIG. 29 are shown in more detail in FIGS. 30A and 30B. Referring to FIG. 30A, the switching valve of the microfluidic device 3015 may be configured such that effluent from a column 3010 is provided to a detector 3025. An injector 3005 is fluidically coupled to the column 3010. An in-line restrictor 3020 is between the microfluidic device 3015 and the detector 3025. An injector 3030 provides sample to a second column 3035. The microfluidic device 3015 is also fluidically coupled to the second column 3035. The microfluidic device 3015 is fluidically coupled to a second detector 3045 through a restrictor 3040. In the configuration shown in FIG. 30A, the microfluidic device 3015 is configured such that effluent from the column 3010 is provided to the detector 3025 and effluent from the column 3035 is provided to the detector 3045. In the crossover configuration shown in FIG. 30B, effluent from the column 3035 is provided to the detector 3025 and effluent from the column 3010 is provided to the detector 3045. In operation of the system, the microfluidic device may be operated between these two different states such that certain species from the column 3010 can be provided to the detector 3025 and other species from the column 3010 can be provided to the detector 3045. Similar operations may be performed for species exiting the column 3035. If desired, sample from the different columns 3010, 3035 can be provided to the same detector using the microfluidic device. In addition, more than one microfluidic device can be used in the system of FIG. 30, if desired.

In certain examples, the microfluidic device 3015 can also be used to backflush one or both of the columns 3010 and 3035. For example, by lowering the gas flow from pressure regulators $p_1$ and $p_2$ to be less than the flow from pressure regulator $p_3$, both of the column 3010 and 3035 can be backflushed for cleaning. In an alternative configuration, only the pressure $p_1$ or $p_2$ can be lowered to be less than $p_3$ such that only one of the columns is backflushed and separation may continue using the other column.

Figure 31:
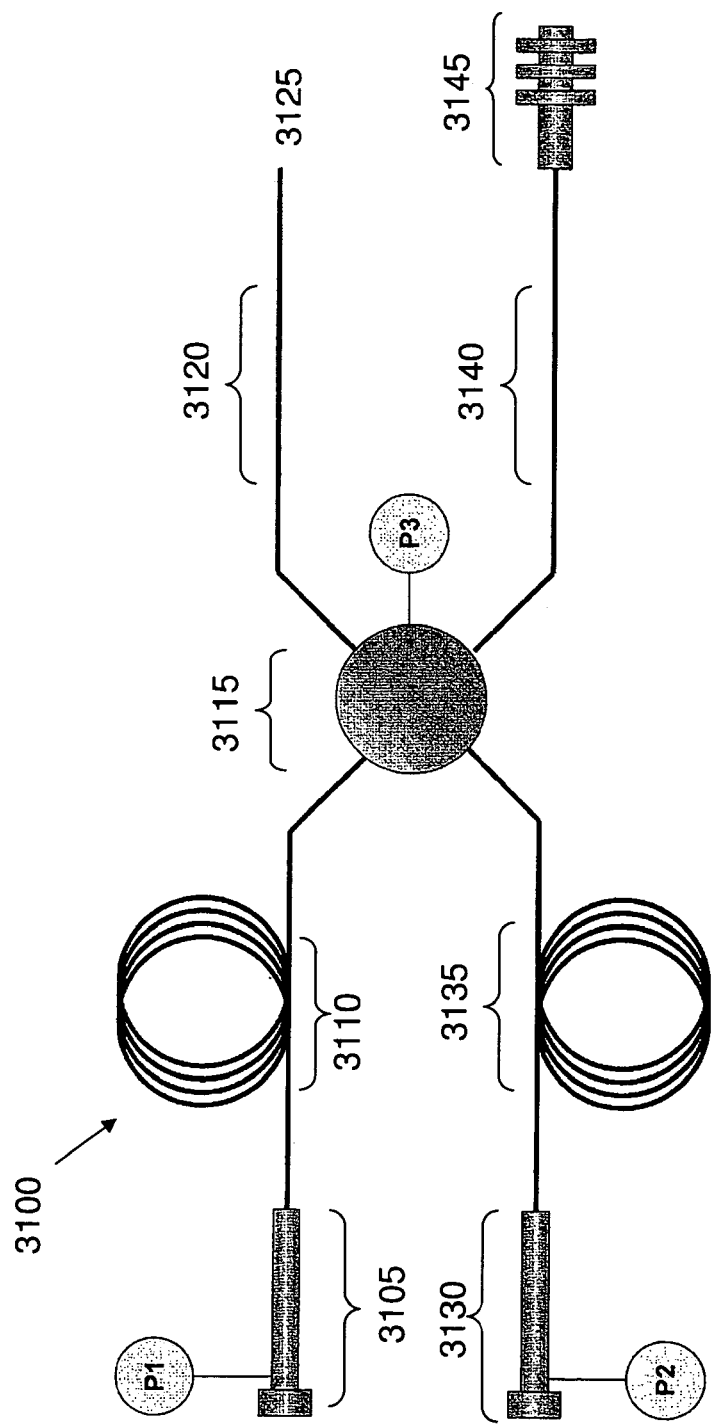
FIG. 31 is a schematic of another chromatography system with a microfluidic device that can provide for crossover flow, in accordance with certain examples.

In certain examples, one of the detectors shown in FIGS. 30A and 30B may be omitted or substituted with another device such as another column, a vent or other components commonly used in chromatography systems. One configuration is shown in FIG. 31. The system 3100 includes an injector 3105 fluidically coupled to a first column 3110. The column 3110 is fluidically coupled to a microfluidic device 3115. A vent 3125 is in fluid communication with the microfluidic device 3115 through a restrictor 3120. A second injector 3130 is fluidically coupled to a second column 3135. The second column 3135 is fluidically coupled to the microfluidic device 3115. The microfluidic device 3115 is also fluidically coupled to a detector 3145 through a restrictor 3140. In operation of the system 3100, the microfluidic device can be used to provide column effluent from both the column 3110 and the column 3135 to the detector 3145. Where species eluting from the column are not desired for analysis, the microfluidic device can be used to divert those species to the vent 3125. In an alternative configuration, the vent 3125 permits venting of the system while permitting the detector 3145 to be maintained at normal operating temperature and pressure. This feature is particularly desirable where the detector 3145 is a mass spectrometer.

Figure 32B:
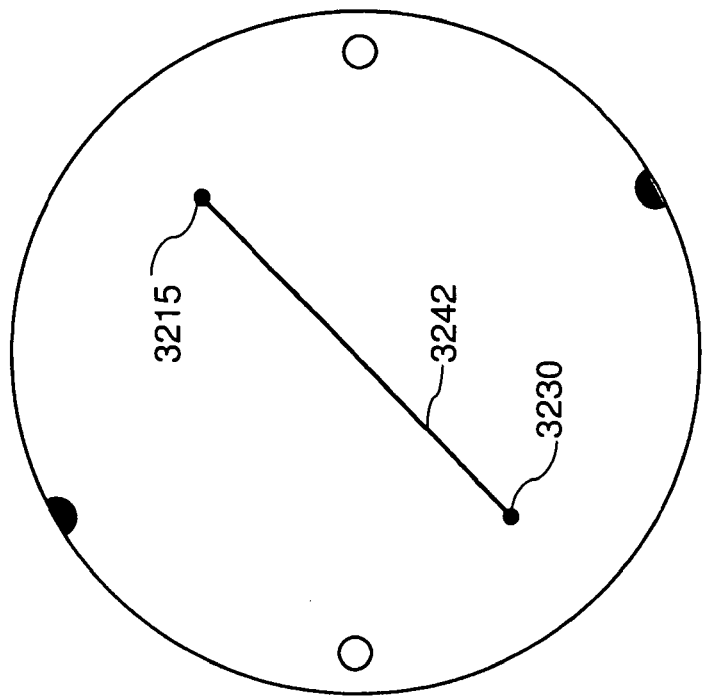
FIGS. 32A-32D are cross-section sections showing the various layers of the microfluidic device, in accordance with certain examples.
Figure 32A:
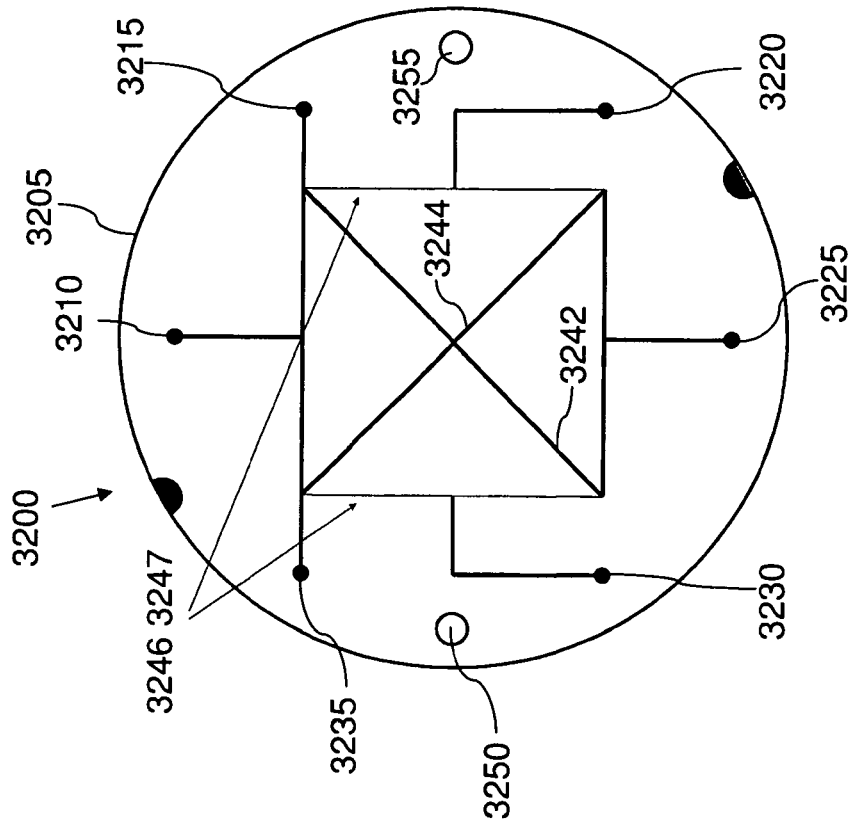
Figure 32D:
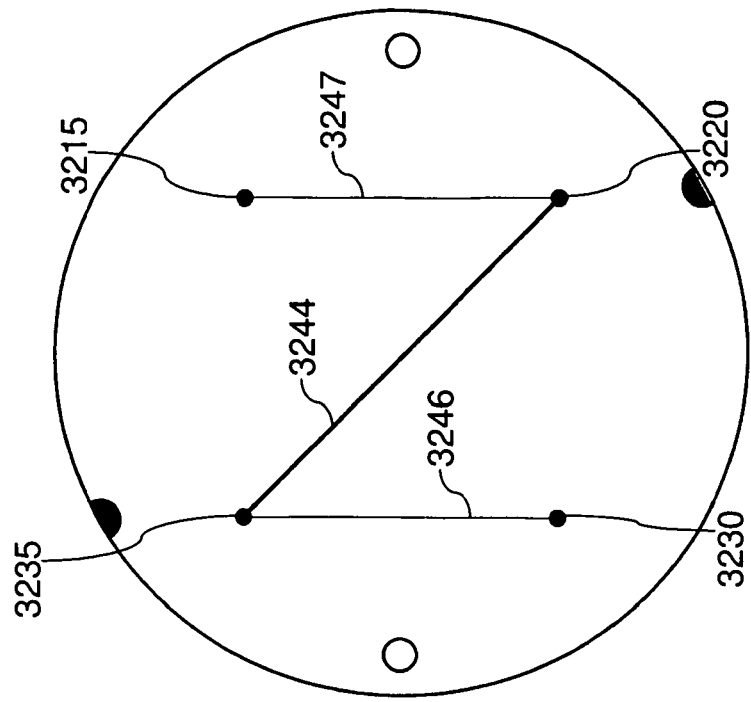
Figure 32C:
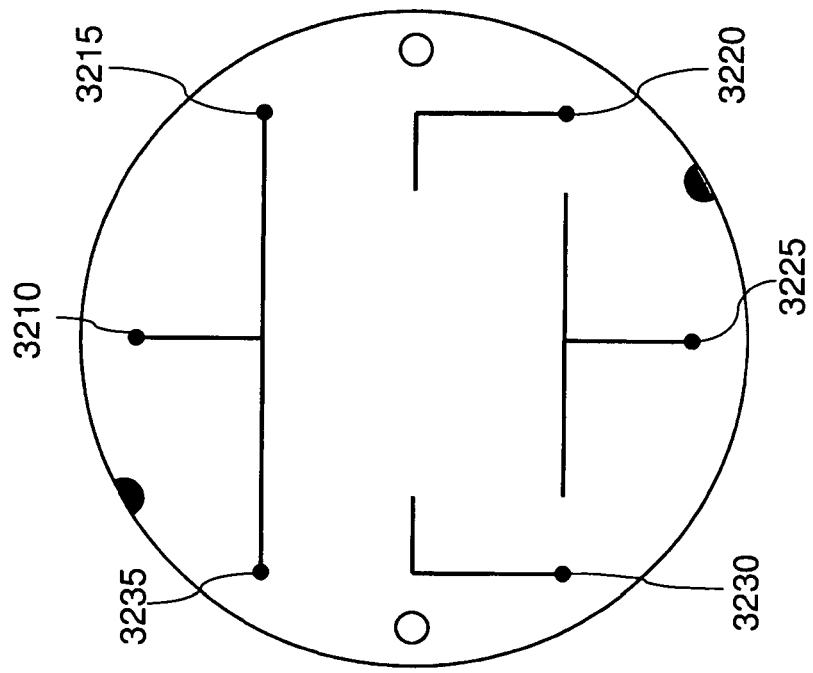

In accordance with certain examples, one illustration of a microfluidic device configured as a wafer and including a crossover flow path is shown in FIGS. 32A-32D. The overall wafer construct is shown in FIG. 32A with various layers shown exploded in FIGS. 32B-32D. Referring to FIG. 32A, the wafer 3200 generally includes a multilayer substrate 3205 having one or more microchannels therein. In this embodiment, the microchannel has six ports 3210, 3215, 3220, 3225, 3230, and 3235. The port 3210 can be an inlet port from a first column, the port 3230 can be a port for a first switching gas, the port 3220 can be a port for a second switching gas, the port 3235 can be an outlet port to a first detector, the port 3225 can be an inlet port from a second column, and the port 3215 can be an outlet port to a second detector (or vent). The device includes crossover channels 3242 and 3244 and constricted channels 3246 and 3247. In producing the wafer, different layers can be assembled to provide the various flow paths. Referring to FIG. 32B, one layer can provide the crossover path 3242, which provides fluidic coupling between ports 3215 and 3230. The layer shown in FIG. 32B can be the bottom layer of the laminate or a layer on an external surface of the laminate depending on the exact orientation of the microfluidic device. Another layer (see FIG. 32D), can provide the crossover path 3244 and the constricted channels 3246 and 3247. The layer shown in FIG. 32D can be the top layer of the laminate or a layer on an external surface of the laminate opposite to the layer shown in FIG. 32B with the middle layer positioned between the top layer and the bottom layer. The crossover path 3244 can provide for fluidic coupling between the ports 3220 and 3235. The constricted channel 3246 provides fluidic coupling between the ports 3230 and 3235. The constricted channel 3247 provides fluidic coupling between the ports 3215 and 3220. The middle layer (FIG. 32C) may include suitable flow paths to complete the microchannel and to provide fluid flow between desired ports of the microfluidic device. When the various layers are laminated together to provide a wafer, the fluid flow paths will be produced and can be used to control the direction of species in the chromatographic system. The overall wafer can be mounted to a sample holder or other suitable device using apertures 3250 and 3255 and suitable fittings, e.g., screws, nuts, bolts, ferrules, etc. Each of the various layers shown in FIGS. 32B-32D may itself be a multilayer structure or laminate or may be a generally solid body having respective microchannels etched or otherwise included therein. Gaskets, sealants or other materials may be added between the layers to facilitate a fluid tight seal to avoid or reduce the likelihood that internal leaks may occur.

In certain examples and as discussed herein, the microfluidic device may include one or more actuators or switching valves that can couple or decouple two or more fluid flow paths. The position of the actuator provides for fluid flow between two or more ports or prevents fluid flow between two or more ports. The microfluidic device may include a low cost solenoid valve that can be opened, closed or modulated at a desired frequency to connect two or more flow paths or to stop flow between two or more flow paths. In some examples, the solenoid valve can be actuated between a fully open and a fully closed position. The frequency with which the solenoid is actuated depends on the particular type of chromatography being performed, e.g., heartcut or solvent dump, the particular ports to be connected and the desired effect on pressure that can be accomplished by opening and closing the valve, and illustrative frequencies include, but are not limited to 5-200 Hz, 10-100 Hz, 20-90 Hz, 30-80 Hz, 40-70 Hz, 45-65 Hz, and 50-60 Hz. The solenoid valves are typically external to the wafer and coupled to a desired port through pneumatic tubing or other suitable connections. In some examples, the switching valve may be integrated into the port of the wafer to provide for fewer components for the end user to connect.

In certain embodiments, two or more serially connected switching valves can be used which are the same or are different. For example, a solenoid valve in-line with a proportional valve can be fluidically coupled to a port of the microfluidic device. The system may include gas flow monitors, pressure transducers or other devices to ensure that the pressure in the system is balanced.

Figure 33A:
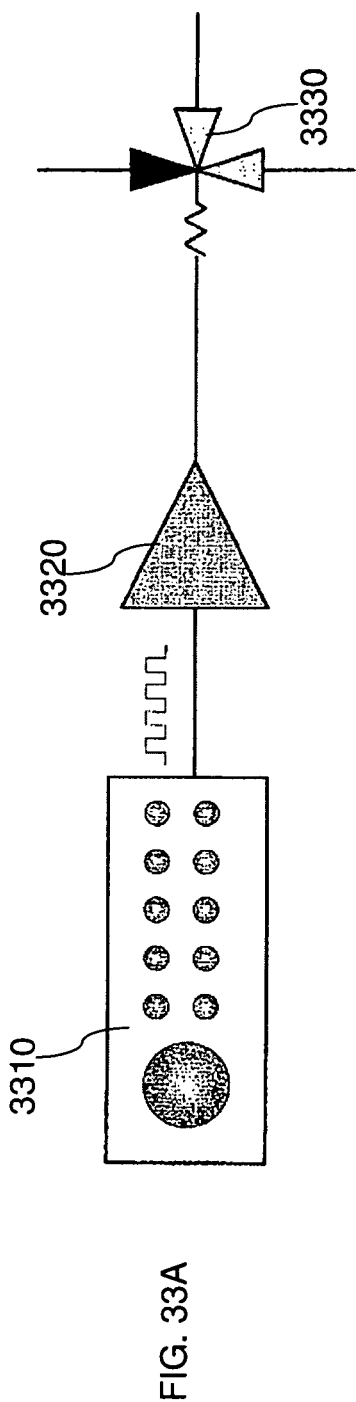
FIGS. 33A and 33B show a controller that can be used to actuate a switching valve, in accordance with certain examples.
Figure 33B:
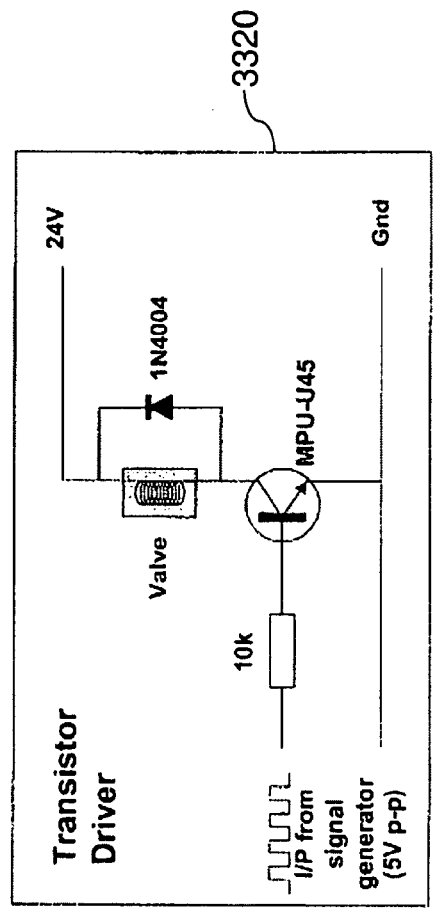

In certain examples, the switching valve can be controlled using a controller, processor or other suitable electrical components. One configuration that can be used to modulate the valve is shown in FIGS. 33A and 33B. Referring to FIG. 33A, a function generator 3310 is electrically coupled to a transistor driver 3320 and is operative to provide a desired waveform to the transistor driver 3320. The transistor driver 3320 is electrically coupled to a solenoid valve 3330 and is operative to modulate the solenoid valve 3330 at a frequency corresponding to the particular waveform provided by the function generator 3310. The waveform provided by the function generator 3310 can vary during the course of a separation depending, for example, on the desired cycle frequency. In certain examples, a square wave can be provided by the function generator 3310 such that the solenoid valve 3330 will cycle between an open and a closed position, with respect to a given outlet. For example, where a 3-way solenoid valve is used, it can switch the inlet flow between two different outlets and thus can be "on" with respect to one of the outlets and can be "off" with respect to the other outlet. Other waveforms, e.g., triangular, sinusoidal, sawtooth and the like, can also be used depending in the particular type of switching valve fluidically coupled to the wafer. In certain embodiments, each port of the microfluidic device may include an individually controllable solenoid valve electrically coupled to a controller and a gas source such that fluid flow through each port can be individually controlled.

Figure 34:
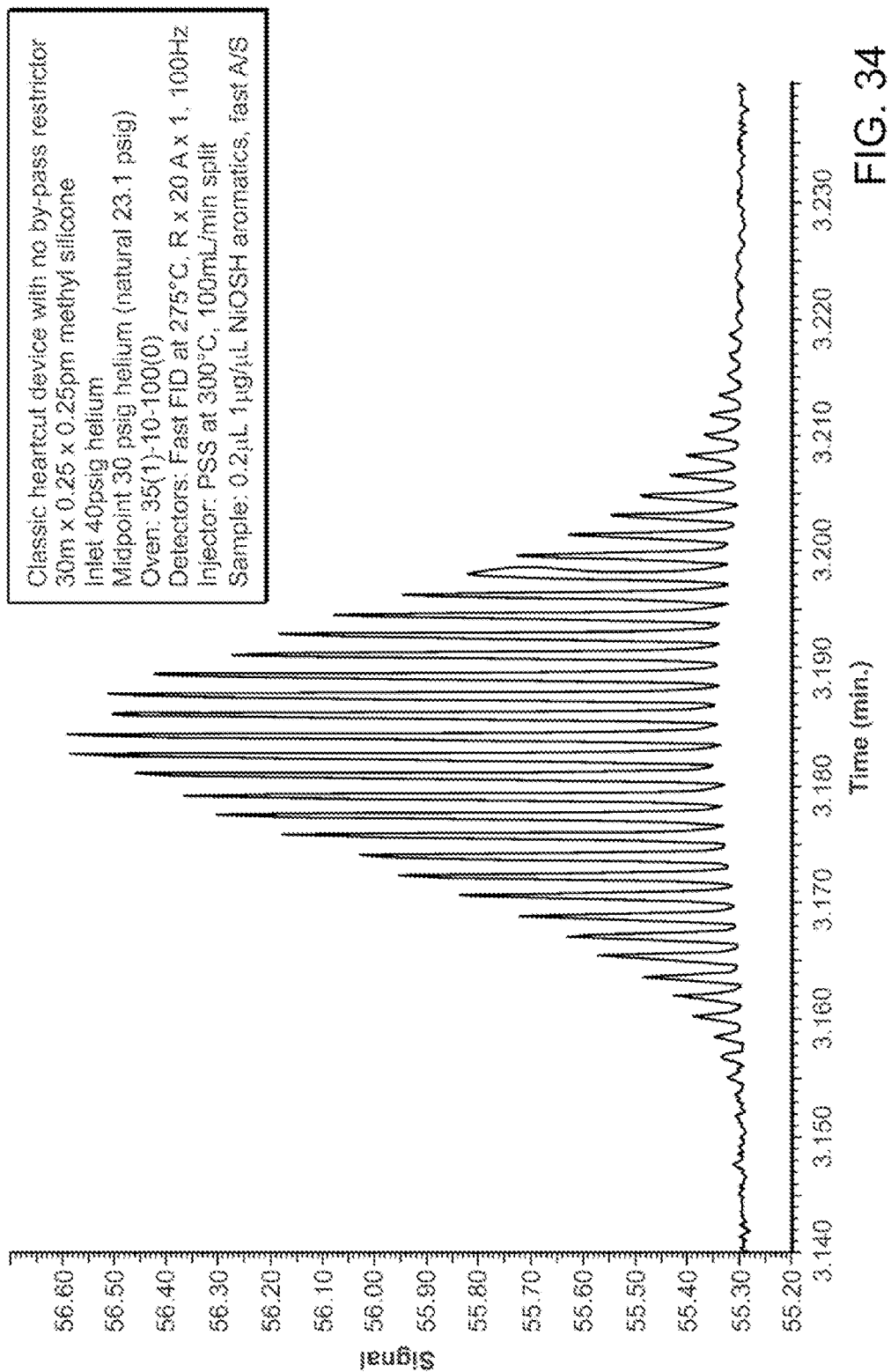
FIG. 34 is a graph showing the results of a single peak that has been modulated, in accordance with certain examples.

In certain embodiments, the microfluidic devices disclosed herein can permit simultaneous analysis of two chromatograms. Referring to FIG. 36 (FIGS. 34 and 35 are described below), a system 3600 is shown that includes a first injector 3610 fluidically coupled to a first column 3615. The system 3600 also includes a second injector 3620 fluidically coupled to a second column 3625. Each of the first column 3615 and the second column 3625 are fluidically coupled to a microfluidic device 3630. The microfluidic device 3630 is fluidically coupled to a vent 3640 through a restrictor 3635. The microfluidic device 3630 is also fluidically coupled to a MS detector 3650 through a restrictor 3645. The MS detector 3650 is electrically coupled to a solenoid valve (not shown) between a gas source 3655 and the microfluidic device 3630. The MS detector 3650 drives the midpoint solenoid valve modulation to synchronize the microfluidic device 3630 with the scanning of the MS detector 3650. Species eluting from both the first column 3615 and the second column 3625 can be directed to the MS detector 3650 using the microfluidic device 3630. Such direction permits simultaneous processing of two chromatograms. The exact configuration of the microfluidic device 3630 may be any of the illustrative configurations described herein or other suitable configurations.

In certain embodiments, a system configured to perform simultaneous confirmatory chromatography is shown in FIG. 37. The system 3700 includes an injector 3710 fluidically coupled to each of a first column 3715 and a second column 3720. The injector 3710 splits the sample flow such that a portion is provided to the first column 3715 and a portion is provided to the second column 3720. Each of the first column 3715 and the second column 3720 is fluidically coupled to a microfluidic device 3725. The microfluidic device 3725 is fluidically coupled to a vent 3735 through a restrictor 3730 and to a detector 3745 through a restrictor 3740. If the separation media in the columns and column internal diameters are the same, then the separation by each of the columns should be substantially the same. The switch 3725 can provide peaks from both the first column 3715 and the second column 3720 to the detector 3745 such as, for example, a MS detector. The system can be vented through the vent 3735 while the detector 3745 is kept at an operating temperature and pressure In certain examples, an illustrative system configured for multidimensional separations and multiplexed detection is shown in FIG. 38. The system 3800 includes an injector 3810 fluidically coupled to a column 3815 and a carrier gas source 3805. The column 3815 is fluidically coupled to a first microfluidic device 3820 which is coupled to a gas source 3822. The first microfluidic device 3820 is also fluidically coupled to a second column 3825 and a second microfluidic device 3830. A restrictor 3827 is between the first microfluidic device 3820 and the second microfluidic device 3830. The second microfluidic device 3830 is fluidically coupled to a gas source 3835. The second microfluidic device 3830 is also fluidically coupled to a vent 3845 and a detector 3855. Peaks can elute from the first column 3815 and can be provided to the second column 3825 or can be provided to the detector 3855 or the vent 3845 using the first microfluidic device 3820 and the second microfluidic device 3830. Peaks may be selectively provided to a desired component based on the particular ports fluidically coupled within each of the first and second microfluidic devices 3820 and 3830, respectively. The first microfluidic device 3820 and second microfluidic device 3830 need not be the same but they may be the same. In some examples, the first and second microfluidic devices are selected to be different to provide for increased control of sample eluting from the column or columns.

In certain embodiments and referring to FIG. 39, a dual column, single detector configuration is shown. The system 3900 includes a first column 3910 and a second column 3920 each fluidically coupled to a gas source 3905 and 3915, respectively. Each of the first and second columns is also fluidically coupled to a microfluidic device 3925. The microfluidic device 3925 includes a first buffer 3932 and a second buffer 3934. The term buffer is used interchangeably in certain instances with the term charging chamber. The first buffer 3932 and the second buffer 3934 can each be used to retain peaks from the columns. For example, species can elute from the column 3910 and be collected in the first buffer 3932. Once collected, the species can be directed to the detector 3945 through a restrictor 3940 using a switching gas from a gas source 3930 and a switching valve 3927. Simultaneously, species eluting from the second column 3920 can be collected in the second buffer 3934. After the species from the first buffer 3932 have been provided to the detector 3945, the valve 3927 can be switched such that the sample in the second buffer 3934 is now directed to the detector 3945 using the switching gas. The capacity of the buffers 3932, 3934 is desirably matched and of a sufficient volume for the column effluent flow rates and for the multiplexing frequency. For example, the buffers may each be from about 80 microliters to about 150 microliters, for example about 120 microliters, which is suitable for use with a column effluent rate of about 1 milliliter per minute at a multiplexing frequency of about 10 Hz. Other suitable column effluent rates and multiplexing frequencies will be selected by the person of ordinary skill in the art, given the benefit of this disclosure.

In certain examples, a wafer that includes a buffer is shown in more detail in FIG. 40. The wafer 4000 includes a plurality of ports and two buffers. A port 4010 is fluidically coupled to a first buffer 4012 and to a second port 4015. The buffer 4012 is inline between the port 4010 and a port 4020. A second buffer 4022 is inline between the ports 4025 and 4030. The buffers 4012 and 4022 can be part of the microchannel but are larger in diameter. In particular, the diameters and lengths of the buffers can be selected to be of sufficient capacity to accommodate the effluent flowing from a column, at the applied mid-point pressure, during one cycle of the modulated switching valve. In certain examples, the length and width of the buffer can be selected so that the buffer fits inside the wafer and still provides a desired fluid capacity. In operation, the port 4010 can be fluidically coupled to a switching gas source, the port 4015 can be fluidically coupled to a first column to receive effluent from the first column, the port 4020 can be fluidically coupled to a detector to provide sample to the detector, the port 4025 can be fluidically coupled to another column to receive effluent from the second column, and the port 4030 can be fluidically coupled to another switching gas source. As discussed in more detail below, the buffers can be used along with flow control to reduce diffusional broadening of peaks.

Figure 43B:
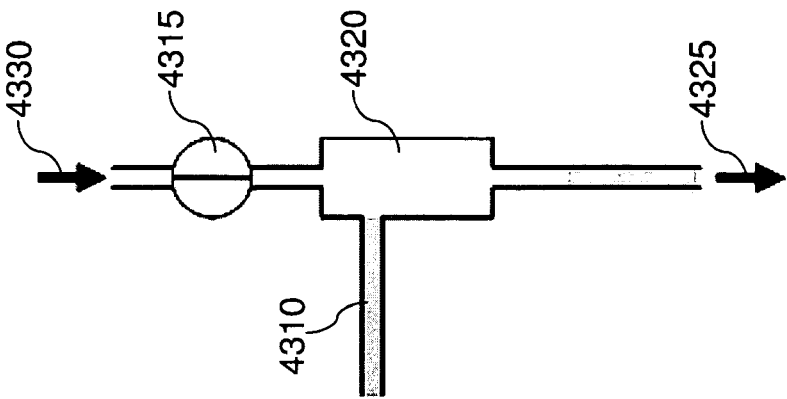
FIGS. 43A and 43B show flow of fluid through a charging chamber using a 2-way switching valve, in accordance with certain examples.

In certain embodiments, the devices described herein can be used to provide flow modulation. Flow modulation can provide substantial benefits including improved peak detection. A typical chromatogram is shown in FIG. 41, in which the response is related to either the flow rate (for mass flow detectors) or the concentration (concentration dependent detectors) of analytes flowing through a detector. When flow modulation is used for the same sample used in FIG. 41, the signal should appear closer to that shown in FIG. 42. The flow modulation allows the column effluent which is normally flowing at a slow rate (e.g. 1 mL/min) to flow into a chamber. For example, referring to FIG. 43A, column effluent 4305 can flow from a column to a fluid flow path 4310 and into a buffer or charging chamber 4320. When a switching valve 4315 is in a first position, the column effluent 4305 will have a tendency to build up in the charging chamber 4320, though some may exit the charging chamber and be provided to a detector in the direction of arrow 4325. Referring now to FIG. 43B, when the switching valve 4315 is actuated to a second position, a modulating gas will be provided in the direction of arrow 4330. The flow rate of the modulating gas exceeds the flow rate of column effluent. This large difference in flow rate acts to push any column effluent 4305 in the charging chamber 4320 to the detector in a single large pulse or bolus. This process results in a large, narrow peak as shown in FIG. 42. In particular, this modulation has the effect of introducing narrow bands of column effluent into the detector separated by the clean modulating carrier gas as shown in FIG. 42. The signal processing system desirably synchronizes discrete detector readings with the flow modulation so that these readings are taken at the apexes of the pulses. Detector readings can also be taken in between the pulses to obtain a background signal. Several advantages can be obtained using flow modulation optionally along with the microfluidic devices described herein. For example, with mass-flow sensitive detectors, the mass flow of analyte may be increased by a factor of 50× or more giving rise to greater sensitivity and, improved detection limits. With concentration dependent detectors, the modulation may enable the column effluent to travel through the detector cell at a high rate but with little dilution. This result may enable relatively large cell detectors to be used with narrow bore columns without the loss in sensitivity normally associated with the use of a make-up gas. The ability to monitor the detector background signal between the pulses may help eliminate the effects of detector drift and improve detection limits and analytical stability. There may be opportunities to use a modulator with a conventional flame photometric detector to enable time-gating of the optical emissions from the flame subsequent to each pulse to improve selectivity and reduce noise—in a similar way as achieved using, for example, certain pulsed flame photometric detectors. Also, a good flow modulator may form the basis of a GCxGC system.

Figure 43A:
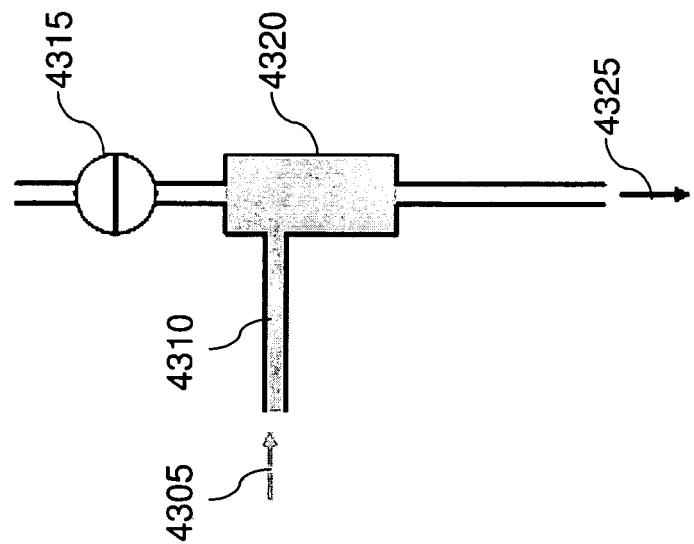
Figure 44B:
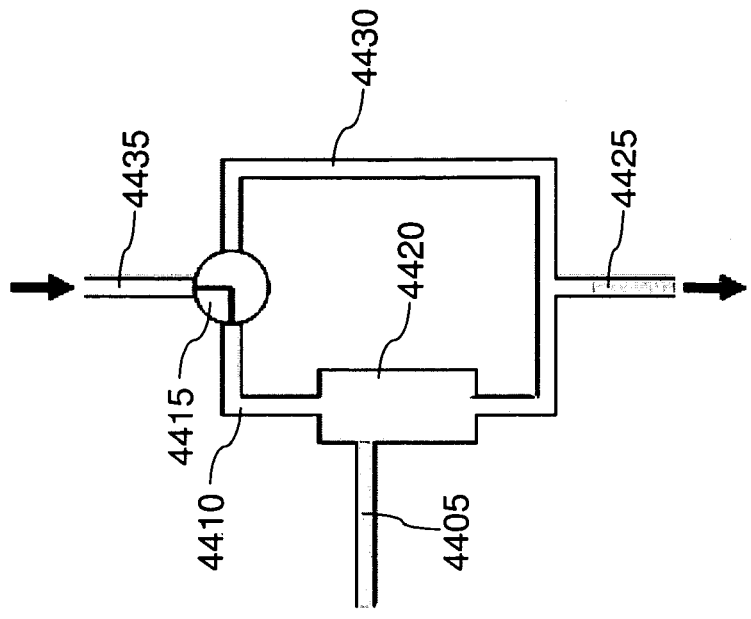
FIGS. 44A and 44B show flow of fluid through a charging chamber using a 3-way switching valve, in accordance with certain examples.
Figure 44A:
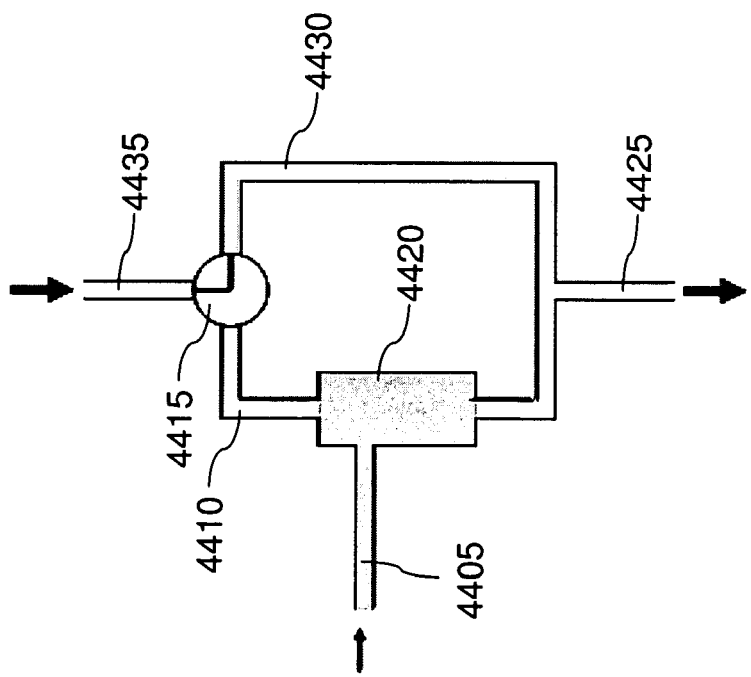

In certain embodiments, the charging chamber shown in FIGS. 43A and 43B may have some limitations. In FIG. 43A, the switching valve prevents flow of a modulating gas into the charging chamber 4320 and so the flow rate of gas into the detector will be that of the column effluent. When the switching valve is actuated to a second position, there is a sudden increase in the flow rate entering the detector. This slow-fast-slow flow rate of carrier gas can lead to noise and instability in the detector. If such noise is present, a 3-way switching valve can be used as shown in FIGS. 44A and 44B to provide a more stable flow rate of gas into the detector. Referring to FIGS. 44A and 44B, a device includes a charging chamber 4420 fluidically coupled to a column (not shown) through a fluid flow path 4405. The device also includes a fluid flow path 4410 between a 3-way switching valve 4415 and the charging chamber 4420. A by-pass flow path 4430 is also fluidically coupled to the 3-way switching valve 4415. When the 3-way switching valve 4415 fluidically couples a modulating gas from fluid flow path 4435 to the by-pass flow path 4430 (FIG. 44A), modulating gas travels into the by-pass flow path and out to a detector through fluid flow path 4425. In this state, effluent from the column can build up in the charging chamber 4420. When the 3-way switching valve is actuated to a different position (FIG. 44B), the modulating gas can be provided to the charging chamber 4420 through the fluid flow path 4410 and can act to force the accumulated effluent from the charging chamber to the detector along the fluid flow path 4425. One cycle of the 3-way switching valve will produce one pulse into the detector. Thus to generate, for example, fifty pulses each second, the 3-way switching valve must oscillate at 50 Hz. This high level of cycling can place significant stress on the switching valve. In addition, while the chamber is being flushed as shown in FIGS. 43B and 44B, column effluent will continue to enter the chamber. This material will be diluted and effectively lost from the analysis.

In certain embodiments, more than one charging chamber can be used in the flow modulation methods described herein and the microfluidic devices described herein. An illustration of this configuration is shown in FIGS. 45A and 45B. The device includes a 3-way switching valve 4515 fluidically coupled to a modulating gas through a fluid flow path 4510. The switching valve 4515 is fluidically coupled to a first chamber 4525 through a fluid flow path 4520 and to a second chamber 4540 through a fluid flow path 4535. A column (not shown) is fluidically coupled to each of the first chamber 4525 and the second chamber 4540 through an inlet 4505. The chamber 4525 is fluidically coupled to a detector (not shown) through fluid flow paths 4530 and 4550, and the chamber 4540 is fluidically coupled to the detector through fluid flow paths 4545 and 4550. While one of the chambers 4525, 4540 is being charged, the other chamber is being flushed with the modulating gas. This arrangement should generate two pulses for each cycle of the switching valve, which permits the switching valve to oscillate at half the speed as the single chamber design to achieve the same performance. In addition, none of the column effluent is wasted—it is always charging one of the chambers. A small flow of the modulating gas between the chambers can prevent or reduce diffusion of sample vapor into the chamber being swept. The flow rate to the detector will be the same in either position of the switching valve.

Figure 46:
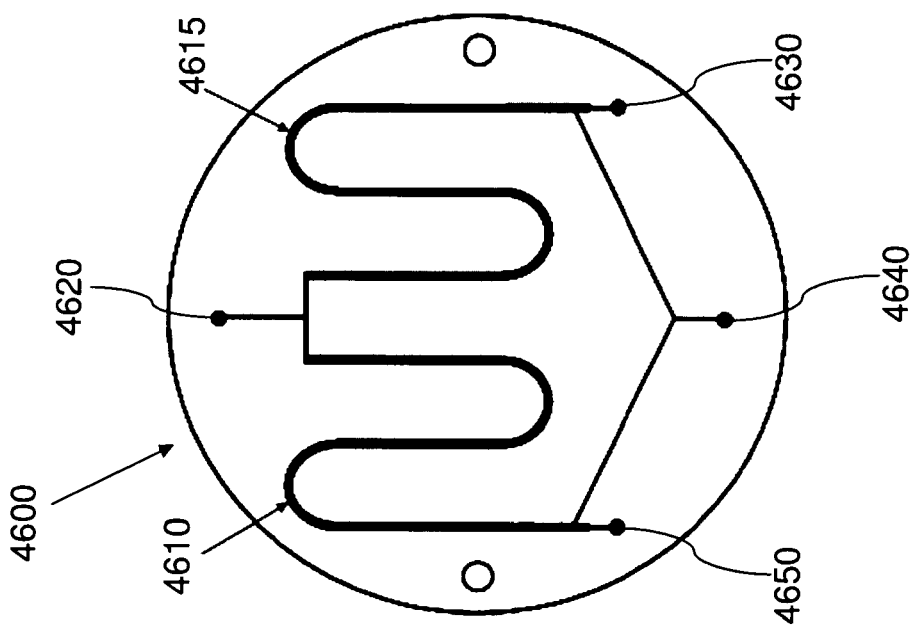
FIG. 46 shows a microfluidic device that includes an enlarged microchannel portion in accordance with certain examples.

In certain examples, the microfluidic devices described herein can be configured with one or more of the charging chambers. FIG. 46 shows one illustration of a microfluidic device with at least one charging chamber. The microfluidic device 4600 includes a first chamber 4610 and a second chamber 4615. A column effluent port 4640 is fluidically coupled to each of the first chamber 4610 and the second chamber 4615. Modulating gas may be introduced at a port 4630 or a port 4650 depending on which of the chambers 4610, 4615 is swept or flushed. A switching valve (not shown) is fluidically coupled to each of the ports 4630 and 4650 to control which port receives the modulating gas. One or more restrictors may be present to balance the flow in the system. When the modulating gas is introduced into the port 4630 the modulating gas will sweep chamber 4615 into the detector, and the column effluent will be charging the chamber 4610. When the modulating gas is switched to the port 4650, the chamber 4610 will be swept and the chamber 4610 will be charged. The chambers can be designed to be long and narrow to minimize dilution and dispersion of the sample as it is flushed.

In certain embodiments where a charging chamber is present, the chamber geometry can be selected to suit the operating conditions. For example, the following variables can be considered when selecting the chamber geometry and dimensions: column flow rate, modulating gas flow rate, pressure inside the microfluidic device and switching valve modulation frequency. In one illustration, if the column flow rate is in the range 0.5 to 3 mL/min (e.g., columns with a maximum internal diameter of 0.32 mm) and the flow rate into the detector is about 50 mL/min, then these assumptions provide a compression factor in the range 17× to 100×. If the internal pressure of the microfluidic device is about 8 psig, then a piece of fused silica tubing can be connected to the detector to provide about 50 mL/min at 8 psig. The restrictor geometry will be dependent on the particular detector selected. The charging chamber is desirably large enough to hold all the column effluent eluting from the column before it is pulsed. At the pressure inside the microfluidic device, the maximum volumetric flow rate from the column will be $$3\times(\text{Ambient Pressure})/(\text{Microfluidic device Pressure+Ambient Pressure})=3\times15/23=\sim2\text{ mL/min}$$

Table II lists the chamber capacities desired for a range of switching valve modulation frequencies with a 2 mL/min flow rate at 8 psig.

TABLE II

Predicted chamber capacity requirements

| Valve Frequency (Hz) | Charge Time (milliseconds) | Chamber Capacity (µL) |
|---|---|---|
| 5 | 100 | 13.33 |
| 10 | 50 | 6.67 |
| 20 | 25 | 3.33 |
| 50 | 10 | 1.33 |

If the channels of the microfluidic device are 80 microns in height and the chamber length is about 30 mm, the chamber widths can be selected as shown in Table III.

TABLE III

Predicted chamber dimensions

| Chamber Capacity (µL) | Chamber Height (µm) | Chamber Length (mm) | Chamber Width (µm) |
|---|---|---|---|
| 13.33 | 80 | 30 | 444 |
| 6.67 | 80 | 30 | 222 |
| 3.33 | 80 | 30 | 111 |
| 1.33 | 80 | 30 | 44 |

Tables II and III are provided as a guide, but any of the assumptions can be varied which would change the exact dimensions selected.

Figure 47:
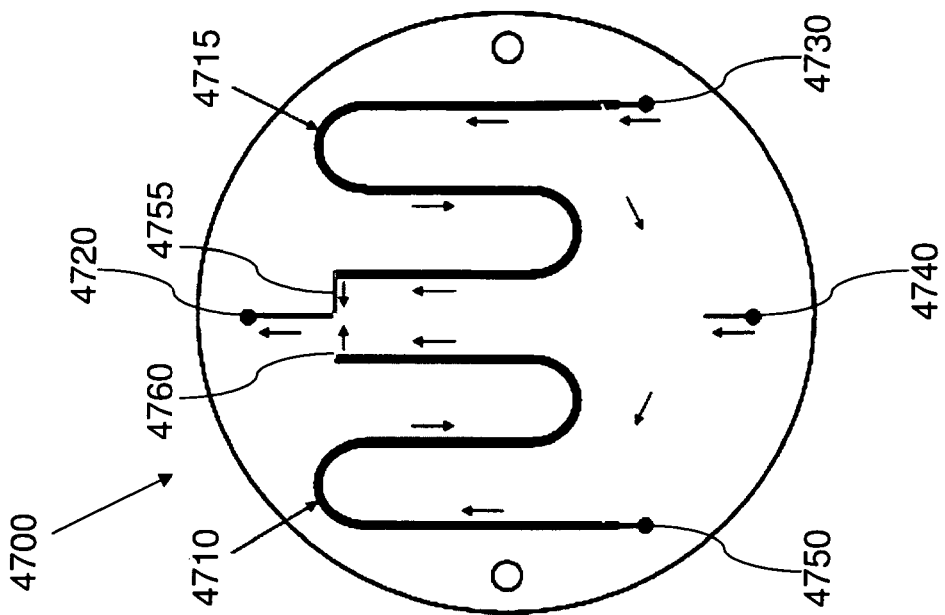
FIG. 47 shows a microfluidic device that includes a microchannel having restrictions therein, in accordance with certain examples.

In certain embodiments, the internal chamber channel geometry can also be selected to provide desired flow properties. For example, the geometry of the microchannels between the column port and each of the two chambers can alter the fluid flow. If these are too wide, the modulating gas will be able to cross between the two chambers and flush them both simultaneously. If they are too narrow, then the column port will increase in pressure from the column effluent and so the effluent will split into both chambers. The flow of modulating gas into the chamber being charged should be kept very low (e.g., <50 µL/min). FIG. 47 shows one illustration of how this process can be controlled using a microfluidic device. The microfluidic device 4700 includes a first chamber 4710 and a second chamber 4715. The microfluidic device 4700 also includes a plurality of ports. A column effluent port 4740 is fluidically coupled to the first chamber 4710 and the second chamber 4715. A 3-way switching valve (not shown) is fluidically coupled to a port 4730 and 4750 and can provide a modulating gas to either of the ports 4730, 4750 depending on the position of the valve. If the modulating gas is switched to the port 4730, then 50 mL/min of gas should flow through the chamber 4715 and out to a detector through a fluid flow path connected to port 4720. The chamber 4715 should not impose any significant restriction but the fluid flow path 4755 to the port 4720 may provide restricted flow. The flow rate of the modulating gas from the port 4730 through the chamber 4710 will be controlled by a fluid flow path 4760. It is the relative impedance of the flow paths 4755 and 4760 that will dictate the flow rate of the modulating gas through the chamber 4710 and the chamber 4715. Thus, the dimensions of the fluid flow paths 4755 and 4760 can be restricted or expanded, relative to the dimensions of other portions of the microchannel, to provide a desired flow rate through the microfluidic device.

Figure 48:
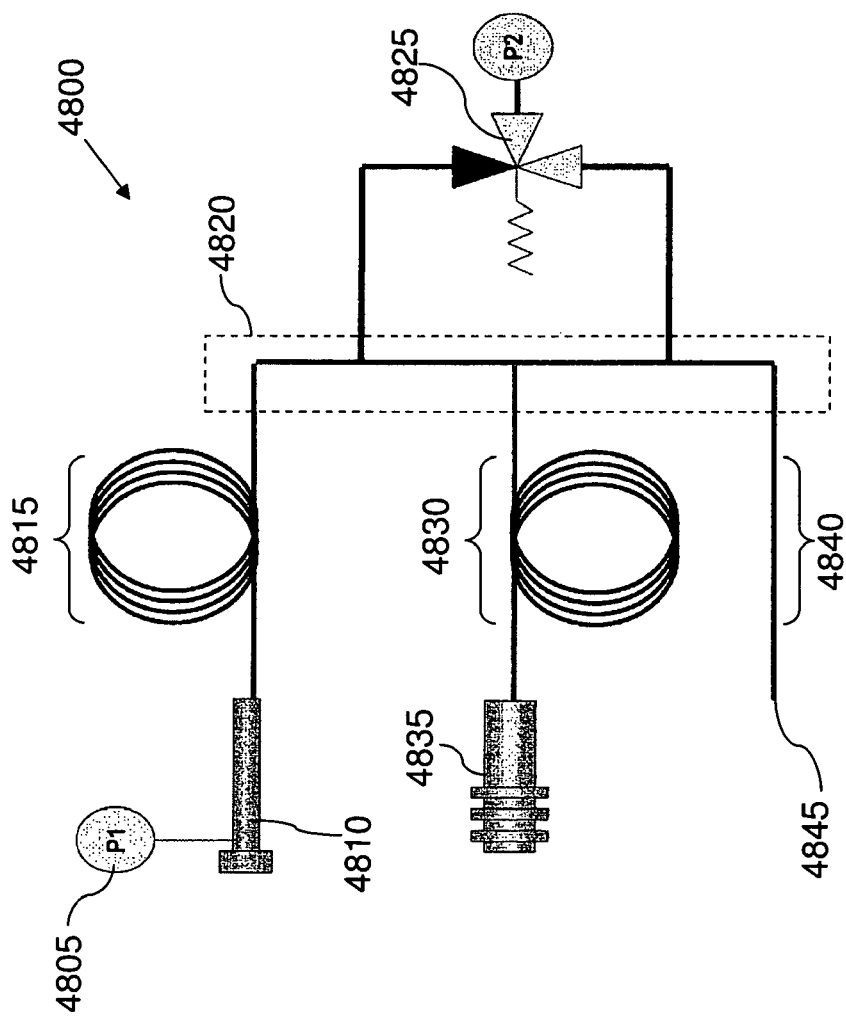
FIGS. 48-54 shows illustrations of chromatography systems that can be used, for example, peak splitting, in accordance with certain examples.

In certain embodiments, the microfluidic devices described herein can be used, for example, to split peaks. For example, individual peaks can be cut and provided to different detectors (or different components) or a single peak may be split and provided to two different components. For example, where a particular species in the sample is highly concentrated, it may be desirable to split that sample peak and send a portion of it to a vent rather than send the entire peak to a detector. Such splitting can overcome the dynamic range limitations of a column and/or a detector. In addition, large injection volumes can be used and the solvent peak can be split (or removed) entirely to avoid overloading the detector. One configuration of a system that is configured for peak splitting is shown in FIG. 48. The system 4800 includes an injector 4810 fluidically coupled to a carrier gas source 4805 and a first column 4815. The first column 4815 is fluidically coupled to a microfluidic device 4820, which itself is fluidically coupled to a switching valve 4825. A second column 4830 is fluidically coupled to the microfluidic device 4820 and a detector 4835. The microfluidic device 4820 is also fluidically coupled to a restrictor 4840 and a vent 4845. Depending on the position of the switching valve 4845, peaks eluting from the first column 4815 can be cut and provided to the second column 4830 or to the vent 4845. For example, contamination peaks or solvent peaks can be selectively provided to the vent 4845 so that they do not interfere with detection of sample peaks, which can be provided to the second column 4830 and to the detector 4835. In some examples, a portion of a peak can be cut and provided to the vent. For example, where one component in a sample (or a contaminant in a sample) is present at a substantially higher concentration than the other components, the highly concentrated component may be present at a concentration higher than the dynamic range of the detector, which can result in a flat top peak if the signal exceeds the maximum detector signal. By splitting the peak into two or more portions, the concentration may fall within the detector range to provide a more accurate assessment of how much of that component is present in the sample. Different speaks can be split different amounts, e.g., 25%, 50%, 75% or other splitting percentages. The system of FIG. 48 also permits venting through the vent 4845. Such venting can overcome issues resulting from large solvent amounts, which can permit larger injection volumes to be used. In addition, backflushing and MS vent functionalities can be performed as described herein.

Figure 49:
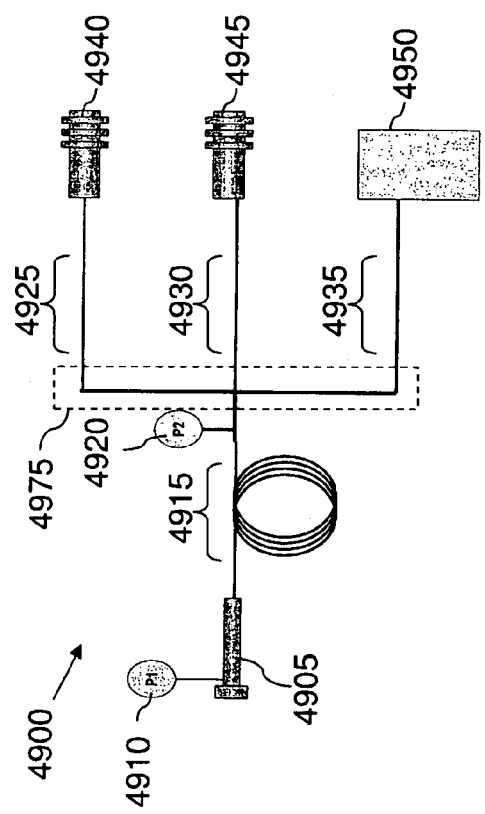

In certain embodiments, a system can be configured to split different peaks or provide different peaks to two or more detectors. Referring to FIG. 49, a system 4900 includes an injector 4905 fluidically coupled to a carrier gas source 4910 and a column 4915. The column 4915 is fluidically coupled to a microfluidic device 4975. A midpoint pressure regulator 4920 may optionally be fluidically coupled to the microfluidic device 4975. The microfluidic device 4975 is fluidically coupled to a first detector 4940 through a restrictor 4925, fluidically coupled to a second detector 4945 through a restrictor 4930, and fluidically coupled to a MS device 4950 through a restrictor 4935. In operation of the system, peaks may be cut and a portion can be provided to the first detector 4940 and the remainder of the cut peak can be provided to the second detector 4945. In an alternative, a portion of the peak can be provided to the MS device 4950. In some embodiments, entire peaks may be provided to the different detectors. Other uses of the system 4900 will be readily selected by the person of ordinary skill in the art, given the benefit of this disclosure.

Figure 50:
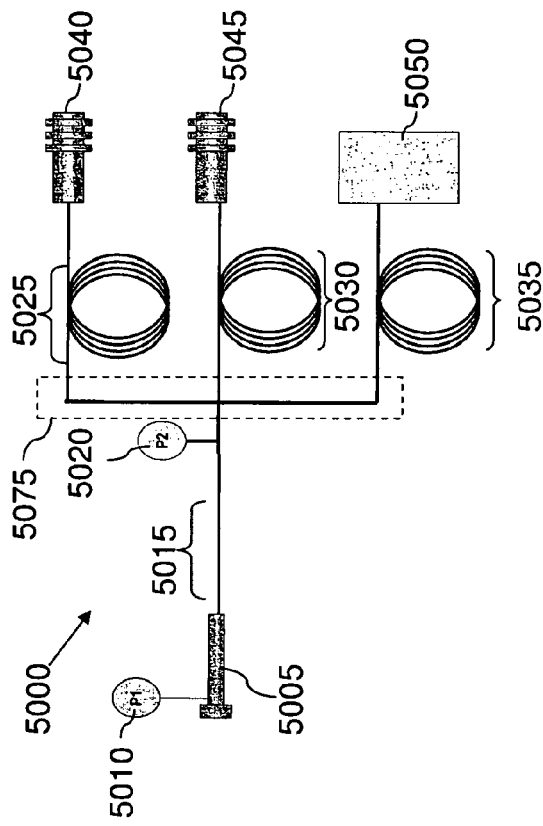

In certain embodiments, the sample can be split prior to any separation. One configuration of such a system is shown in FIG. 50. The system 5000 includes an injector 5005 fluidically coupled to a carrier gas source 5010. The injector 5005 is fluidically coupled to a microfluidic device 5075. A midpoint pressure regulator 5020 may optionally be fluidically coupled to the microfluidic device 5075 through a restrictor 5015. A switching gas source 5020 can be fluidically coupled to the microfluidic device 5075. The microfluidic device 5075 is fluidically coupled to a first detector 5040 through a first column 5025, fluidically coupled to a second detector 5045 through a second column 5030, and fluidically coupled to a MS device 5050 through a third column 5035. Sample can be injected into the system using the injector 5005 and can be split to the different components using the microfluidic device 5075. Separation can be performed using the columns 5025, 5030 and 5035 and the peaks can be provided to the corresponding detector. The configuration shown in FIG. 50 permits simultaneous analysis of a sample using different types of detectors and/or different types of column materials.

Figure 51:
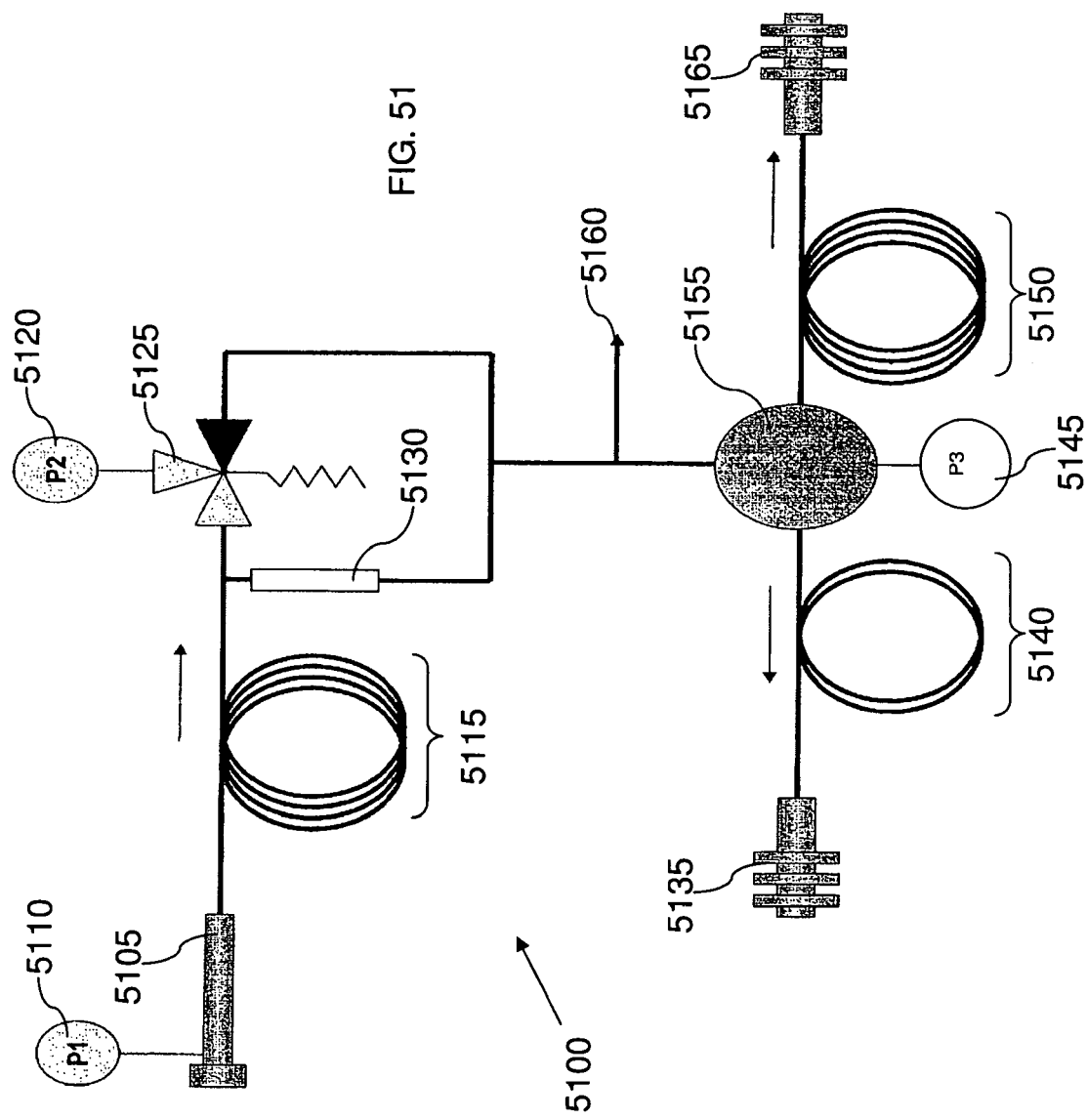

In certain embodiments, splitting of the peaks can permit use of different carrier gases. One configuration of such a system is shown in FIG. 51. The system 5100 includes an injector 5105 fluidically coupled to a first carrier gas source 5110. The injector 5105 is fluidically coupled to a first column 5115. A switching valve 5125 can be fluidically coupled to a microfluidic device 5155, a splitter 5160 and a second carrier gas source 5120, which may be the same as the first carrier gas source or may be different. The microfluidic device 5155 is also fluidically coupled to a third gas source 5145, which may be the same or may be different from the first and second carrier gas sources 5110, 5120. The microfluidic device 5155 is further fluidically coupled to a first detector 5135 through a second column 5140 and to a third detector 5165 through a third column 5150. In one scheme using the system of FIG. 51, the first gas source 5110 can be nitrogen which is used at a flow rate of 10 cm/sec. The second gas source 5120 may also be nitrogen, which can be introduced at a sufficient flow rate to provide a flow rate through the second column 5140 of about 40 cm/sec. The second gas source can be provided, for example, to sweep effluent from a charging chamber 5130. The third gas source can be hydrogen and can be provided at a flow rate of about 40 cm/sec to the third column 5150. In this configuration, the different carrier gases can provide different separation using the second and third columns 5140, 5150. Such different carrier gases may be desirable where, for example, a single type of carrier gas does not provide suitable separation of all the components in the sample.

Figure 52B:
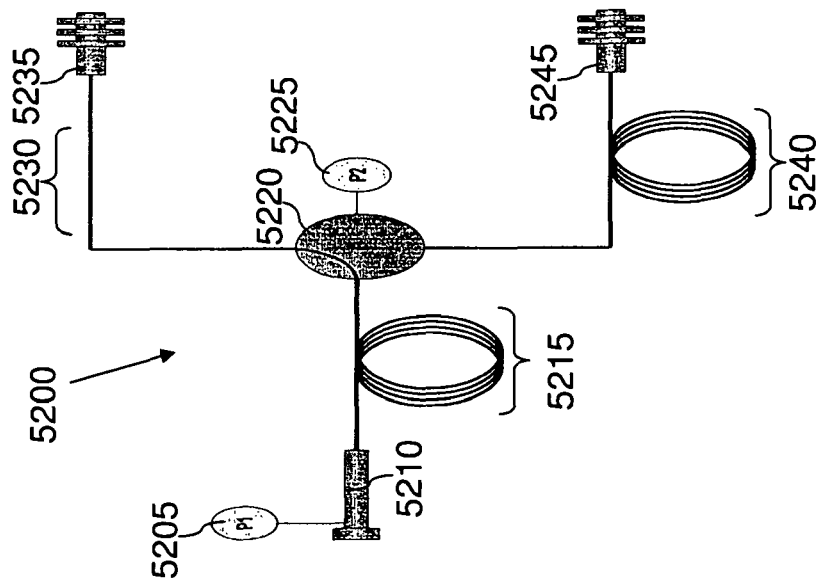
Figure 52A:
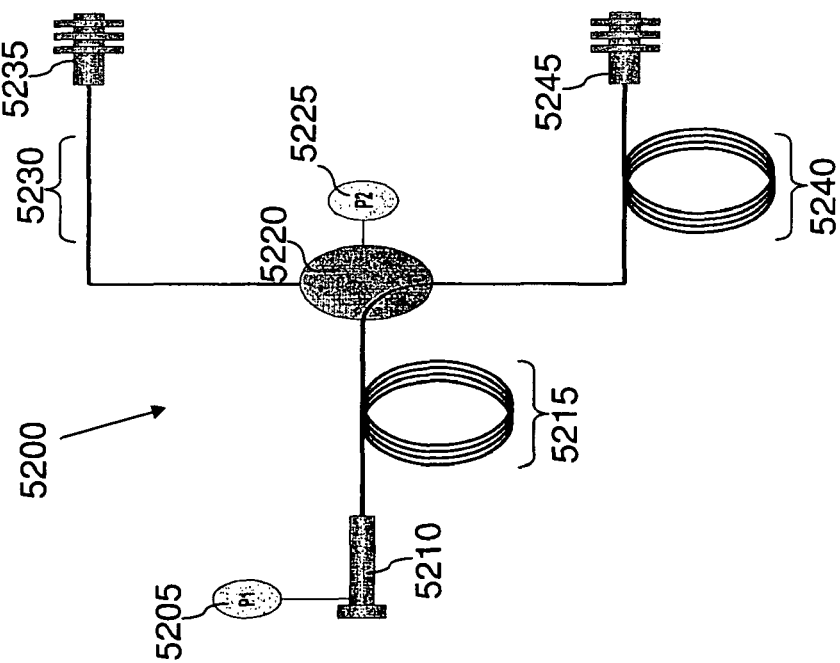

In certain embodiments, the systems described herein can be used for multidimensional separations. One illustration is shown in FIGS. 52A and 52B. The system 5200 includes an injector 5210 fluidically coupled to a carrier gas source 5205 and a first column 5215. The first column 5215 is fluidically coupled to a microfluidic device 5220, which itself is fluidically coupled to a modulating gas source 5225. The microfluidic device 5220 is also fluidically coupled to a first detector 5235 through a restrictor 5230 and to a second detector 5245 through a second column 5240. The microfluidic device 5220 is also typically in fluid communication with a switching valve (not shown), which can permit fluid flow from the first column 5215 to the second column 5240 and second detector 5245 in one position (FIG. 52A) and can permit fluid flow to the second detector 5235 through the restrictor 5230 in another position (FIG. 52B). The position of the switching valve may be changed to control which components of the system receive column effluent. Such direction of flow provides for different data sets which can be used to provide a better analysis of components in the sample and can be, if desired, provided on the same chromatogram for easier analysis.

Figure 53:
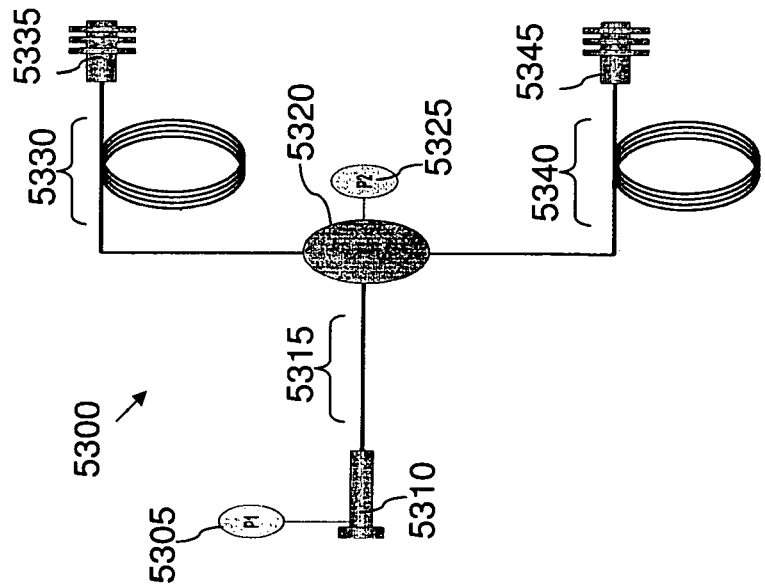

In some embodiments, the multidimensional separation can occur after column effluent is split but before any separation has occurred. One configuration of a system that uses a split flow for multidimensional analysis is shown in FIG. 53. The system 5300 includes an injector 5310 fluidically coupled to a carrier gas source 5305 and a restrictor 5315. The restrictor 5315 is fluidically coupled to a microfluidic device 5320, which itself is fluidically coupled to a modulating gas source 5325. The microfluidic device 5320 is also fluidically coupled to a first detector 5335 through a first column 5330 and to a second detector 5345 through a second column 5340. The microfluidic device 5320 is also typically in fluid communication with a switching valve (not shown), which can split the fluid flow from the injector 5310 and provide the split flow to the different columns of the system 5300. Such splitting permits the use of different separation media in the two columns to provide different data sets and different separations using a single system.

Figure 54:
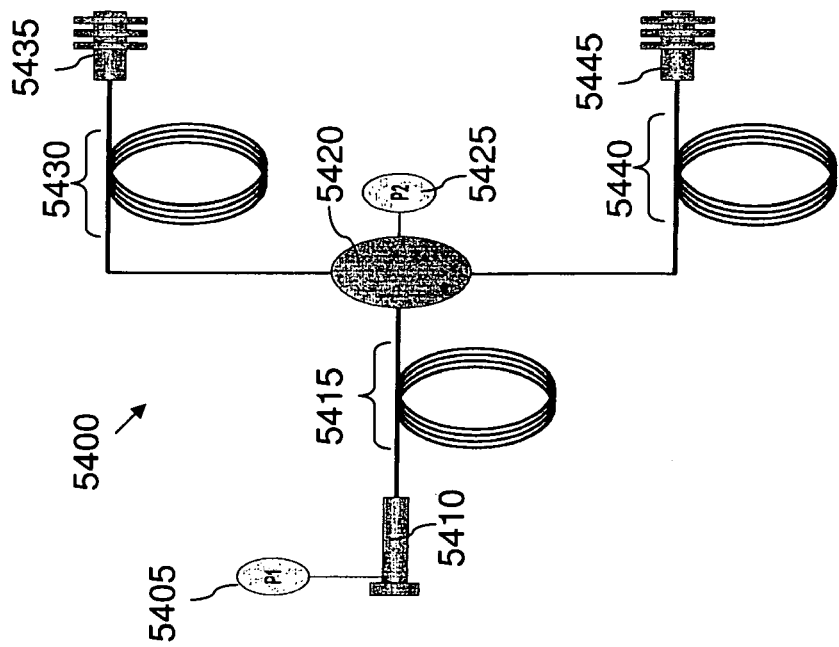

In certain examples, a system for use in a multidimensional separation, e.g., GCxGC, can include three or more columns. One system that includes three columns is shown in FIG. 54. The system 5400 includes an injector 5410 fluidically coupled to a carrier gas source 5405 and a first column 5415. The first column 5415 is fluidically coupled to a microfluidic device 5420, which itself is fluidically coupled to a modulating gas source 5425. The microfluidic device 5420 is also fluidically coupled to a first detector 5435 through a second column 5430 and to a second detector 5445 through a third column 5440. The microfluidic device 5420 is also typically in fluid communication with a switching valve (not shown), which can split the column effluent flow (or particular peaks if desired) from the first column 5415 and provide the split flow to the two other columns of the system 5400. Such splitting permits the use of different separation media in the three columns, if desired, to provide different data sets and different separations using a single system.

In certain examples, the devices, methods and systems described herein (or portions thereof) can be implemented or controlled using a computer or other device that includes a processor, or the devices and systems described herein can be electrically coupled to a computer system or processor. Such computer implemented methods can provide for more user friendly implementation of the methods by permitting control using a graphical user interface or the like. In addition, the computer can be used to monitor flow rates, receive data from one or more detectors and to store or recall separation routines for subsequent use. The computer system typically includes at least one processor optionally electrically coupled to one or more memory units. The computer system may be, for example, a general-purpose computer such as those based on Unix, Intel PENTIUM-type processor, Motorola PowerPC, Sun UltraSPARC, Hewlett-Packard PA-RISC processors, or any other type of processor. In some examples, the processor may be an inexpensive processor that may be programmable to receive inputs and output treatment parameters based on the received inputs. It should be appreciated that one or more of any type computer system may be used according to various embodiments of the technology. Further, the system may be located on a single computer or may be distributed among a plurality of computers attached by a communications network. A general-purpose computer system may be configured, for example, to perform any of the described functions including but not limited to: restrictor length and diameter calculations, gas source control, switching valve control, temperature control, run times, and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. Memory is typically used for storing programs and data during operation of the computer system. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically is electrically coupled to the detector such that electrical signals may be provided to and from the detector to the computer to receive data for storage and/or processing. The computer system may also include one or more input devices, for example, a keyboard, mouse, trackball, microphone, touch screen, manual switch (e.g., override switch) and one or more output devices, for example, a printing device, display screen, speaker. In addition, the computer system may contain one or more interfaces (not shown) that connect the computer system to a communication network (in addition or as an alternative to the interconnection device).

The storage system typically includes a computer readable and writeable nonvolatile recording medium in which signals are stored that define a program to be executed by the processor or information stored on or in the medium to be processed by the program. For example, the oven temperatures, flow rates, switching valve position and modulation frequencies and the like for a particular separation may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system.

In certain examples, the computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component.

Although a computer system is described by way of example as one type of computer system upon which various aspects of the technology may be practiced, it should be appreciated that aspects are not limited to being implemented on the illustrated computer system. Various aspects may be practiced on one or more computers having a different architecture or components. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used, and in certain embodiments a simple set of commands or instructions may function as the operating system.

In accordance with certain examples, the processor and operating system may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used. In certain examples, the hardware or software is configured to implement cognitive architecture, neural networks or other suitable implementations.

One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In accordance with certain examples, various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain examples, a user interface may be provided such that a user may enter desired flow rates, tubing lengths and diameters, column types, solvent gradient runs and other information commonly entered prior to a gas or liquid chromatography separation is commenced. Other features for inclusion in a user interface will be readily selected by the person of ordinary skill in the art, given the benefit of this disclosure.

In certain embodiments, the microfluidic devices described herein may be packaged in a kit optionally with instructions for using the microfluidic device. In some examples, the kit may further include a computer readable medium that contains algorithms suitable for implementing flow control or modulation as described herein. The kit may further include fittings, tubing, restrictors or the like of a desired length or diameter to facilitate a desired flow rate in the system. In some examples, one or more separation columns may also be included in the kit.

Certain specific examples are described below to illustrate further some of the new and useful features of the technology described herein.

Example 1

To validate the tubing diameter algorithms, a length of fused silica tubing (listed as having an internal diameter of 150 microns) was tested with helium and nitrogen carrier gases. A least squares linear fit was applied to the flow rate versus the square of the absolute applied pressure to establish the value of the constant b in Equation (17) and $d_c$ was calculated from Equation (18). The ambient pressure was determined from a digital barometer at the location and the viscosity at the ambient temperature was taken from tables. The results are given in Tables IV (helium gas) and V (nitrogen gas) and are listed in order of decrementing length L.

TABLE IV

| | Measured Flow Rate (mL/min) | | | | | | | | | | |
|---|---|---|---|---|---|---|---|---|---|---|---|
| L (cm) | 80 (psig) | 70 (psig) | 60 (psig) | 50 (psig) | 40 (psig) | 30 (psig) | 20 (psig) | 10 (psig) | 5 (psig) | Fit $r^2$ | $d_c$ (μm) |
| 200 | 42.40 | 33.70 | 25.90 | 19.30 | 13.50 | 8.74 | 4.68 | 1.87 | | 1.0000 | 152.9 |
| 190 | 44.20 | 35.40 | 27.10 | 20.30 | 14.30 | 9.16 | 4.91 | 2.01 | | 0.9999 | 152.6 |
| 180 | 46.90 | 37.40 | 28.70 | 21.50 | 15.10 | 9.64 | 5.20 | 2.15 | | 1.0000 | 152.8 |
| 170 | 49.30 | 39.00 | 30.30 | 22.60 | 15.90 | 10.10 | 5.48 | 2.29 | | 0.9999 | 152.4 |
| 160 | 53.10 | 42.30 | 32.60 | 24.20 | 16.90 | 10.80 | 5.87 | 2.44 | | 1.0000 | 153.1 |
| 150 | 55.50 | 44.30 | 34.40 | 25.50 | 18.00 | 11.40 | 6.25 | 2.61 | | 1.0000 | 152.3 |
| 140 | 60.70 | 48.40 | 37.20 | 27.40 | 19.50 | 12.50 | 6.82 | 2.84 | | 1.0000 | 153.0 |
| 130 | 65.40 | 52.10 | 40.00 | 29.60 | 21.00 | 13.50 | 7.31 | 3.04 | | 1.0000 | 153.0 |
| 120 | 70.50 | 56.40 | 43.60 | 32.30 | 22.60 | 14.60 | 8.01 | 3.20 | | 1.0000 | 152.9 |
| 110 | 76.30 | 61.20 | 47.40 | 35.10 | 24.60 | 15.90 | 8.75 | 3.56 | | 1.0000 | 152.6 |
| 100 | 84.00 | 67.00 | 52.00 | 38.40 | 27.00 | 17.40 | 9.60 | 3.86 | | 1.0000 | 152.6 |
| 90 | 93.00 | 74.20 | 57.80 | 42.80 | 29.80 | 19.40 | 10.60 | 4.25 | 1.90 | 1.0000 | 152.5 |
| 80 | 104.00 | 82.90 | 64.70 | 48.00 | 33.60 | 21.60 | 12.00 | 4.65 | 2.10 | 0.9999 | 152.3 |
| 70 | 118.00 | 94.10 | 73.20 | 54.40 | 38.20 | 24.60 | 13.80 | 5.28 | 2.35 | 0.9999 | 152.0 |
| 60 | 136.00 | 109.00 | 84.80 | 63.10 | 44.20 | 28.30 | 15.90 | 6.16 | 2.74 | 1.0000 | 151.6 |
| 50 | 163.00 | 130.00 | 101.00 | 75.00 | 52.80 | 34.00 | 19.00 | 7.42 | 3.30 | 1.0000 | 151.4 |
| 40 | 201.00 | 162.00 | 125.00 | 93.60 | 66.10 | 42.70 | 23.70 | 9.48 | 4.14 | 0.9999 | 151.0 |
| 30 | 265.00 | 211.00 | 166.00 | 123.00 | 87.10 | 56.50 | 31.50 | 12.60 | 5.43 | 0.9998 | 150.4 |

TABLE V

| | Measured Flow Rate (mL/min) | | | | | | | | | | |
|---|---|---|---|---|---|---|---|---|---|---|---|
| L (cm) | 80 (psig) | 70 (psig) | 60 (psig) | 50 (psig) | 40 (psig) | 30 (psig) | 20 (psig) | 10 (psig) | 5 (psig) | Fit $r^2$ | $d_c$ (μm) |
| 200 | | 37.60 | 28.90 | 21.70 | 15.30 | 9.77 | 5.19 | 2.21 | | 0.9999 | 153.5 |
| 190 | | 38.70 | 30.00 | 22.40 | 15.80 | 10.20 | 5.47 | 2.25 | | 0.9999 | 152.7 |
| 180 | | 40.30 | 31.50 | 23.50 | 16.50 | 10.60 | 5.74 | 2.37 | | 0.9999 | 152.3 |
| 170 | | 43.80 | 33.80 | 25.20 | 17.80 | 11.40 | 6.19 | 2.55 | | 1.0000 | 153.1 |
| 160 | | 46.30 | 35.90 | 26.90 | 18.90 | 12.10 | 6.64 | 2.74 | | 0.9999 | 153.0 |
| 150 | | 47.60 | 37.20 | 27.80 | 19.90 | 12.80 | 7.02 | 2.90 | | 0.9998 | 151.5 |
| 140 | | 52.70 | 41.20 | 30.40 | 21.50 | 14.00 | 7.64 | 3.11 | | 0.9999 | 152.8 |
| 130 | | 56.10 | 44.00 | 32.80 | 23.20 | 15.10 | 8.23 | 3.37 | | 0.9998 | 152.4 |
| 120 | | 59.60 | 47.00 | 35.00 | 24.80 | 16.10 | 8.80 | 3.60 | | 0.9998 | 151.7 |

TABLE V-continued

| | Measured Flow Rate (mL/min) | | | | | | | | | | |
|---|---|---|---|---|---|---|---|---|---|---|---|
| L (cm) | 80 (psig) | 70 (psig) | 60 (psig) | 50 (psig) | 40 (psig) | 30 (psig) | 20 (psig) | 10 (psig) | 5 (psig) | Fit r² | $d_c$ (μm) |
| 110 | | | 52.10 | 38.40 | 27.10 | 17.50 | 9.76 | 3.94 | | 1.0000 | 152.9 |
| 100 | | | 56.90 | 42.50 | 29.70 | 19.30 | 10.70 | 4.26 | | 1.0000 | 152.8 |

Tables IV and V show that a highly consistent value for the internal diameter is achieved as the restrictor tubing is progressively shortened. The mean values (152.3 μm for helium and 152.6 μm for nitrogen) are very close and the precision in the calculations is excellent (0.49% RSD for helium and 0.40% RSD for nitrogen).

Figure 55:
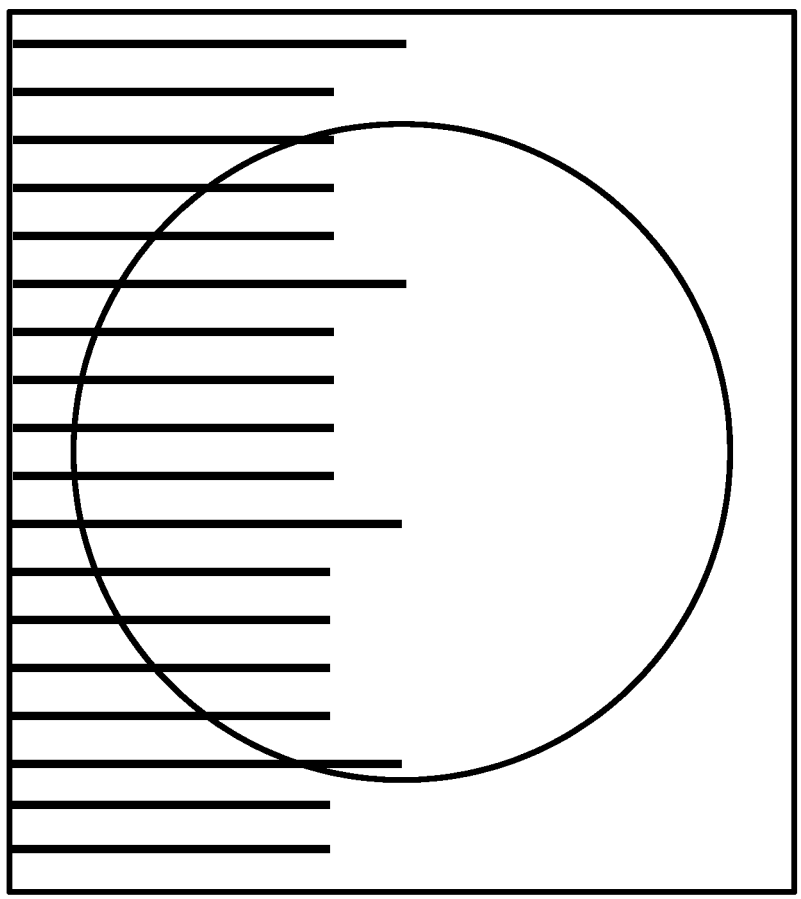
FIG. 55 is a photograph showing the diameter of tubing, in accordance with certain examples.

To validate the accuracy of these results, the sections of fused silica tubing removed during the flow measurement tests were examined under a 500× magnification microscope and the true diameters determined by photomicrography. FIG. 55 shows a photomicrograph of the end of one section of the fused silica tubing with an overlaid graticule with 10 microns scale divisions. Table VI lists the results of the manual measurements taken through the microscope. These measurements agree very closely with the calculated values in Tables IV and V.

TABLE VI

| Section Taken (cm) | Measured Bore (μm) |
|---|---|
| 200 | 153 |
| 180 | 153 |
| 160 | 152 |
| 140 | 152 |
| 120 | 153 |
| 100 | 153 |

Thus, to better determine the true size of tubing used in fluid chromatography systems, a calibration protocol can be implemented to accurately assess the true internal diameter of tubing, e.g., columns, restrictors, etc. used in the systems.

Example 2

Figure 56:
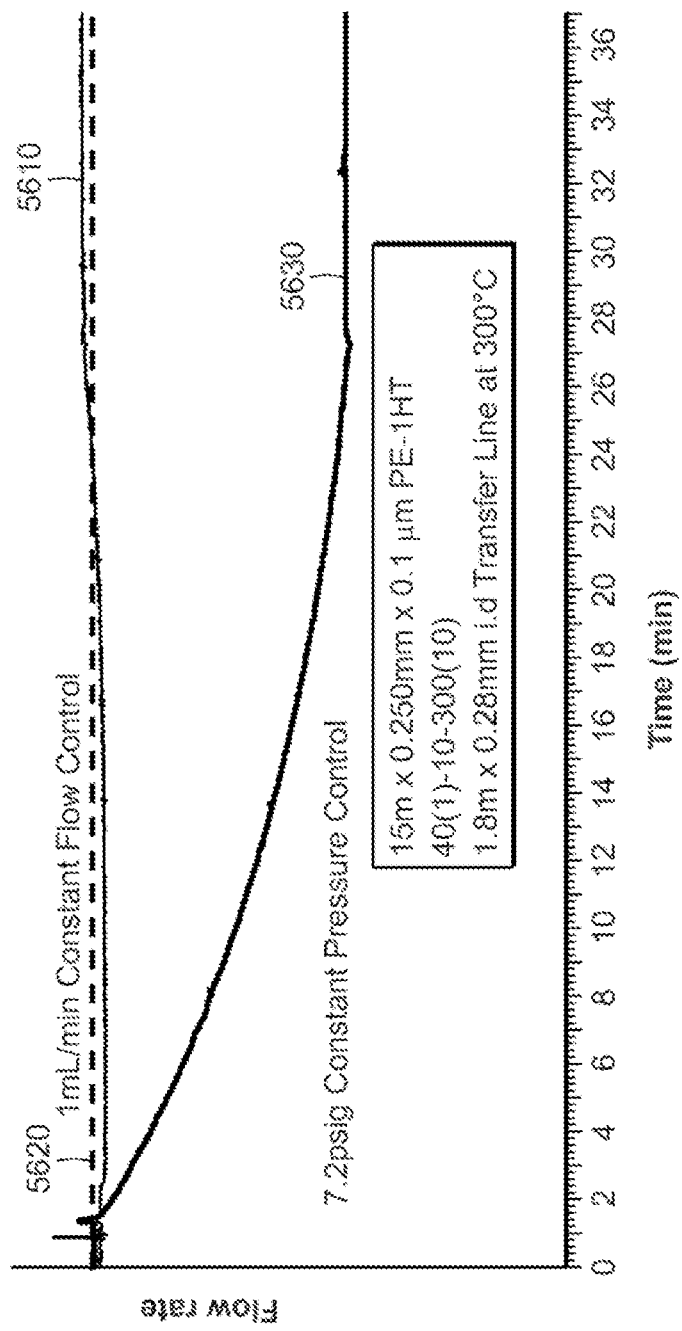
FIG. 56 is a graph showing the results of flow rate measurements using the flow control algorithms described herein and using pressure control, in accordance with certain examples.

The results from a thermal desorption system that uses algorithms based on the equations described above to control the flow rate of gas through a transfer line and a column are shown in FIG. 56. The carrier gas was doped with a fixed concentration of methane so that the mass flow rate of gas eluting from the column could be directly monitored by a flame ionization detector. FIG. 56 shows plots of the detector signal during a column temperature program with constant pressure control and then with constant flow control. As can be seen from these plots, the mass flow rate is reasonably constant during the program when constant flow control is used.

In FIG. 56, the flow rates were controlled as the column temperature was increased. The methane was added to the column and the resulting signal was used to monitor the detector response as a function of the flow rate. The oven was heated to 40° C. and maintained at this temperature for 1 minute. The temperature was then increased by 10° C./minute up to a final temperature of 300° C. The final temperature was maintained for 10 minutes. Curve 5610 represents the actual flow rate, curve 5620 represents the expected flow rate, and curve 5630 represents the flow rate without use of the flow control (where constant pressure control was used). Where pressure control was used, the flow rate differed markedly from the desired flow rate. Where the flow control algorithms described herein are implemented, the flow rate closely tracked that of the desired flow rate.

Example 3

FIGS. 34 and 35A-35C show illustrations of chromatography peaks where modulation was performed, as described herein. Referring to FIG. 34, a single peak is shown. The modulation breaks the peak into a plurality of individual modulated portions. Modulation was performed at 10 Hz using the controller of FIGS. 33A and 33B and the microfluidic device of FIG. 11. The column used was a 30 m×0.25 mm×0.25 micron methyl silicone column. Helium was used as the mobile phase. The inlet pressure was 40 psig, and the midpoint pressure was 30 psig (helium gas). The oven was heated to 35° C. and maintained at this temperature for 1 minute. The temperature was then increased by 10° C. per minute up to a temperature of 300° C. A fast FID detector at 275° C. was used to detect the peaks. A 100 mL/min split injector was used to introduce the sample, which was 1 microgram/microliter NIOSH aromatics (0.2 microliters was injected).

Referring to FIGS. 35A-35C, three different traces are shown. In FIG. 35A, two peaks 3510, 3520 representative of sample effluent from a first column are shown. In FIG. 35B, a single peak 3530 representative of sample effluent from a second column is shown. These peaks can be analyzed simultaneously using the modulation techniques described herein. Referring to FIG. 35C, the modulated output of the different samples is shown where, for example, the sample from the first and second columns can be provided to a single output. The peaks 3510 and 3530 overlap or are interlaced in the modulated output as shown in the modulated signal group 3540. The peak 3520 is shown as a modulated peak 3550. In this manner, sample peaks from different columns can be analyzed simultaneously.

Example 4

Figure 57:
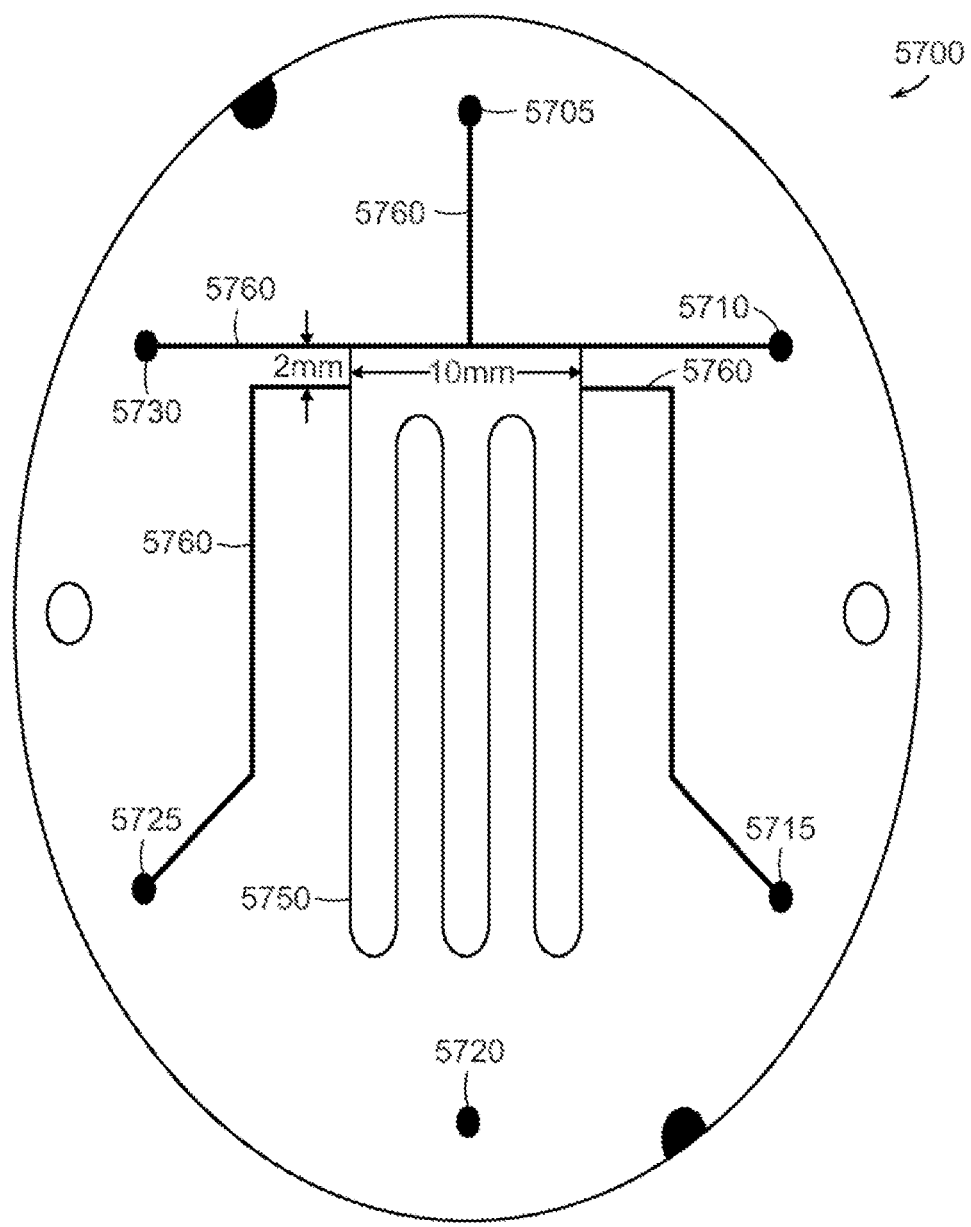
FIG. 57 is schematic showing a microfluidic device that includes an internal bypass restrictor, in accordance with certain examples.

A microfluidic device that included an internal bypass restrictor is shown in FIG. 57. The resulting microfluidic device (FIG. 57) included a plurality of ports 5705, 5710, 5715, 5720, 5725 and 5730. The port 5705 is designed to receive effluent from a column. A switching gas from a solenoid valve can be connected to each of the ports 5715 and 5725. Outlet ports 5710 and 5730 can be connected to columns or restrictors or other devices. The internal bypass restrictor 5750 has a diameter that is less than that of other portions 5760 of the internal microfluidic channel. The particular diameter and length selected for this internal bypass restrictor can provide for flow control using the microfluidic device.

When introducing elements of the examples disclosed herein, the articles "a," "an," and "the" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure.

What is claimed is:

1. A method comprising:
    selecting a fluid flow rate to be used in a chromatography system configured to receive a microfluidic device comprising a plurality of ports fluidically coupled to each other through an internal microchannel of the microfluidic device;
    determining a dimension of a restrictor in the chromatography system comprising the microfluidic device to provide the selected fluid flow rate; and
    placing the restrictor of determined dimension downstream of the microfluidic device.

2. A method comprising:
    selecting a fluid flow rate to be used in a chromatography system;
    determining a dimension of a restrictor in the chromatography system to provide the selected fluid flow rate, in which the dimension is restrictor internal diameter of the restrictor and the internal diameter is calculated using the following equation $$d_c = \sqrt[4]{\frac{256 \cdot L \cdot p_a \cdot \eta}{b \cdot \pi}}$$

where $d_r$ is the internal diameter of the restrictor, L is restrictor length, $p_a$ is absolute pressure, $\eta$ is viscosity of a carrier gas and b is a constant.

3. The method of claim 2, further comprising configuring the chromatography system with a switching valve comprising a 3-way solenoid valve that is actuated at a frequency of about 10 Hz to about 100 Hz.

4. The method of claim 2, further comprising balancing pressure in the system by configuring the system with the restrictor between a detector and a microfluidic device.

5. The method of claim 4, further comprising providing column effluent from a first charging chamber to a first detector fluidically coupled to the microfluidic device and providing the column effluent from a second charging chamber to a second detector fluidically coupled to the microfluidic device, in which the restrictor is between the first detector and the microfluidic device.

6. The method of claim 5, further comprising configuring each of the first and second charging chambers as internal chambers within the microfluidic device.

7. The method of claim 6, further comprising configuring a rate of fluid flow from a modulating gas source to be at least five times greater than a rate of fluid flow of column effluent into the first and second charging chambers.

8. The method of claim 4, further comprising determining a dimension of a second restrictor in the chromatography system to provide a second selected fluid flow rate, and balancing the pressure in the system by configuring the system with the restrictor between a first detector and a microfluidic device and configuring the system with the second restrictor between a second detector and the microfluidic device.

9. A method comprising:
    selecting a fluid flow rate to be used in a chromatography system;
    determining a dimension of a restrictor in the chromatography system to provide the selected fluid flow rate, in which the dimension is restrictor length and the restrictor length is calculated using the following equation $$L_r = \frac{\left[\frac{\pi \times T_a \times d_r^4}{256 \times F_a \times p_a} \times (p_i^2 - p_{or}^2) - T_{r2} \times \eta_{r2} \times L_{r2}\right]}{T_{r1} \times \eta_{r1}} + L_{r2}$$

where $L_{r1}$ is the length of the restrictor inside an oven of the chromatography system, $L_{r2}$ is the length of the restrictor inside a detector of the chromatography system, $\eta_{r1}$ is the viscosity of carrier gas at the oven temperature, $\eta_{r2}$ is the viscosity of carrier gas at the detector temperature, $T_{r1}$ is the absolute temperature of the oven, $T_{r2}$ is the absolute temperature of the detector, $p_i$ is the inlet pressure of the restrictor, $p_{or}$ is the outlet pressure of the restrictor, $p_a$ is the absolute pressure and Fa is the flow rate.

10. The method of claim 9, further comprising configuring the chromatography system with a switching valve comprising a 3-way solenoid valve that is actuated at a frequency of about 10 Hz to about 100 Hz.

11. The method of claim 9, further comprising balancing pressure in the system by configuring the system with the restrictor between a detector and a microfluidic device.

12. The method of claim 11, further comprising providing column effluent from a first charging chamber to a first detector fluidically coupled to the microfluidic device and providing the column effluent from a second charging chamber to a second detector fluidically coupled to the microfluidic device, in which the restrictor is between the first detector and the microfluidic device.

13. The method of claim 12, further comprising configuring each of the first and second charging chambers as internal chambers within the microfluidic device.

14. The method of claim 13, further comprising configuring a rate of fluid flow from a modulating gas source to be at least five times greater than a rate of fluid flow of column effluent into the first and second charging chambers.

15. The method of claim 11, further comprising determining a dimension of a second restrictor in the chromatography system to provide a second selected fluid flow rate, and balancing the pressure in the system by configuring the system with the restrictor between a first detector and a microfluidic device and configuring the system with the second restrictor between a second detector and the microfluidic device.

16. A method comprising:
    selecting a fluid flow rate to be used in a chromatography system;
    determining a dimension of a restrictor in the chromatography system to provide the selected fluid flow rate and configuring the chromatography system with a switching valve upstream of the restrictor, the switching valve configured to actuate between a first position and a second position, the first position permitting fluid flow from a modulating gas source to a first charging chamber of a microfluidic device to provide column effluent from the first charging chamber to a detector fluidically coupled to the microfluidic device, and the second position permitting fluid flow from the modulating gas source to the second charging chamber of the microfluidic device to provide column effluent from the second charging chamber to the detector fluidically coupled to the microfluidic device.

17. The method of claim 16, further comprising configuring the switching valve as a 3-way solenoid valve that is actuated at a frequency of about 10 Hz to about 100 Hz.

18. The method of claim 16, further comprising balancing pressure in the system by configuring the system with the restrictor between a detector and the microfluidic device.

19. The method of claim 18, further comprising providing the column effluent from the first charging chamber to a first detector fluidically coupled to the microfluidic device and providing the column effluent from the second charging chamber to a second detector fluidically coupled to the microfluidic device, in which the restrictor is between the first detector and the microfluidic device.

20. The method of claim 18, further comprising determining a dimension of a second restrictor in the chromatography system to provide a second selected fluid flow rate, and balancing the pressure in the system by configuring the system with the restrictor between the first detector and the microfluidic device and configuring the system with the second restrictor between the second detector and the microfluidic device.

21. The method of claim 16, further comprising configuring each of the first and second charging chambers as internal chambers within the microfluidic device.

22. The method of claim 16, further comprising configuring a rate of fluid flow from the modulating gas source to be at least five times greater than a rate of fluid flow of the column effluent into the first and second charging chambers.

\* \* \* \* \*